US009994548B2

(12) United States Patent
Brown et al.

(10) Patent No.: US 9,994,548 B2
(45) Date of Patent: Jun. 12, 2018

(54) PHENYL-SUBSTITUTED NICOTINIC LIGANDS, AND METHODS OF USE THEREOF

(71) Applicants: Georgetown University, Washington, DC (US); Duke University, Durham, NC (US)

(72) Inventors: Milton L. Brown, Brookeville, MD (US); Mikell A. Paige, Fairfax, VA (US); Yingxian Xiao, Potomac, MD (US); Kenneth J. Kellar, Bethesda, MD (US); Venkata M. Yenugonda, McLean, VA (US); Edward D. Levin, Chapel Hill, NC (US); Amir H. Rezvani, Chapel Hill, NC (US)

(73) Assignees: Georgetown University, Washington, DC (US); Duke University, Durham, NC (US)

(*) Notice: Subject to any disclaimer, the term of this patent is extended or adjusted under 35 U.S.C. 154(b) by 0 days. days.

(21) Appl. No.: 15/162,237

(22) Filed: May 23, 2016

(65) Prior Publication Data

US 2017/0107197 A1  Apr. 20, 2017

Related U.S. Application Data

(63) Continuation of application No. 14/357,701, filed as application No. PCT/US2012/064393 on Nov. 9, 2012, now Pat. No. 9,346,784.

(60) Provisional application No. 61/647,223, filed on May 15, 2012, provisional application No. 61/558,812, filed on Nov. 11, 2011.

(51) Int. Cl.
*A61K 31/4427* (2006.01)
*C07D 401/12* (2006.01)
*C07D 213/65* (2006.01)

(52) U.S. Cl.
CPC ......... *C07D 401/12* (2013.01); *C07D 213/65* (2013.01)

(58) Field of Classification Search
CPC ..................... A61K 31/4427; A31K 31/4427
USPC ......................................................... 514/340
See application file for complete search history.

(56) References Cited

U.S. PATENT DOCUMENTS

| 4,508,560 | A | 4/1985 | Brunner et al. |
| 5,629,325 | A | 5/1997 | Lin et al. |
| 2003/0199511 | A1 | 10/2003 | Li et al. |
| 2010/0129291 | A1 | 5/2010 | Xiao et al. |

OTHER PUBLICATIONS

Layzer, Degenerative Diseases of the Nervous System, Cecil Textbook of Medicine, 20th Edition, vol. 2, pp. 2050-2057, 1996.*
Damasio, Alzheimer's Disease and Related Dementias, Cecil Textbook of Medicine, 20th Edition, vol. 2, pp. 1992-1996, 1996.*
Romanelli et al., Cholinergic Nicotinic Receptors: Competitive Ligands, Allosteric Modulators, and Their Potential Applications, Medicinal Research Reviews, vol. 23, No. 4, pp. 393-426, 2003.*
Damaj et al. Medline Abstract (Psychopharacologia, vol. 120, Issue 4, pp. 483-490, Aug. 1995.*
Mirza et al., "The role of nicotinic, etc.," (Psychopharmacology (Berl). 148(3):243-50), Feb. 2000.*
Terry et al., (Neuroscience, 101(2):357-68), 2000.*
Court et al., "Nicotinic receptors, etc.," (J Chem Neuroanat. 20(3-4):281-98), Dec. 2000.*
Holladay et al., "Neuronal Nicotinic, etc.," J of Med. Chem. vol. 40, No. 26 (1997), pp. 4169-4194.*
Posadas et al., "Nicotinic Receptors, etc.," Current Neuropharmacology, 2013, 11, 298-314.*
Salamone et al., "Aberrations in Nicotinic, etc.," McGill J. Med., 2000, 5:90-97.*
Simosky et al., "Nicotinic Agonists, etc.," Current Drug Targets—CNS & Neurological Disorders, 2002, 1, 149-162.*
Kalamida et al., "Muscle and neuronal, etc.," FEBS Journal, 274 (2007), 3799-3845.*
Extended European Search Report from corresponding European application EP12847869.0 dated Dec. 8, 2014.
International Search Report and Written Opinion from corresponding PCT application PCT/US2012/064393 dated Jan. 22, 2013.
Lin et al., "Synthesis and Structure-Activity Relationships of 5-Substituted Pyridine Analogues of 3-[2-((S)-Pyrrolidinyl)methoxy]pyridine, A-84543: A Potent Nicotinic Receptor Ligand," *Bioorg Med Chem Lett*, 11:631-633 (2001).
Liu et al., "Chemistry and Pharmacological Characterization of Novel Nitrogen Analogues of AMPO-H-OH (Sazetidine-A, 6-[5-(Azetidin-2-ylmethoxy)pyridin 3 yl]hex 5-yn-1-ol) as α4β2-Nicotinic Acetylcholine Receptor-Selective Partial Agonists," *J Med Chem*, 53:6973-6985 (2010).
Lubin et al., "Ultrastructural immunolocalization of the a7 nAChR subunit in guinea pig medial prefrontal cortex," Ann NY Acad Sci, 868: 628-632 (1999).
Plummer et al., "Expression of the α7 Nicotinic Acetylcholine Receptor in Human Lung Cells," Respiratory Research, 6: 29 (2005).

* cited by examiner

*Primary Examiner* — Patricia L Morris
(74) *Attorney, Agent, or Firm* — Foley Hoag LLP

(57) ABSTRACT

Disclosed are compounds and methods of using them to treat a disorder selected from the group consisting of addiction, pain, obesity, schizophrenia, epilepsy, mania and manic depression, anxiety, Alzheimer's disease, learning deficit, cognition deficit, attention deficit, memory loss, Lewy Body Dementia, Attention Deficit Hyperactivity Disorder (ADHD), Parkinson's disease, Huntington's disease, Tourette's syndrome, amyotrophic lateral sclerosis, inflammation, stroke, spinal cord injury, dyskinesias, obsessive compulsive disorder, chemical substance abuse, alcoholism, memory deficit, pseudodementia, Ganser's syndrome, migraine pain, bulimia, premenstrual syndrome or late luteal phase syndrome, tobacco abuse, post-traumatic syndrome, social phobia, chronic fatigue syndrome, premature ejaculation, erectile difficulty, anorexia nervosa, autism, mutism, trichotillomania, hypothermia, and disorders of sleep.

19 Claims, 21 Drawing Sheets

Scheme 1:

Method B:

Reagents and Conditions: f) 4 mol% Pd(PPh$_3$)$_2$Cl$_2$, 8 mol% PPh$_3$, 8 mol% CUI, iPr$_2$NH, toluene, 80 °C, 18 h g) KOH, MeOH/H$_2$O (4:1), 25 °C, 3 h h) Substituted Aryl Iodides, 25 °C, 16 h or Substituted Aryl Bromide (VMY-2-137), 80 °C, 16 h. i) TFA, CH$_2$Cl$_2$, 0 °C to r.t., 4-6 h then 2 M NaOH, MeOH/H$_2$O (9:1), MeOH, 18 h.

Scheme 1:
Method C:

Reagents and Conditions: a) DEAD, PPh$_3$, THF, 0 °C, 48 h b) 4 mol% Pd(PPh$_3$)$_2$Cl$_2$, 8 mol% PPh$_3$, 8 mol% CuI, iPr$_2$NH, toluene, 80 °C, 18 h c) KOH, MeOH/H$_2$O (20:1), 25 °C, 3 h d) 4 mol% Pd(PPh$_3$)$_2$Cl$_2$, 8 mol% PPh$_3$, 8 mol% CuI, iPr$_2$NH, toluene, 25 °C, 18 h e) TFA, CH$_2$Cl$_2$, 0 °C to r.t., 4-6 h then 2M NaOH, MeOH/H$_2$O (9:1), MeOH, 18 h.

Scheme 2:
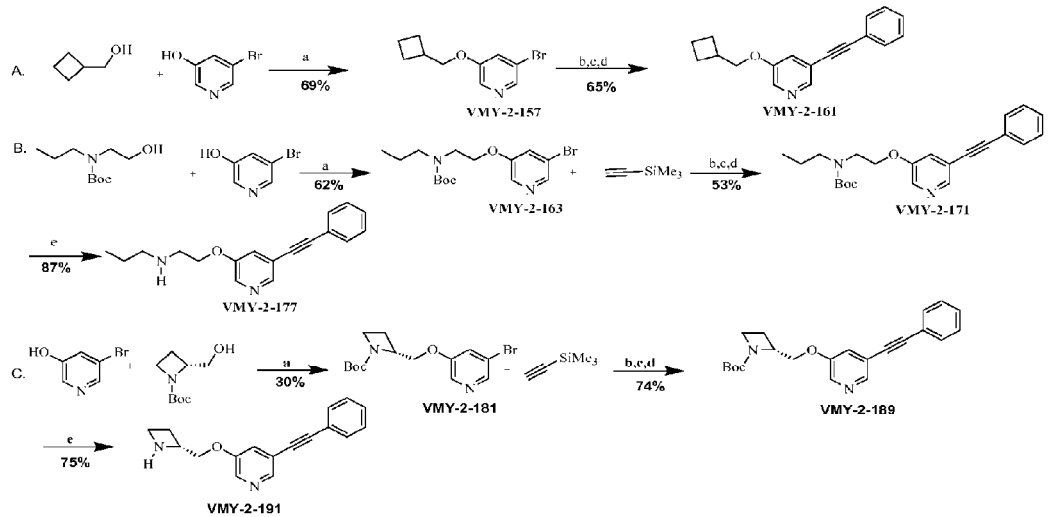
Reagents and Conditions: a) DEAD, PPh₃, THF, 0 °C, 48 h b) 4 mol% Pd(PPh₃)₂Cl₂, 8 mol% PPh₃, 8 mol% CuI, iPr₂NH, toluene, 80 °C, 18 h C) KOH, MeOH/H₂O(4:1), 25 °C, 3 h d) Iodobenzene, 25 °C, 16 h e) TFA, CH₂Cl₂, 0 °C-r.t 4-6h then 2M NaOH Methanol in Water (9:1), Methanol, 18 h.
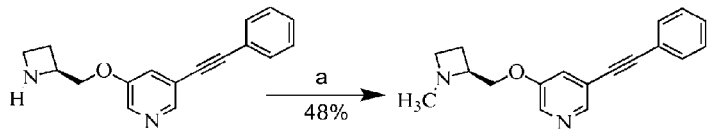
a) HCHO, NaCNBH₃, pH 4-5 (CH₃COOH;CH₃COONa), Ethanol
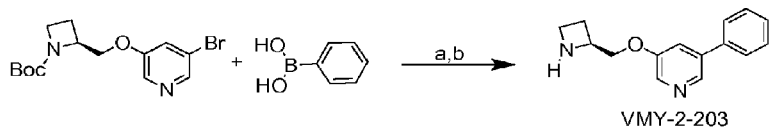
a) Pd(PPh₃)₄, 2 M Na₂CO₃, toluene:ethanol (3:1), 90 °C, 18 h. b) TFA, CH₂Cl₂, 0 °C to r.t., 6 h, then 2 M NaOH, MeOH/H₂O (9:1), MeOH, 18 h.
FIG. 3

Scheme 3:

a) HCHO, NaCNBH$_3$, PH=4-5 (CH$_3$COOH;CH$_3$COONa), Ethanol

A.
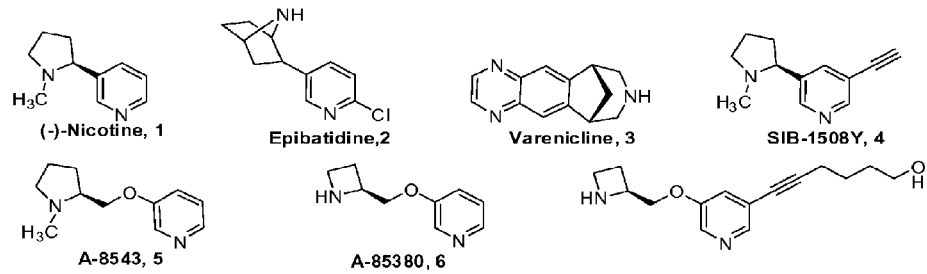
B.
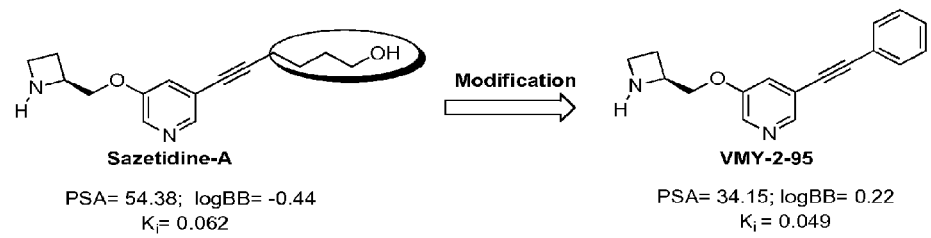
C.
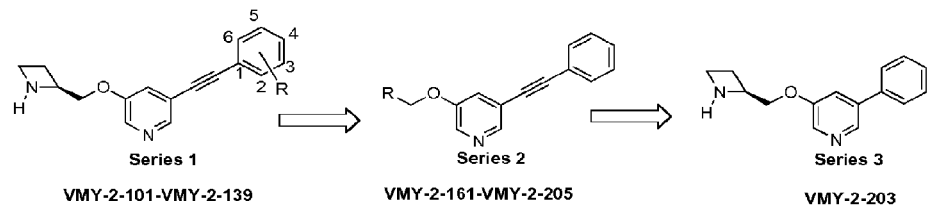
FIG. 7

| S.No | Compound Name | In vitro rat brain tissue binding 4h, 5µM, fU$_{brain}$ (%) | | Mean fU brain (%) |
|---|---|---|---|---|
| | | Rep A | Rep B | |
| 1 | Haloperidol | 1.60 | - | 1.60 |
| 2 | Varenicline | 84.5 | 94.9 | 89.7 ± 7.4 |
| 3 | Sazetidine A | 68.7 | 50.9 | 59.8 ± 12.6 |
| 4 | VMY-2-95 | 1.07 | 1.34 | 1.21 ± 0.2 |

| S.No | Compound ID | In vitro rat brain tissue binding 4h, 5µM, fU$_{brain}$ (%) | | Mean fU brain (%) |
|---|---|---|---|---|
| | | Rep A | Rep B | |
| 1 | Propranolol | 9.61 | - | 9.61 |
| 2 | Varenicline | 65.7 | 76.1 | 70.9 ± 7.4 |
| 3 | Sazetidine A | 72.5 | 77.7 | 75.1 ± 3.7 |
| 4 | VMY-2-95 | 7.16 | 9.65 | 8.40 ± 1.8 |

| S.No | Compound ID | Unbound fraction | | B/P=fUPlasma/fUBrain |
|---|---|---|---|---|
| | | Plasma | Brain | |
| 1 | Varenicline | 70.9 | 89.7 | 0.79 |
| 2 | Sazetidine A | 75.1 | 59.8 | 1.25 |
| 3 | VMY-2-95 | 8.40 | 1.21 | 6.94 |

| Comp ID | $K_i$ (nM)[b] | | | | | | | | $\alpha3\beta4/\alpha4\beta2$ |
|---|---|---|---|---|---|---|---|---|---|
| | $\alpha2\beta2$ | $\alpha2\beta4$ | $\alpha3\beta2$ | $\alpha3\beta4$ | $\alpha4\beta2$ | $\alpha4\beta4$ | $\alpha7$ | forebrain | |
| 95 | 0.11 | 58 | 0.53 | 640 | 0.049 | 11 | 580 | 0.57 | 13,000 |
| 101 | 0.045 | 37 | 0.41 | 650 | 0.083 | 7.2 | 2,000 | 0.50 | 7,800 |
| 105 | 0.081 | 47 | 0.61 | 580 | 0.072 | 8.7 | 1100 | 0.56 | 8,100 |
| 109 | 0.029 | 31 | 0.19 | 520 | 0.032 | 5.3 | 720 | 0.44 | 16,000 |
| 113 | 0.063 | 23 | 0.52 | 1400 | 0.050 | 4.7 | 1,800 | 0.73 | 28,000 |
| 117 | 0.26 | 54 | 1.4 | 1,400 | 0.26 | 11 | 1,300 | 3.5 | 5,400 |
| 123 | 0.053 | 46 | 0.34 | 4,000 | 0.046 | 12 | 200 | 1.1 | 87,000 |
| 127 | 0.19 | 150 | 1.6 | 3,400 | 0.093 | 17 | 460 | 1.7 | 37,000 |
| 131 | 0.053 | 66 | 0.46 | 1,000 | 0.031 | 12 | 250 | 0.70 | 32,000 |
| 135 | 0.064 | 38 | 0.24 | 1,100 | 0.043 | 8.1 | 590 | 1.4 | 26,000 |

| Comp ID | $K_i$ (nM)[b] | | | | | | | | $\alpha3\beta4/\alpha4\beta2$ |
|---|---|---|---|---|---|---|---|---|---|
| | $\alpha2\beta2$ | $\alpha2\beta4$ | $\alpha3\beta2$ | $\alpha3\beta4$ | $\alpha4\beta2$ | $\alpha4\beta4$ | $\alpha7$ | forebrain | |
| 139 | 0.091 | 53 | 0.59 | 1,300 | 0.076 | 10 | 1,500 | 1.7 | 17,000 |
| Saz-A | 0.087 | 210 | 0.38 | 1,900 | 0.062 | 52 | 668 | 0.17 | 31,000 |
| Nicotine[c] | 12 | 110 | 47 | 440 | 10 | 40 | 517 | 12 | 44 |
| Varenicline | 0.48 | 94 | 2.5 | 390 | 0.12 | 28 | 37 | 1.1 | 3,300 |

[a] Competition binding assays were carried out in membrane homogenates of stably transfected cells or rat forebrain tissue as described previously (Xiao et al., 2009; Xiao and Kellar, 2004; Xiao et al., 1998). The rat nAChRs were labeled with [$^3$H]-epibatidine. The $K_d$ values for [$^3$H]-epibatidine used for calculating $K_i$ values were 0.02 for $\alpha2\beta2$, 0.08 for $\alpha2\beta4$, 0.03 for $\alpha3\beta2$, 0.3 for $\alpha3\beta4$, 0.04 for $\alpha4\beta2$, 0.09 for $\alpha4\beta4$, 1.8 for $\alpha7$ and 0.05 for rat forebrain. [b] $K_i$ values of the compounds shown are the mean of 3 to 5 independent measurements. For clarity, the SEM for values are omitted. [c] The Ki values of (-)-nicotine was published previously (J.Pharmacol. Exp. Therapy. 2004, 310, 98-107).

FIG. 15

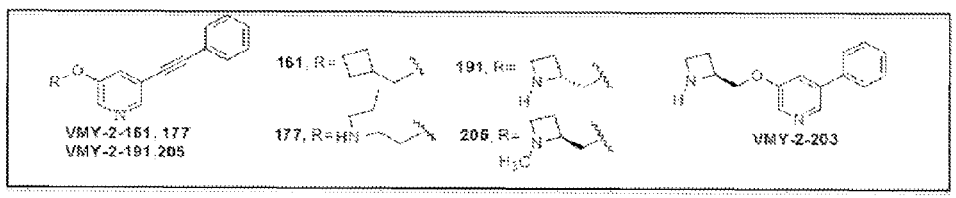

| Comp ID | $K_i^b$ | | | | | | | | α3β4/α4β2 |
|---|---|---|---|---|---|---|---|---|---|
| | α2β2 | α2β4 | α3β2 | α3β4 | α4β2 | α4β4 | α7 | forebrain | |
| 161 | 290000 | 61000 | 32000 | 1300000 | 160,000 | 710000 | 410000 | 150000 | 8 |
| 177 | 7300 | 280000 | 18000 | 850,000 | 1100 | 68000 | 48000 | 50000 | 770 |
| 191 | 0.19 | 46 | 0.92 | 1700 | 0.11 | 8.9 | 1600 | 1.1 | 15,000 |
| 203 | 0.22 | 36 | 5.0 | 1300 | 0.14 | 6.2 | 17000 | 1.1 | 9285 |
| 205 | 2.9 | 4100 | 26 | 40000 | 1.2 | 1100 | 7700 | 30 | 33,000 |

[a] Competition binding assays were carried out in membrane homogenates of stably transfected cells or rat forebrain tissue as described previously (Xiao et al., 2009; Xiao and Kellar, 2004; Xiao et al., 1998). The rat nAChRs were labeled with [$^3$H]-epibatidine. The $K_d$ values for [$^3$H]-epibatidine used for calculating $K_i$ values were 0.02 for α2β2, 0.08 for α2β4, 0.03 for α3β2, 0.3 for α3β4, 0.04 for α4β2, 0.09 for α4β4, 1.8 for α7 and 0.05 for rat forebrain. [b] $K_i$ values of the compounds shown are the mean of three independent measurements. For clarity, the SEM for values are omitted.

FIG. 16

| Compound | α4β2 nAChRs[a] | | | α3β4 nAChRs[a] | | |
|---|---|---|---|---|---|---|
| | $EC_{50}$[b] (nM) | $E_{max}$[c] (%) | $IC_{50(10')}$[d] (nM) | $EC_{50}$ (nM) | $E_{max}$ (%) | $IC_{50(10')}$ (nM) |
| VMY-2-95 | 8.6 | 26 | 16 | ND[e] | ND | >10,000 |
| Sazetidine-A | 24 | 40 | 12 | ND | ND | >10,000 |
| Varenicline | 950 | 45 | 94 | 29,000 | 85 | >10,000 |
| (-)-Nicotine | 2,400 | 100 | 370 | 34,000 | 100 | >10,000 |

[a] Functional properties of each compounds were determined in using stable cell lines expressing human α4β2 or rat α3β4 nAChRs. [b] $EC_{50}$ values show potencies of agonist activities. [c] $E_{max}$ values show relative efficacies of agonist activities, which were normalized to the $E_{max}$ value of nicotine. [d] $IC_{50(10\ min)}$ values show potencies of desensitizer activities, which were determined by pre-incubated cells with various concentrations of test compounds for 10 min then exposed to 100 μM nicotine. [d] ND indicates no stimulation was detected. All values shown are means of 3 to 9 independent experiments. For clarity, the SEM for values are omitted.

FIG. 17

| Inhibition of binding by VMY-2-95 at other targets[a] | % Inhibition |
|---|---|
| Serotonin, 5-HT$_{1A}$ | 9.7 |
| Serotonin, 5-HT$_{1B}$ | 92 |
| Serotonin, 5-HT$_{1D}$ | 11 |
| Serotonin, 5-HT$_{1E}$ | 3 |
| Serotonin, 5-HT$_{2A}$ | 85 |
| Serotonin, 5-HT$_{2B}$ | 44 |
| Serotonin, 5-HT$_{2C}$ | 64 |
| Serotonin, 5-HT$_3$ | 35 |
| Serotonin, 5-HT$_{5a}$ | 3 |
| Serotonin, 5-HT$_6$ | 1 |
| Serotonin, 5-HT$_7$ | 38 |
| Muscarinic, M1 | 18.5 |
| Muscarinic, M2 | 16 |
| Muscarinic, M3 | 39 |
| Muscarinic, M4 | -14[b] |
| Muscarinic, M5 | 42 |
| Sigma, σ1 | 81 |
| Sigma, σ2 | 78 |
| Dopaminergic, D1 | 52 |
| Dopaminergic, D2 | 8.1 |
| Dopaminergic, D3 | 3.2 |
| Dopaminergic, D4 | 24 |
| Dopaminergic, D5 | 27 |
| Transporters, DAT | 84 |
| Transporters, NET | 69 |
| Transporters, SERT | 57 |
| GABA$_A$ R, GABA$_A$ | 0.3 |
| Histamine, H1 | 13.3 |
| Histamine, H2 | 6.8 |
| Opioid , DOR | 11.1 |
| Opioid , KOR | 55 |
| Opioid , MOR | -0.8 |
| Benzodiazepine, BZP | 0.6 |
| Adrenergic, α1A | 14 |
| Adrenergic, α1B | 26 |
| Adrenergic, α1D | 19 |
| Adrenergic, α2A | 34 |
| Adrenergic, α2B | 46 |
| Adrenergic, α2C | 66 |
| Adrenergic, β1 | 10 |
| Adrenergic, β3 | 12 |

FIG. 18

| Target[a] | Ki (nM) of VMY-2-95 | Ratio of Ki Values (α4β2 nAChRs/other target) |
|---|---|---|
| Nicotinic, α4β2 | 0.049 | 1 |
| Serotonin, 5-HT$_{1B}$ | >10,000 | >200,000 |
| Serotonin, 5-HT$_{1A}$ | 158 | 3,200 |
| Serotonin, 5-HT$_{1C}$ | 285 | 5,800 |
| Adrenergic, α2C | >10,000 | >200,000 |
| Dopaminergic, D1 | >10,000 | >200,000 |
| Dopamine Active Transport (DAT) | ND | --- |
| Norepinephrine transporter (NET) | 2,600 | 53,000 |
| Serotonin transporter (SERT) | 3,400 | 68,000 |
| Sigma, σ2 | 490,000 | >200,000 |
| Opioid, KOR | >10,000 | >200,000 |

[a] $K_i$ (nM) values were obtained from non-linear regression of radioligand competition binding isotherms. [b] ND indicates on detectable binding was observed.

FIG. 19

| Compound ID | Binding Affinity Ki (nM) | Ligand Efficiency Kcal/mole | Predicted Psychochemical properties | | | |
|---|---|---|---|---|---|---|
| | $\alpha4\beta2$ | LE[a] | MW[b] | cLogP[b] | PSA[c] | log BB[d] |
| 95 | 0.049 | 0.70 | 264.32 | 3.712 | 34.15 | 0.2 |
| 101 | 0.083 | 0.65 | 282.31 | 3.855 | 34.15 | 0.22 |
| 105 | 0.072 | 0.66 | 282.31 | 3.855 | 34.15 | 0.22 |
| 109 | 0.032 | 0.68 | 282.31 | 3.855 | 34.15 | 0.22 |
| 113 | 0.050 | 0.64 | 300.30 | 3.998 | 34.15 | 0.24 |
| 117 | 0.26 | 0.54 | 332.32 | 4.595 | 34.15 | 0.33 |
| 123 | 0.046 | 0.67 | 278.35 | 4.211 | 34.15 | 0.27 |
| 127 | 0.093 | 0.65 | 298.77 | 4.425 | 34.15 | 0.30 |
| 131 | 0.031 | 0.60 | 325.38 | 4.191 | 37.39 | 0.22 |
| 135 | 0.043 | 0.64 | 296.34 | 4.354 | 34.15 | 0.29 |
| 139 | 0.076 | 0.60 | 312.34 | 3.914 | 43.38 | 0.1 |
| Saz-A | 0.062 | 0.73 | 260.33 | 1.47 | 54.38 | -0.44 |
| Varenecline | 0.12 | 0.85 | 211.26 | 0.899 | 37.81 | -0.28 |
| Nicotine | 10 | 1.14 | 163.24 | 1.11 | 17.33 | 0.05 |

[a] Ligand binding efficiency was calculated according to the Hopkinns equation: $LE = 1.372 * (-\log K_i (Moles))/ N$, [b] Molecular weight and cLogP were calculated using ChemBiodraw Ultra 11.0, [c] Polar Surface Area (PSA) was calculated using www.chemicalize.org, [d] Log BB was calculated from the following equation: $Log\ BB = -0.0148 PSA + 0.132 cLogP + 0.139$

FIG. 20

| Compound ID | Molecular Formula | CHN Data |
|---|---|---|
| VMY-2-95 | $C_{17}H_{16}N_2O$ | Theor: C, 77.25; H, 6.10; N, 10.60<br>Exper: C, 77.22; H, 6.13; N, 10.51 |
| VMY-2-101 | $C_{17}H_{15}FN_2O \cdot 0.1H_2O$ | Theor: C, 71.63; H, 5.41; N, 9.82<br>Exper: C, 71.21; H, 5.41; N, 9.76 |
| VMY-2-105 | $C_{17}H_{15}FN_2O$ | Theor: C, 72.32; H, 5.36; N, 9.92<br>Exper: C, 71.82; H, 5.38; N, 9.77 |
| VMY-2-109 | $C_{17}H_{15}FN_2O$ | Theor: C, 72.32; H, 5.36; N, 9.92<br>Exper: C, 72.03; H, 5.46; N, 9.78 |
| VMY-2-113 | $C_{17}H_{14}F_2N_2O \cdot 0.06H_2O$ | Theor: C, 67.74; H, 4.72; N, 9.28<br>Exper: C, 67.35; H, 4.68; N, 9.10 |
| VMY-2-117 | $C_{18}H_{15}F_3N_2O$ | Theor: C, 65.06; H, 4.55; N, 8.43<br>Exper: C, 64.74; H, 4.45; N, 8.30 |
| VMY-2-123 | $C_{18}H_{18}N_2O \cdot 0.06CH_2Cl_2$ | Theor: C, 76.19; H, 6.60; N, 9.87<br>Exper: C, 75.84; H, 6.34; N, 9.75 |
| VMY-2-127 | $C_{17}H_{15}ClN_2O \cdot 0.06H_2O$ | Theor: C, 67.84; H, 5.04; N, 9.30<br>Exper: C, 67.70; H, 5.03; N, 9.11 |
| VMY-2-135 | $C_{18}H_{17}FN_2O \cdot 0.04H_2O$ | Theor: C, 72.59; H, 5.76; N, 9.40<br>Exper: C, 70.86; H, 5.72; N, 9.01 |
| VMY-2-139 | $C_{18}H_{17}FN_2O_2 \cdot 0.04H_2O$ | Theor: C, 68.89; H, 5.47; N, 8.92<br>Exper: C, 67.51; H, 5.51; N, 8.60 |
| VMY-2-161 | $C_{18}H_{17}NO$ | Theor: C, 82.10; H, 6.51; N, 5.32<br>Exper: C, 81.94; H, 6.44; N, 5.31 |
| VMY-2-177 | $C_{18}H_{20}N_2O$ | Theor: C, 77.11; H, 7.19; N, 9.99<br>Exper: C, 76.81; H, 7.12; N, 9.84 |
| VMY-2-191 | $C_{17}H_{16}N_2O \cdot 0.6H_2O$ | Theor: C, 74.21; H, 6.30; N, 10.18<br>Exper: C, 74.50; H, 6.20; N, 10.07 |
| VMY-2-203 | $C_{15}H_{18}N_2O \cdot 0.6H_2O$ | Theor: C, 71.74; H, 6.90; N, 11.15<br>Exper: C, 71.73; H, 6.76; N, 10.88 |

Note: Based on the CHN data, we assumed that traces of water molecules still accompanying with some of the compounds discussed in this report. The reason adding the water molecule was that in the reaction settings we have employed the 2 N NaOH (9:1 methanol/Water) washing condition to remove the TFA salt from the final compounds. In addition, we have used $CH_2Cl_2$/ Methanol/$NH_4OH$ conditions to purify the final compounds.

FIG. 21

PHENYL-SUBSTITUTED NICOTINIC LIGANDS, AND METHODS OF USE THEREOF

RELATED APPLICATIONS

This application is a continuation of U.S. patent application Ser. No. 14/357,701, filed May 12, 2014, which is the U.S. national phase of International Patent Application No. PCT/US2012/064393, filed Nov. 9, 2012, which claims the benefit of priority to U.S. Provisional Patent Application Ser. No. 61/647,223, filed May 15, 2012; and U.S. Provisional Patent Application Ser. No. 61/558,812, filed Nov. 11, 2011.

GOVERNMENT SUPPORT

This invention was made with government support under grant numbers DA027990 and R03DA025947 awarded by the National Institutes of Health. The government has certain rights in the invention.

BACKGROUND OF THE INVENTION

Neuronal nicotinic acetylcholine receptors (nAChRs) serve a wide range of physiological functions and have been implicated in a number of pathological processes and pharmacological effects of nicotinic drugs. Many of the important in vivo effects of nicotine in the central nervous system (CNS) are mediated mainly by the desensitization of nAChRs, specifically α4β2 nAChRs, which are the major nAChR subtype in the CNS and the one most clearly affected (up-regulated) by chronic administration of nicotine in rats and mice and by smoking in humans.

Sazetidine-A (Saz-A) is a recently reported new nAChR ligand that is a selective α4β2 nAChR desensitizer. U.S. Pat. No. 8,030,300 (incorporated by reference). Its major in vitro effect is to desensitize α4β2 nAChRs without affecting either α3β4 or α7 nAChRs. Saz-A shows strong in vivo effects in animal models, including analgesia, reduction in nicotine self-administration, reduction in alcohol intake, antidepressant-like activity, and reversal of attentional impairment.

SUMMARY OF THE INVENTION

Developing novel compounds to target the nicotinic acetylcholine receptors containing α4 and β2 subunits with desensitization effects could provide new effective treatments for nicotinic addiction. The present invention is a new class of nAChR ligands that displays high selectivity and picomolar binding affinity for α4β2 nicotinic receptors. Among the novel compounds, 11 high affinity compounds competed for [$^3$H]-epibatidine binding at α4β2 receptors with $K_i$ values in the range of 0.031-0.26 nM. These compounds also have other medicinal and pharmacological properties that should make them good candidates as CNS drugs. The selected lead compound, VMY-2-95, binds with high affinity and potently desensitizes α4β2 receptors. At a dose of 3 mg/kg, VMY-2-95 significantly reduced nicotine self-administration in rats. The results support further characterization of VMY-2-95 and its analogs in animal models for developing new therapeutics to treat nicotine addiction.

Compounds of the invention may be useful in treating a mammal suffering from aging, addiction, pain, obesity, schizophrenia, epilepsy, mania and manic depression, anxiety, Alzheimer's disease, learning deficit, cognition deficit, attention deficit, memory loss, Lewy Body Dementia, Attention Deficit Hyperactivity Disorder (ADHD), Parkinson's disease, Huntington's disease, Tourette's syndrome, amyotrophic lateral sclerosis, inflammation, stroke, spinal cord injury, dyskinesias, obsessive compulsive disorder, chemical substance abuse, alcoholism, memory deficit, pseudodementia, Ganser's syndrome, migraine pain, bulimia, premenstrual syndrome or late luteal phase syndrome, tobacco abuse, post-traumatic syndrome, social phobia, chronic fatigue syndrome, premature ejaculation, erectile difficulty, anorexia nervosa, autism, mutism, trichtillomania, hypothermia, or disorders of sleep; or in improving cognitive functions and attention.

An aspect of the invention is a compound of formula (I) or a pharmaceutically acceptable salt thereof

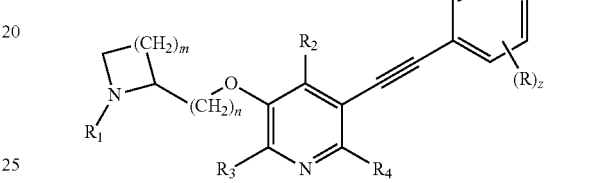

wherein:
R represents, independently for each occurrence, halogen, C1-C6 alkyl, allyl, C1-C6 alkyloxy, amino, hydroxyl, nitro, cyano, or trifluoro-C1-C4 alkyl;
$R_1$ represents hydrogen, C1-C6 alkyl, allyl, or C3-C6 cycloalkyl;
$R_2$, $R_3$, and $R_4$ independently represent hydrogen, C1-C6 alkyl, allyl, or C3-C6 cycloalkyl, or C1-C6 alkyl substituted with at least one fluorine;
m is an integer ranging from 1 to 3;
n is an integer selected from 1 and 2; and
z is an integer ranging from 0 to 5;
with the proviso that the compound of formula (I) is not

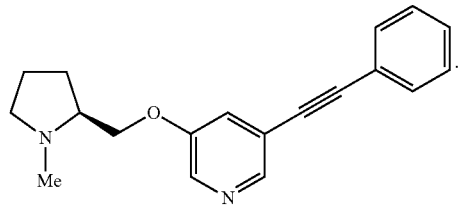 [SMILES: CN1CCC[C@H]1COc1cncc(C#Cc2ccccc2)c1]

In one embodiment, m is 1.
In one embodiment n is 1.
In one embodiment, z is 0.
In one embodiment, z is 1.
In one embodiment, z is 2.
In one embodiment R represents, independently for each occurrence, halogen, C1-C6 alkyl, C1-C6 alkyloxy, amino, or trifluoro-C1-C4 alkyl.
In one embodiment R represents, independently for each occurrence, halogen, methyl, methoxy, amino, or trifluoromethyl.
In one embodiment $R_1$ is C1-C6 alkyl.
In one embodiment $R_1$ is methyl.
In one embodiment $R_1$ is hydrogen.
In one embodiment $R_2$, $R_3$, and $R_4$ independently represent hydrogen.

In one embodiment the compound is
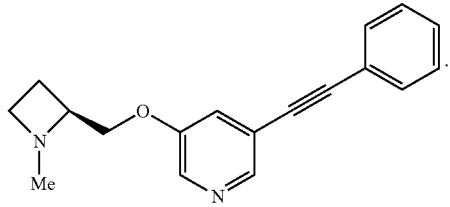 [SMILES: CN1CC[C@H]1COc1cncc(C#Cc2ccccc2)c1]
In one embodiment the compound is selected from the group consisting of:
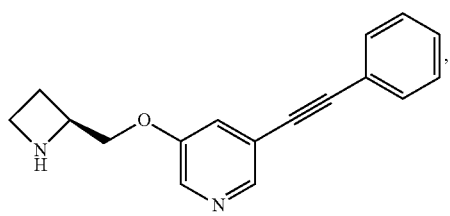
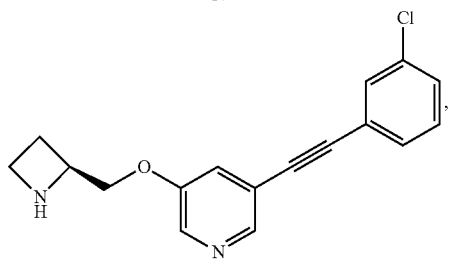
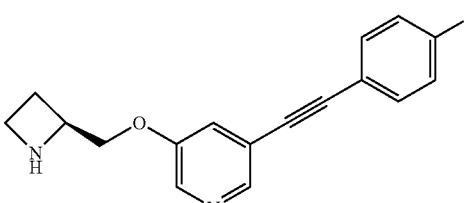
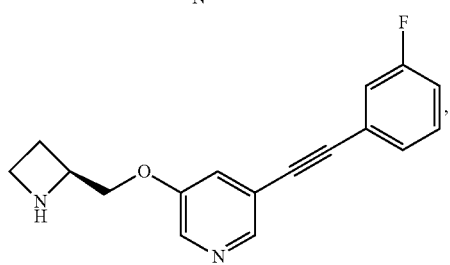
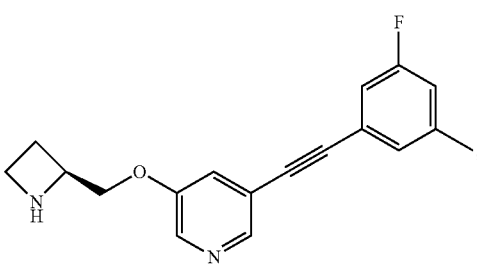
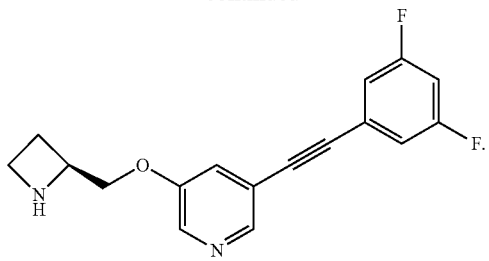
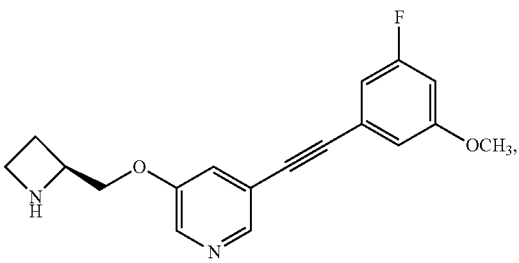
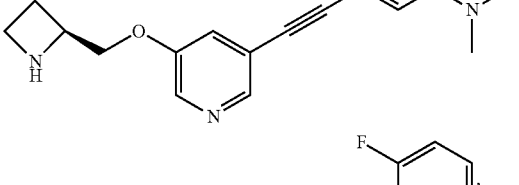
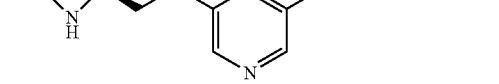
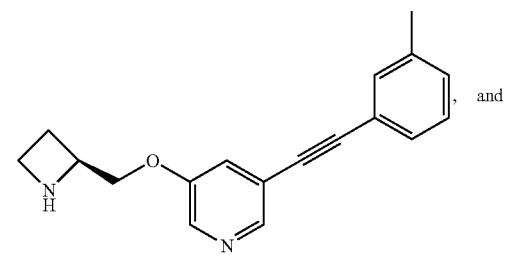
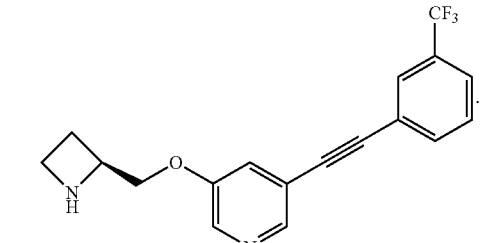
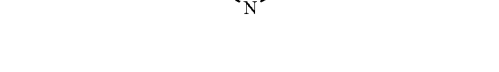
An aspect of the invention is a compound of formula (II) or a pharmaceutically acceptable salt thereof

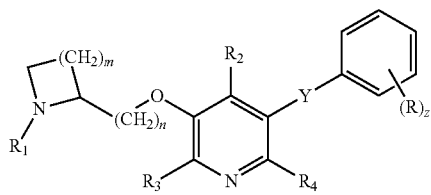

(II)

wherein:
R represents, independently for each occurrence, halogen, C1-C6 alkyl, allyl, C1-C6 alkyloxy, amino, hydroxyl, nitro, cyano, or trifluoro-C1-C4 alkyl;
$R_1$ represents hydrogen, C1-C6 alkyl, allyl, or C3-C6 cycloalkyl;
$R_2$, $R_3$, and $R_4$ independently represent hydrogen, C1-C6 alkyl, allyl, or C3-C6 cycloalkyl, or C1-C6 alkyl substituted with at least one fluorine;
Y is O, S, or N($R^C$);
$R^C$ is hydrogen, C1-C6 alkyl, or allyloxycarbonyl;
m is an integer ranging from 1 to 3;
n is an integer selected from 1 and 2; and
z is an integer ranging from 0 to 5.
 In one embodiment m is 1.
 In one embodiment n is 1.
 In one embodiment, z is 0.
 In one embodiment, z is 1.
 In one embodiment, z is 2.
 In one embodiment R represents, independently for each occurrence, halogen, C1-C6 alkyl, C1-C6 alkyloxy, amino, or trifluoro-C1-C4 alkyl.
 In one embodiment R represents, independently for each occurrence, halogen, methyl, methoxy, amino, or trifluoromethyl.
 In one embodiment $R_1$ is C1-C6 alkyl.
 In one embodiment $R_1$ is methyl.
 In one embodiment $R_1$ is hydrogen.
 In one embodiment $R_2$, $R_3$, and $R_4$ independently represent hydrogen.

An aspect of the invention is a compound of formula (III) or a pharmaceutically acceptable salt thereof

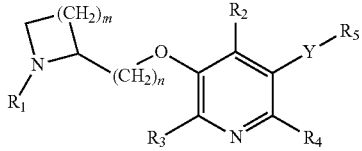

(III)

wherein:
$R_1$ represents hydrogen, C1-C6 alkyl, allyl, or C3-C6 cycloalkyl; $R_2$, $R_3$, and $R_4$ independently represent hydrogen, C1-C6 alkyl, allyl, or C3-C6 cycloalkyl, or C1-C6 alkyl substituted with at least one fluorine;
$R_5$ represents

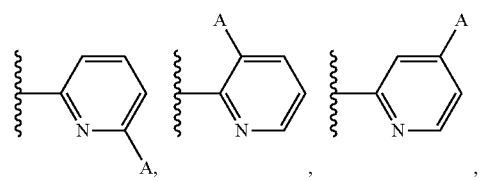

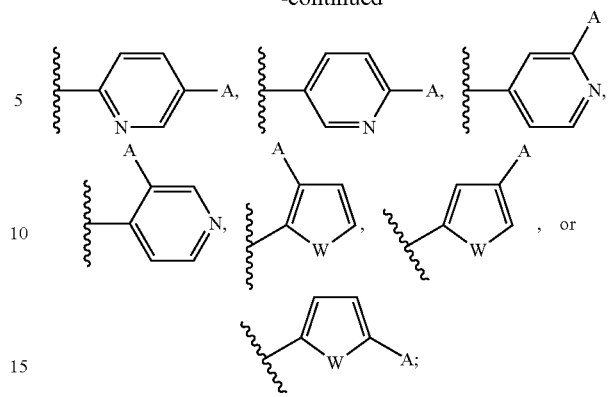

Y represents —C≡C— or O;
A represents hydrogen, halogen, methyl, C2-C6 alkyl, methoxy, hydroxy, amino, trifluoromethyl, isopropyl, or t-butyl;
W represents O, S, or N($R^D$);
$R^D$ represents hydrogen, C1-C6 alkyl, or allyloxycarbonyl;
m is an integer ranging from 1 to 3; and
n is an integer selected from 1 and 2.
 In one embodiment m is 1.
 In one embodiment n is 1.
 In one embodiment $R_1$ is C1-C6 alkyl.
 In one embodiment $R_1$ is methyl.
 In one embodiment $R_1$ is hydrogen.
 In one embodiment $R_2$, $R_3$, and $R_4$ independently represent hydrogen.
 In one embodiment Y is —C≡C—.
 In one embodiment Y is O.

An aspect of the invention is a compound of formula (IV) or a pharmaceutically acceptable salt thereof

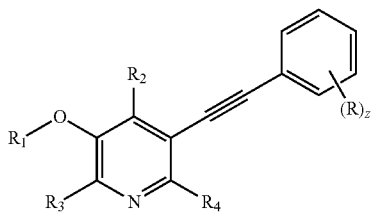

(IV)

wherein:
R represents, independently for each occurrence, halogen, C1-C6 alkyl, allyl, C1-C6 alkyloxy, amino, hydroxyl, nitro, cyano, or trifluoro-C1-C4 alkyl;
$R_1$ represents

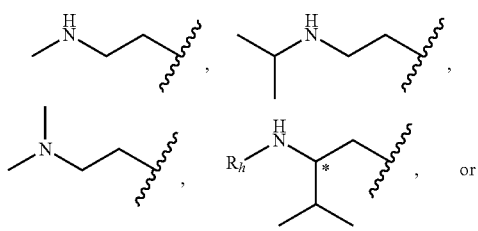

-continued

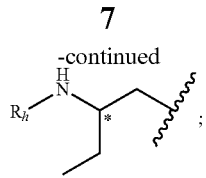

$R_2$, $R_3$, and $R_4$ independently represent hydrogen, C1-C6 alkyl, allyl, or C3-C6 cycloalkyl, or C1-C6 alkyl substituted with at least one fluorine;
$R_h$ represents C1-C6 alkyl, C3-C6 cycloalkyl, aryl, or C1-C6 alkyl substituted with at least one fluorine;
m is an integer ranging from 1 to 3; and
n is an integer selected from 1 and 2; and
z is an integer ranging from 0 to 5.

In one embodiment m is 1.
In one embodiment n is 1.
In one embodiment, z is 0.
In one embodiment, z is 1.
In one embodiment, z is 2.
In one embodiment R represents, independently for each occurrence, halogen, C1-C6 alkyl, C1-C6 alkyloxy, amino, or trifluoro-C1-C4 alkyl.
In one embodiment R represents, independently for each occurrence, halogen, methyl, methoxy, amino, or trifluoromethyl.
In one embodiment $R_2$, $R_3$, and $R_4$ independently represent hydrogen.

An aspect of the invention is a compound of formula (V) or a pharmaceutically acceptable salt thereof

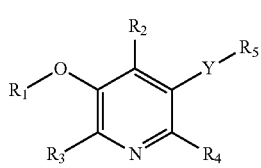

(V)

wherein:
$R_1$ represents

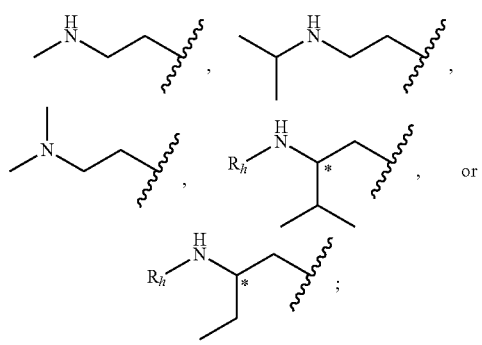

$R_2$, $R_3$, and $R_4$ independently represent hydrogen, C1-C6 alkyl, allyl, or C3-C6 cycloalkyl, or C1-C6 alkyl substituted with at least one fluorine;
$R_h$ represents C1-C6 alkyl, C3-C6 cycloalkyl, aryl, or C1-C6 alkyl substituted with at least one fluorine;

$R_5$ represents

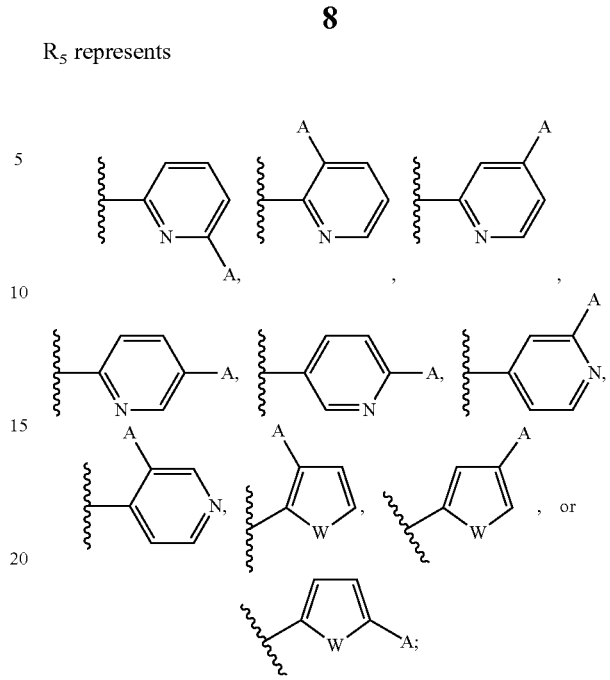

Y represents —C≡C— or O;
A represents hydrogen, halogen, methyl, C2-C6 alkyl, methoxy, hydroxy, amino, trifluoromethyl, isopropyl, or t-butyl;
W represents O, S, or N($R^D$);
$R^D$ represents hydrogen, C1-C6 alkyl, or allyloxycarbonyl;
m is an integer ranging from 1 to 3; and
n is an integer selected from 1 and 2.

In one embodiment m is 1.
In one embodiment n is 1.
In one embodiment $R_2$, $R_3$, and $R_4$ independently represent hydrogen.

An aspect of the invention is a pharmaceutical composition, comprising a compound of the invention; and a pharmaceutically acceptable carrier.

An aspect of the invention is a method of treating a disorder selected from the group consisting of addiction, pain, obesity, schizophrenia, epilepsy, mania and manic depression, anxiety, Alzheimer's disease, learning deficit, cognition deficit, attention deficit, memory loss, Lewy Body Dementia, Attention Deficit Hyperactivity Disorder (ADHD), Parkinson's disease, Huntington's disease, Tourette's syndrome, amyotrophic lateral sclerosis, inflammation, stroke, spinal cord injury, dyskinesias, obsessive compulsive disorder, chemical substance abuse, alcoholism, memory deficit, pseudodementia, Ganser's syndrome, migraine pain, bulimia, premenstrual syndrome or late luteal phase syndrome, tobacco abuse, post-traumatic syndrome, social phobia, chronic fatigue syndrome, premature ejaculation, erectile difficulty, anorexia nervosa, autism, mutism, trichotillomania, hypothermia, and disorders of sleep. The method comprises the step of administering to a subject in need thereof a therapeutically effective amount of a compound of the invention. In one embodiment the disorder is addiction.

BRIEF DESCRIPTION OF THE DRAWINGS

FIG. 3 depicts Scheme 2 for synthesis of certain indicated compounds of the invention.

FIG. 7 A shows selected natural and synthetic nAChR ligands. B shows design strategy for VMY-2-95. C shows the general structures of the present series of compounds.

FIG. 15 continues the data presented in FIG. 14.

FIG. 16 shows binding affinities of series 2 compounds for rat nAChR subtypes.

FIG. 17 shows the activation and inhibition of nAChR function by VMY-2-95, Saz-A, varenicline and nicotine.

FIG. 18 shows the inhibition of binding by VMY-2-95 at other targets. $^a$The tested default concentration of VMY-2-95 for the primary binding assays is 10 μM. For each receptor, the value represents mean of replicates. The inhibition data was generously provided by the National Institute of Mental Health; Psychoactive Drug Screening Program (NIMH PDSP). Significant inhibition is considered >50%. $^b$Negative inhibition represents a stimulation of binding.

FIG. 19 shows a comparison of the binding affinity (Ki) of VMY-2-95 for α4β2 nAChRs with those for other targets.

FIG. 20 shows calculated LE and physicochemical properties of compounds in series 1.

FIG. 21 shows CHN data for final compounds in series 1-3.

DETAILED DESCRIPTION OF THE INVENTION

Figure 1:
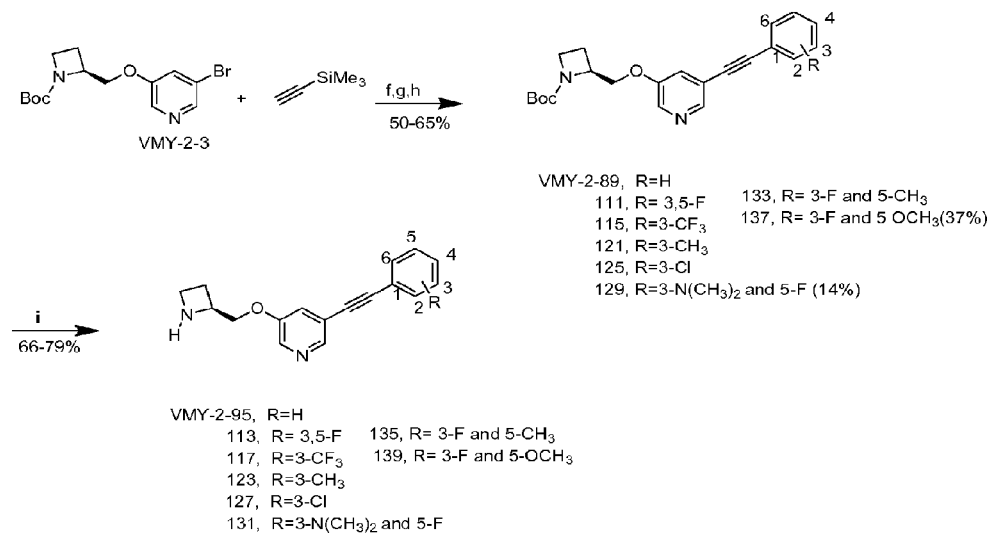
FIG. 1 depicts Scheme 1, Method B for synthesis of certain indicated compounds of the invention.

Nicotinic acetylcholine receptors (nAChRs) are pentameric ligand gated ion channels with significant potential as molecular targets for the design of drugs to treat a variety of central nervous system disorders. In vertebrates 12 neuronal nAChR subunits have been identified, including nine alpha subunits (α2-α10) and three beta subunits (β2-β4). These subunits may co-assemble as either heteromeric and homomeric pentameric receptors, forming a theoretically large array of receptor subtypes. The predominant nAChRs in the CNS are the heteromeric α4β2* subtype, composed of α4 and β2 (the * indicates that some of these nAChRs may contain one or more other subunits as well) and the homomeric α7 subtype. Certain areas of brain also contain a high density of α3β4* nAChRs, and this subtype appears to be the predominant nAChR in the autonomic nervous system.

Nicotine interacts with α4β2, α4β2α6* and α7 nAChRs in the dopaminergic mesolimbic pathway, which connects the ventral tegmental area of the midbrain and the limbic system via the nucleus accumbens, and these effects of nicotine on brain dopaminergic systems are important in reinforcing drug self-administration. The mesolimbic dopamine system is assumed to mediate the pleasurable and rewarding effects of most drugs of abuse, including nicotine. There is convincing evidence from extensive in vivo studies that mesolimbic α4β2* nAChRs play a pivotal role in the reinforcement effects of nicotine. Differential activation and desensitization of nAChR subtypes on dopamine and GABA neurons and possibly glutamate neurons result in stimulated dopamine release in the nucleus accumbens, leading to positive reinforcement of nicotine.

The α4β2 subtype of nAChR serves as an important target for treating nicotine addiction as well as several other important conditions, including anxiety, depression and cognitive disorders, and thus several groups have targeted these nicotinic receptors with a wide array of compounds to develop therapies. Many of the new compounds are structurally related to the natural nAChR ligands, including nicotine, epibatidine and cytisine (FIG. 7).

In 2006, varenicline (FIG. 7) emerged as the newest drug approved by the FDA as a therapeutic aid for smoking cessation. Clinical studies indicate that varenicline is the most effective drug currently available to help people quit smoking, but its effects may be temporary for most people. Furthermore, varenicline shows notable adverse side effects, limits the use of this compound as a therapy for smoking cessation.

We previously reported the synthesis and pharmacological properties of sazetidine-A (Saz-A) (FIG. 7), which potently and selectively desensitizes α2 containing nicotinic receptors, especially α4β2 nAChRs, as measured by whole cell currents and ion efflux assays. In animal models, Saz-A reduced nicotine self-administration, decreased alcohol intake and improved performance in tests of attention. Saz-A was also found to produce behaviors consistent with potential antidepressant and/or antianxiety effects in rats and mice. These promising in vivo results suggest saz-A is an excellent starting compound for developing additional potent and subtype-selective drugs that desensitize α4β2 nAChRs. Recent in vivo studies showed a low concentration of saz-A in rat brain, suggesting that optimization of saz-A physicochemical properties might enhance the in vivo CNS efficacy of this group of compounds.

Here, based on our studies of medicinal and pharmacological properties of Saz-A, we designed and synthesized a new line of novel nAChR ligands. In pharmacological studies, these compounds showed very promising properties that could lead to more effective treatments for nicotine addiction as well as other conditions that involve nAChRs.

DEFINITIONS

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "allyl" refers to a substituent with the structural formula $H_2C=CH-CH_2-$. The term "allyloxycarbonyl" (or "Alloc") refers to a common protecting group $H_2C=CH-CH_2-O-C(O)-$.

The term "aryl" as used herein includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $-CF_3$, $-CN$, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, azetidine, azepine, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The term "carbocycle", as used herein, refers to an aromatic or non-aromatic ring in which each atom of the ring is carbon.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

The terms "amine" and "amino" are art-recognized and refer to both unsubstituted and substituted amines, e.g., a moiety that can be represented by the general formula:

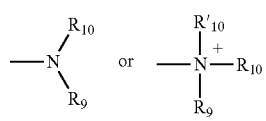

wherein $R_9$, $R_{10}$ and $R'_{10}$ each independently represent a group permitted by the rules of valence.

The term "acylamino" is art-recognized and refers to a moiety that can be represented by the general formula:

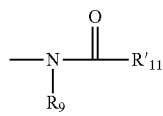

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

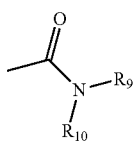

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

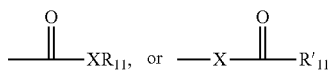

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, —O-alkynyl, —O—$(CH_2)_m$—$R_8$, where m and $R_8$ are described above.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (n)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, it may be isolated using chiral chromatography methods, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

Selected Compounds of the Invention

An aspect of the invention is a compound of formula (I) or a pharmaceutically acceptable salt thereof

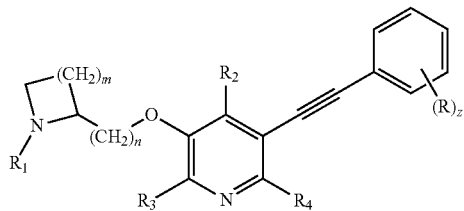

(I)

wherein:
R represents, independently for each occurrence, halogen, C1-C6 alkyl, allyl, C1-C6 alkyloxy, amino, hydroxyl, nitro, cyano, or trifluoro-C1-C4 alkyl;
$R_1$ represents hydrogen, C1-C6 alkyl, allyl, or C3-C6 cycloalkyl;
$R_2$, $R_3$, and $R_4$ independently represent hydrogen, C1-C6 alkyl, allyl, or C3-C6 cycloalkyl, or C1-C6 alkyl substituted with at least one fluorine;
m is an integer ranging from 1 to 3;
n is an integer selected from 1 and 2; and
z is an integer ranging from 0 to 5;
with the proviso that the compound of formula (I) is not

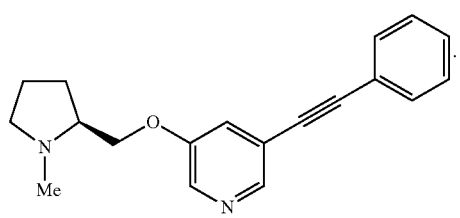 [SMILES: CN1CCC[C@H]1COc1cncc(C#Cc2ccccc2)c1]

In one embodiment, m is 1. In one embodiment, m is 2. In one embodiment, m is 3.

In one embodiment in accordance with any one of the foregoing combinations of limitations, n is 1. In one embodiment in accordance with any one of the foregoing combinations of limitations, n is 2.

In one embodiment in accordance with any one of the foregoing combinations of limitations, z is 0. In one embodiment in accordance with any one of the foregoing combinations of limitations, z is 1. In one embodiment in accordance with any one of the foregoing combinations of limitations, z is 2.

In one embodiment in accordance with any one of the foregoing combinations of limitations, R represents, independently for each occurrence, halogen, C1-C6 alkyl, C1-C6 alkyloxy, amino, or trifluoro-C1-C4 alkyl.

In one embodiment in accordance with any one of the foregoing combinations of limitations, R represents, independently for each occurrence, halogen, methyl, methoxy, amino, or trifluoromethyl.

In one embodiment in accordance with any one of the foregoing combinations of limitations, $R_1$ is C1-C6 alkyl.

In one embodiment in accordance with any one of the foregoing combinations of limitations, $R_1$ is methyl.

In one embodiment in accordance with any one of the foregoing combinations of limitations, $R_1$ is hydrogen.

In one embodiment in accordance with any one of the foregoing combinations of limitations, $R_2$, $R_3$, and $R_4$ independently represent hydrogen.

In one embodiment the compound is

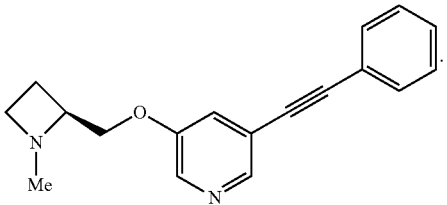 [SMILES: CN1CC[C@H]1COc1cncc(C#Cc2ccccc2)c1]

In one embodiment the compound is selected from the group consisting of:

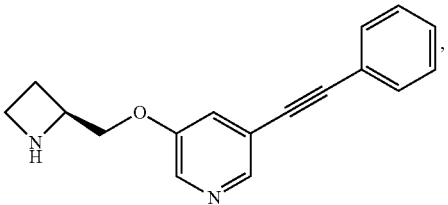

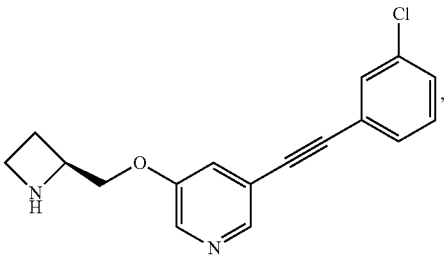

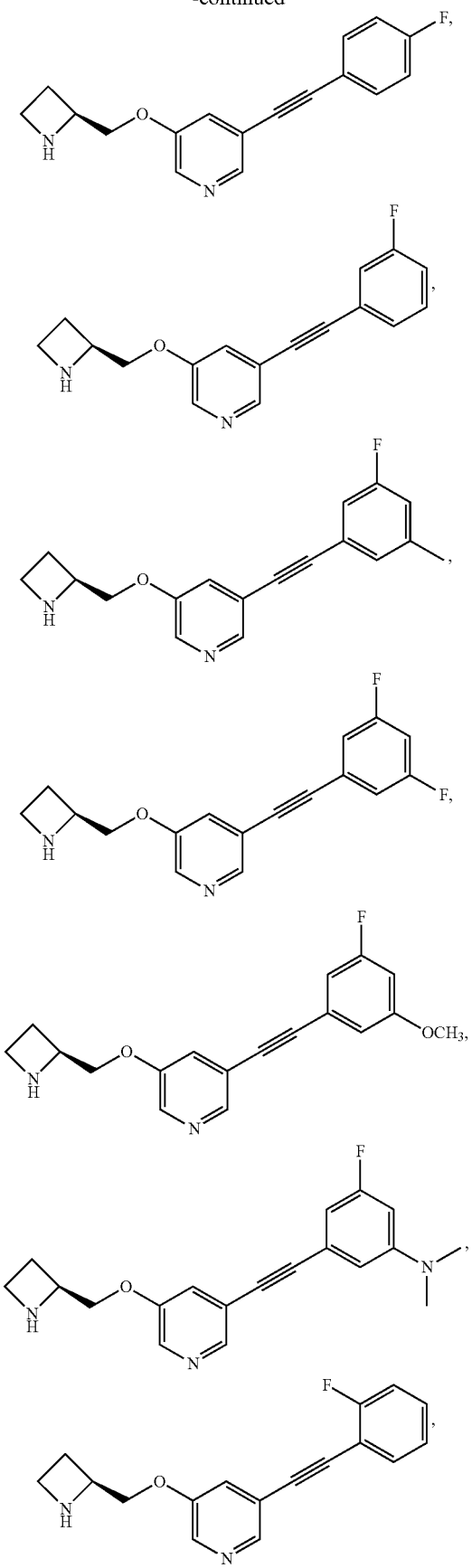

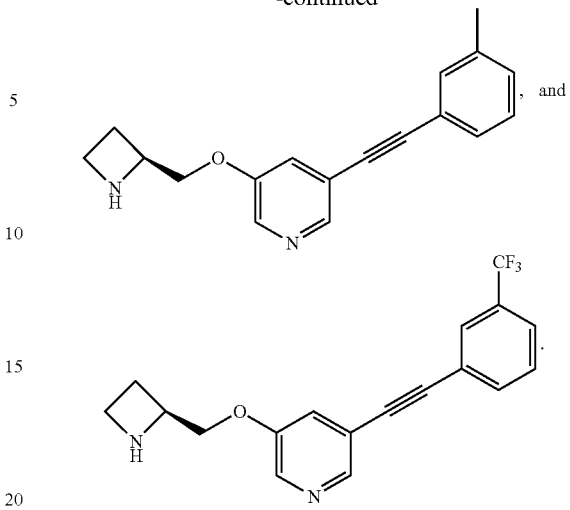

An aspect of the invention is a compound of formula (II) or a pharmaceutically acceptable salt thereof

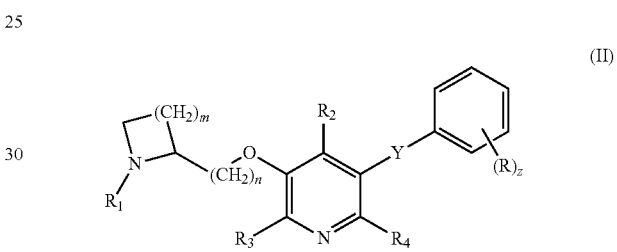

(II)

wherein:
R represents, independently for each occurrence, halogen, C1-C6 alkyl, allyl, C1-C6 alkyloxy, amino, hydroxyl, nitro, cyano, or trifluoro-C1-C4 alkyl;
$R_1$ represents hydrogen, C1-C6 alkyl, allyl, or C3-C6 cycloalkyl;
$R_2$, $R_3$, and $R_4$ independently represent hydrogen, C1-C6 alkyl, allyl, or C3-C6 cycloalkyl, or C1-C6 alkyl substituted with at least one fluorine;
Y is O, S, or N($R^C$);
$R^C$ is hydrogen, C1-C6 alkyl, or allyloxycarbonyl;
m is an integer ranging from 1 to 3;
n is an integer selected from 1 and 2; and
z is an integer ranging from 0 to 5.

In one embodiment, m is 1. In one embodiment, m is 2. In one embodiment, m is 3.

In one embodiment in accordance with any one of the foregoing combinations of limitations, n is 1. In one embodiment in accordance with any one of the foregoing combinations of limitations, n is 2.

In one embodiment in accordance with any one of the foregoing combinations of limitations, z is 0. In one embodiment in accordance with any one of the foregoing combinations of limitations, z is 1. In one embodiment in accordance with any one of the foregoing combinations of limitations, z is 2.

In one embodiment in accordance with any one of the foregoing combinations of limitations, R represents, independently for each occurrence, halogen, C1-C6 alkyl, C1-C6 alkyloxy, amino, or trifluoro-C1-C4 alkyl.

In one embodiment in accordance with any one of the foregoing combinations of limitations, R represents, independently for each occurrence, halogen, methyl, methoxy, amino, or trifluoromethyl.

In one embodiment in accordance with any one of the foregoing combinations of limitations, $R_1$ is C1-C6 alkyl.

In one embodiment in accordance with any one of the foregoing combinations of limitations, $R_1$ is methyl.

In one embodiment in accordance with any one of the foregoing combinations of limitations, $R_1$ is hydrogen.

In one embodiment in accordance with any one of the foregoing combinations of limitations, $R_2$, $R_3$, and $R_4$ independently represent hydrogen.

An aspect of the invention is a compound of formula (III) or a pharmaceutically acceptable salt thereof (III)

wherein:
$R_1$ represents hydrogen, C1-C6 alkyl, allyl, or C3-C6 cycloalkyl;
$R_2$, $R_3$, and $R_4$ independently represent hydrogen, C1-C6 alkyl, allyl, or C3-C6 cycloalkyl, or C1-C6 alkyl substituted with at least one fluorine;
$R_5$ represents Y represents —C≡C— or O;
A represents hydrogen, halogen, methyl, C2-C6 alkyl, methoxy, hydroxy, amino, trifluoromethyl, isopropyl, or t-butyl;
W represents O, S, or N($R^D$);
$R^D$ represents hydrogen, C1-C6 alkyl, or allyloxycarbonyl;
m is an integer ranging from 1 to 3; and
n is an integer selected from 1 and 2.

In one embodiment, m is 1. In one embodiment, m is 2. In one embodiment, m is 3.

In one embodiment in accordance with any one of the foregoing combinations of limitations, n is 1. In one embodiment in accordance with any one of the foregoing combinations of limitations, n is 2.

In one embodiment in accordance with any one of the foregoing combinations of limitations, $R_1$ is C1-C6 alkyl.

In one embodiment in accordance with any one of the foregoing combinations of limitations, $R_1$ is methyl.

In one embodiment in accordance with any one of the foregoing combinations of limitations, $R_2$, $R_3$, and $R_4$ independently represent hydrogen.

In one embodiment in accordance with any one of the foregoing combinations of limitations, Y is —C≡C—.

In one embodiment in accordance with any one of the foregoing combinations of limitations, Y is O.

An aspect of the invention is a compound of formula (IV) or a pharmaceutically acceptable salt thereof (IV)

wherein:
R represents, independently for each occurrence, halogen, C1-C6 alkyl, allyl, C1-C6 alkyloxy, amino, hydroxyl, nitro, cyano, or trifluoro-C1-C4 alkyl;
$R_1$ represents $R_2$, $R_3$, and $R_4$ independently represent hydrogen, C1-C6 alkyl, allyl, or C3-C6 cycloalkyl, or C1-C6 alkyl substituted with at least one fluorine;
$R_h$ represents C1-C6 alkyl, C3-C6 cycloalkyl, aryl, or C1-C6 alkyl substituted with at least one fluorine;
m is an integer ranging from 1 to 3;
n is an integer selected from 1 and 2; and
z is an integer ranging from 0 to 5.

In one embodiment, m is 1. In one embodiment, m is 2. In one embodiment, m is 3.

In one embodiment in accordance with any one of the foregoing combinations of limitations, n is 1. In one embodiment in accordance with any one of the foregoing combinations of limitations, n is 2.

In one embodiment in accordance with any one of the foregoing combinations of limitations, z is 0. In one embodiment in accordance with any one of the foregoing combinations of limitations, z is 1. In one embodiment in accordance with any one of the foregoing combinations of limitations, z is 2.

In one embodiment in accordance with any one of the foregoing combinations of limitations, R represents, independently for each occurrence, halogen, C1-C6 alkyl, C1-C6 alkyloxy, amino, or trifluoro-C1-C4 alkyl.

In one embodiment in accordance with any one of the foregoing combinations of limitations, R represents, independently for each occurrence, halogen, methyl, methoxy, amino, or trifluoromethyl.

In one embodiment in accordance with any one of the foregoing combinations of limitations, $R_2$, $R_3$, and $R_4$ independently represent hydrogen.

An aspect of the invention is a compound of formula (V) or a pharmaceutically acceptable salt thereof

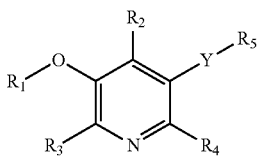

wherein:
$R_1$ represents

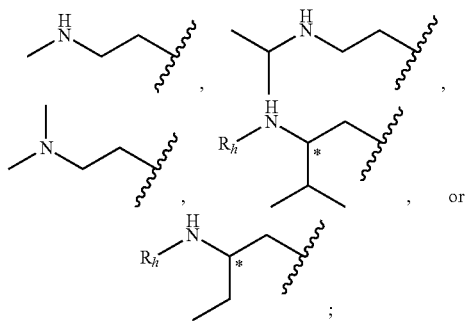

$R_2$, $R_3$, and $R_4$ independently represent hydrogen, C1-C6 alkyl, allyl, or C3-C6 cycloalkyl, or C1-C6 alkyl substituted with at least one fluorine;
$R_h$ represents C1-C6 alkyl, C3-C6 cycloalkyl, aryl, or C1-C6 alkyl substituted with at least one fluorine;
$R_5$ represents

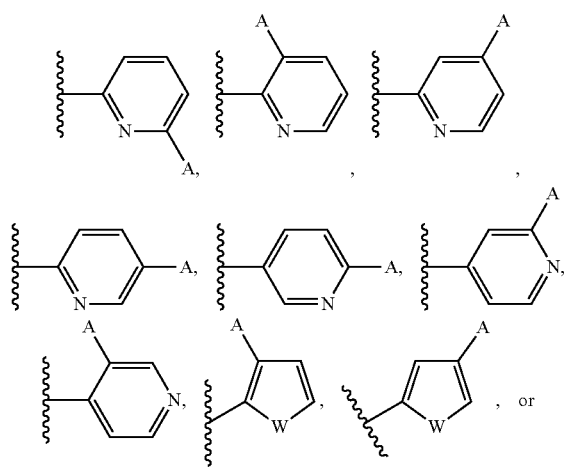

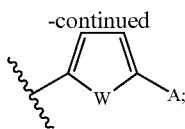

Y represents —C≡C— or O;
A represents hydrogen, halogen, methyl, C2-C6 alkyl, methoxy, hydroxy, amino, trifluoromethyl, isopropyl, or t-butyl;
W represents O, S, or N($R^D$);
$R^D$ represents hydrogen, C1-C6 alkyl, or allyloxycarbonyl;
m is an integer ranging from 1 to 3; and
n is an integer selected from 1 and 2.

In one embodiment, m is 1. In one embodiment, m is 2. In one embodiment, m is 3.

In one embodiment in accordance with any one of the foregoing combinations of limitations, n is 1. In one embodiment in accordance with any one of the foregoing combinations of limitations, n is 2.

In one embodiment in accordance with any one of the foregoing combinations of limitations, $R_2$, $R_3$, and $R_4$ independently represent hydrogen.

In various embodiments in accordance with any one of the foregoing combinations of limitations, $R_h$ represents C1-C6 alkyl, C3-C6 cycloalkyl, aryl, or C1-C6 alkyl substituted with 1, 2, 3, 4, 5, or 6 fluorines.

An aspect of the invention is a pharmaceutical composition, comprising a compound of the invention; and a pharmaceutically acceptable carrier.

An aspect of the invention is a method of treating a disorder selected from the group consisting of addiction, pain, obesity, schizophrenia, epilepsy, mania and manic depression, anxiety, Alzheimer's disease, learning deficit, cognition deficit, attention deficit, memory loss, Lewy Body Dementia, Attention Deficit Hyperactivity Disorder (ADHD), Parkinson's disease, Huntington's disease, Tourette's syndrome, amyotrophic lateral sclerosis, inflammation, stroke, spinal cord injury, dyskinesias, obsessive compulsive disorder, chemical substance abuse, alcoholism, memory deficit, pseudodementia, Ganser's syndrome, migraine pain, bulimia, premenstrual syndrome or late luteal phase syndrome, tobacco abuse, post-traumatic syndrome, social phobia, chronic fatigue syndrome, premature ejaculation, erectile difficulty, anorexia nervosa, autism, mutism, trichotillomania, hypothermia, and disorders of sleep. The method comprises the step of administering to a subject in need thereof a therapeutically effective amount of a compound of the invention. In one embodiment the disorder is addiction. In one embodiment the disorder is hypothermia.

Dosages

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible effects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

Formulations

The compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Kits

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

EXAMPLES

The invention now being generally described, it will be more readily understood by reference to the following examples which are included merely for purposes of illustration of certain aspects and embodiments of the present invention, and are not intended to limit the invention.

Overview & General Procedures

Methods, Design Strategy for VMY-2-95 and Rational Optimization of New Series of Nicotinic Ligands.

Figure 2:
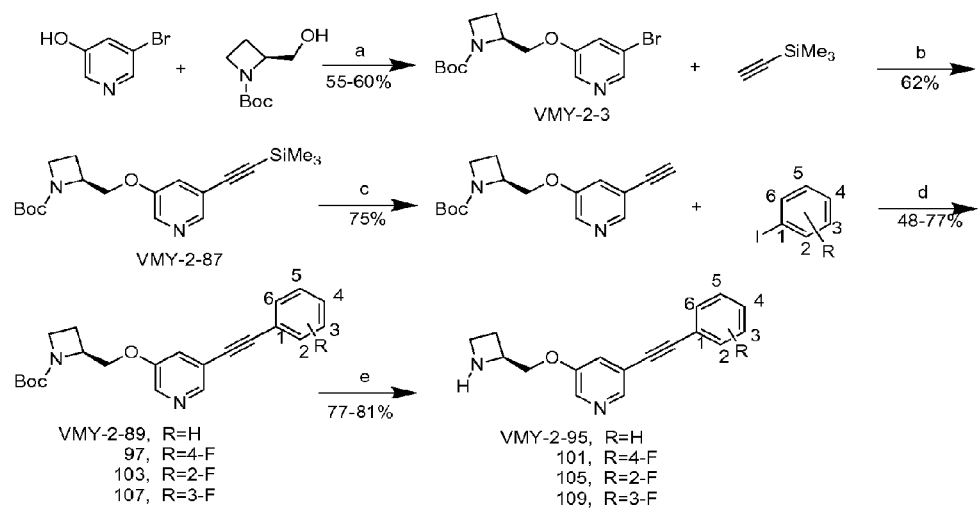
FIG. 2 depicts Scheme 1, Method C for synthesis of certain indicated compounds of the invention.
Figure 8:
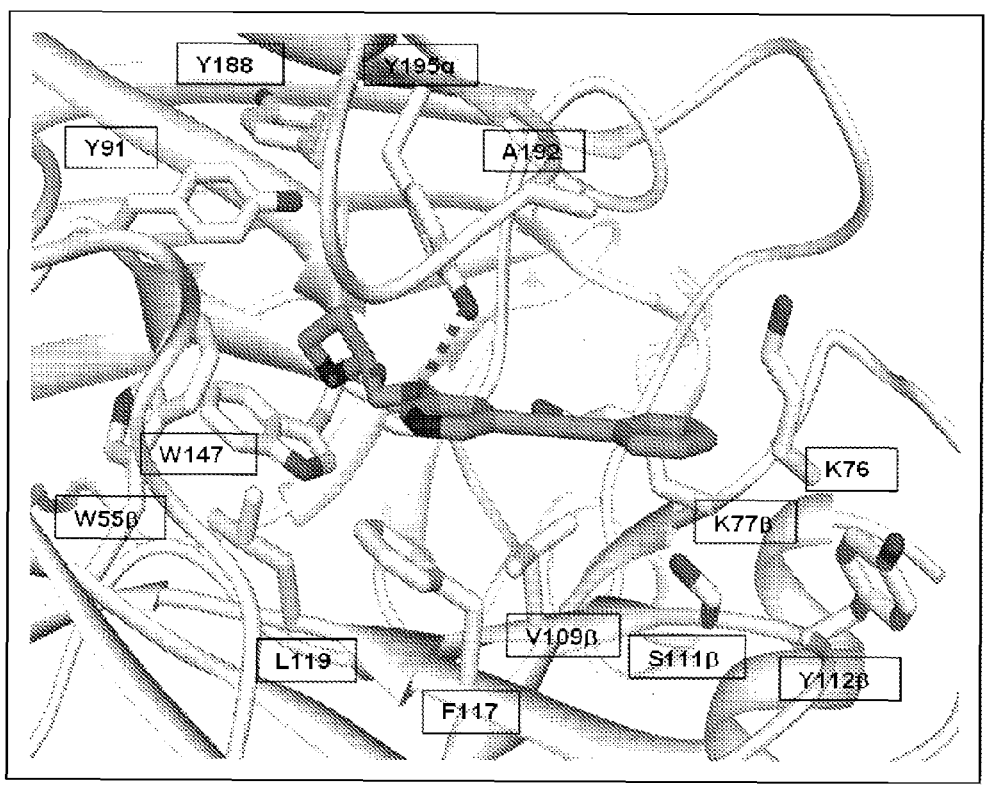
FIG. 8 shows predicted structural models of α4β2 nAChR. Atomic level interactions between VMY-2-95 with α4β2 nAChR are pictured. Binding site residues are labeled and shown in a stick model rendering.

Utilizing a homologous series, we optimized Saz-A by replacing the alkyl hydroxyl with a benzene group resulting in the design of VMY-2-95 (FIG. 7). We anticipated that VMY-2-95 would have an enhanced CNS profile based on the physicochemical properties of PSA (34.15), lipophilicity (log P=2.36) and log BB (0.22). From our modeling studies we envisioned that the benzene ring would provide more rigidity and favorable interactions with the α4β2 nAChR subtype (FIG. 8). Further modifications on benzene ring in VMY-2-95 provided the compounds in series 1. The compounds (95-139) in series 1 were synthesized as shown in FIGS. 1 and 2. For routes 1 and 2 (FIGS. 1 and 2), compounds were synthesized starting with N-Boc protected Mitsunobu product VMY-2-3. This intermediate was subjected to Sonogashira reaction conditions followed by subsequent deprotection of the Boc group to yield the final compounds in series 1.

Figure 4:
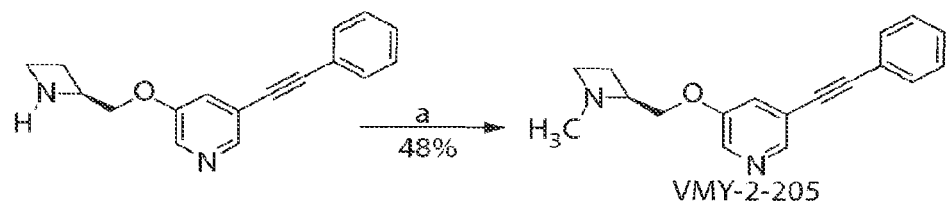
FIG. 4 depicts Scheme 3 for synthesis of compound VMY-2-205 of the invention.

To further understand the importance of the azetidine ring, N-substitution and stereochemistry on the binding affinity of ligands for nAChRs, modifications of VMY-2-95 were carried out as shown in FIG. 7. Analogues VMY-2-161, VMY-2-177 and VMY-2-191 (FIG. 3), were synthesized by employing the same methodology as shown in FIGS. 1 and 2. The N-methyl azetidine (VMY-2-205, FIG. 4) was prepared by reductive methylation of the secondary amine with formaldehyde.

General Methods.

Nicotinic acetylcholine receptors (nAChRs) in the neuronal systems are pentameric structures composed of subunits distinct from those found in skeletal muscles. The existence of nine α-subunits (α2-α10) and three β-subunits (β2-β4) in the mammalian neuronal systems has been described.

The predominant subtype with high affinity for nicotine is comprised of three α-subunits and two β-subunits.

The affinity of compounds of the invention for nAChRs may be investigated in three tests for in vitro inhibition of $^3$H-epibatidin binding, $^3$H-α-bungarotoxin binding and $^3$H-cytisine binding as described below.

Cell Lines and Cell Culture.

The cell line expressing rat α3β4 nAChRs, KXα3β4R2, was established previously by stably transfecting HEK 293 cells with combinations of rat nAChR α3 and β4 subunit genes. The cell line expressing human α4β2 nAChRs, YXα4β2H1, were established recently (Tuan et al., 2012, manuscript in preparation). These cell lines were maintained in minimum essential medium (MEM) supplemented with 10% fetal bovine serum, 100 units/mL penicillin G, 100 mg/mL streptomycin and selective antibiotics at 37° C. with 5% $CO_2$ in a humidified incubator. Tissue culture medium and antibiotics were obtained from Invitrogen Corporation (Carlsbad, Calif.), unless otherwise stated. Fetal bovine serum and horse serum were provided by Gemini Bio-Products (Woodland, Calif.).

[$^3$H]-Epibatidine Radioligand Binding Assay.

Stably transfected cell lines, tissue culture conditions, membrane preparation procedures and binding assays were described previously. Briefly, cultured cells at >80% confluence were removed from their flasks (80 cm$^2$) with a disposable cell scraper and placed in 10 mL of 50 mM Tris.HCl buffer (pH 7.4, 4° C.). The cell suspension was centrifuged at 10,000×g for 5 min and the pellet was collected. The cell pellet was then homogenized in 10 mL buffer with a polytron homogenizer and centrifuged at 36,000 g for 10 min at 4° C. The membrane pellet was resuspended in fresh buffer, and aliquots of the membrane preparation were used for binding assays. The concentration of [$^3$H]-epibatidine used was ~500 pM for competition binding assays. Nonspecific binding was assessed in parallel incubations in the presence of 300 μM nicotine. Bound and free ligands were separated by vacuum filtration through Whatman GF/C filters treated with 0.5% polyethylenimine.

The filter-retained radioactivity was measured by liquid scintillation counting. Specific binding was defined as the difference between total binding and nonspecific binding. Data from competition binding assays were analyzed using Prism 5 (GraphPad Software, San Diego, Calif.).

$^{86}$Rb$^+$ Efflux Assay.

Functional properties of compounds at nAChRs expressed in the transfected cells were measured using $^{86}$Rb$^+$ efflux assays as described previously. In brief, cells were plated into 24-well plates coated with poly-D-lysine. The plated cells were grown at 37° C. for 18 to 24 hour to reach 85-95% confluence. The cells were then incubated in growth medium (0.5 mL/well) containing $^{86}$Rb$^+$ (2 μCi/mL) for 4 hour at 37° C. The loading mixture was then aspirated, and the cells were washed four times with 1 mL buffer (15 mM HEPES, 140 mM NaCl, 2 mM KCl, 1 mM MgSO$_4$, 1.8 mM CaCl$_2$, 11 mM Glucose, pH 7.4). One mL of buffer with or without compounds to be tested was then added to each well. After incubation for 2 min, the assay buffer was collected for measurements of $^{86}$Rb$^+$ released from the cells. Cells were then lysed by adding 1 mL of 100 mM NaOH to each well, and the lysate was collected for determination of the amount of $^{86}$Rb$^+$ that was in the cells at the end of the efflux assay. Radioactivity of assay samples and lysates was measured by liquid scintillation counting. Total loading (cpm) was calculated as the sum of the assay sample and the lysate of each well. The amount of $^{86}$Rb$^+$ efflux was expressed as a percentage of $^{86}$Rb$^+$ loaded. Stimulated $^{86}$Rb$^+$ efflux was defined as the difference between efflux in the presence and absence of nicotine. For obtaining EC$_{50}$ and E$_{max}$ values, stimulation curves were constructed in which 8 different concentrations of a ligand were included in the assay. For obtaining an IC$_{50(10')}$ value, inhibition curves were constructed in which 8 different concentrations of a compound were applied to cells for 10 min before 100 μM nicotine was applied to measure stimulated efflux. EC$_{50}$, E$_{max}$ and IC$_{50(10')}$ values were determined by nonlinear least-squares regression analyses (GraphPad, San Diego, Calif.).

Binding Assays for Targets Other than nAChRS.

All binding assays for targets other than nAChRs were performed by the National Institute of Mental Health's Psychoactive Drug Screening Program (PDSP) supported by NIMH grant HHSN-271-2008-00025-C(PI: Bryan Roth). For experimental details (K$_i$ determinations, receptor binding profiles, functional data, MDR1 data, etc. as appropriate) refer to the PDSP web site http://pdsp.med.unc.edu/.

In Vitro Inhibition of $^3$H-Cytisine Binding.

The predominant subtype with high affinity for nicotine is comprised of α4 and β2 subunits. nAChRs of the latter type may selectively be labeled by the nicotine ligand $^3$H-cytisine.

Tissue preparation may be performed at 0-4° C. unless otherwise indicated. Cerebral cortices from male Wistar rats (150-250 g) may be homogenized for 20 sec in 15 mL Tris, HCl (50 mM, pH 7.4) containing 120 mM NaCl, 5 mM KCl, 1 mM MgCl$_2$ and 2.5 mM CaCl$_2$ using an Ultra-Turrax homogenizer. The homogenate may then be centrifuged at 27,000×g for 10 min. The supernatant may then be discarded and the pellet resuspended in fresh buffer and centrifuged a second time. The final pellet may be resuspended in fresh buffer (35 mL per g of original tissue) and used for binding assays.

Aliquots of 500 μL homogenate may be added to 25 μL of test solution and 25 μL of $^3$H-cytisine (1 nM, final concentration), mixed and incubated for 90 min at 2° C. Non-specific binding may then be determined using (−)- nicotine (100 μM, final concentration). After incubation the samples may be added to 5 mL of ice-cold buffer and poured directly onto Whatman GF/C glass fiber filters under suction and immediately washed with 2×5 mL ice-cold buffer. The amount of radioactivity on the filters may then be determined by conventional liquid scintillation counting. Specific binding is total binding minus non-specific binding.

In Vitro Inhibition of $^3$H-α-Bungarotoxin Binding Rat Brain.

α-Bungarotoxin is a peptide isolated from the venom of the Elapidae snake *Bungarus multicinctus* and has high affinity for neuronal and neuromuscular nicotinic receptors, where it acts as a potent antagonist. $^3$H-α-Bungarotoxin binds to a single site in rat brain with a unique distribution pattern in rat brain.

$^3$H-α-Bungarotoxin labels nAChR are formed by the α7 subunit isoform found in the brain and the isoform in the neuromuscular junction. Functionally, the α7 homo-oligomer expressed in oocytes has a calcium permeability greater than neuromuscular receptors and, in some instances greater than NMDA channels.

Tissue Preparation.

Preparations may be performed at 0-4° C. unless otherwise indicated. Cerebral cortices from male Wistar rats (150-250 g) may be homogenized for 10 sec in 15 mL 20 mM Hepes buffer containing 118 mM NaCl, 4.8 mM KCl, 1.2 mM $MgSO_4$ and 2.5 mM $CaCl_2$ (pH 7.5) using an Ultra-Turrax homogenizer. The tissue suspension may then be centrifuged at 27,000×g for 10 min. The supernatant is discarded and the pellet is washed twice by centrifugation at 27,000×g for 10 min in 20 mL fresh buffer, and the final pellet may be resuspended in fresh buffer containing 0.01% BSA (35 mL per g of original tissue) and used for binding assays.

Aliquots of 500 μL homogenate may be added to 25 μL of test solution and 25 μL of $^3$H-α-bungarotoxin (2 nM, final concentration), mixed and incubated for 2 h at 24° C. Non-specific binding may then be determined using (−)-nicotine (1 mM, final concentration). After incubation the samples may be added to 5 mL of ice-cold Hepes buffer containing 0.05% PEI and poured directly onto Whatman GF/C glass fiber filters (presoaked in 0.1% PEI for at least 6 h) under suction and immediately washed with 2×5 mL ice-cold buffer. The amount of radioactivity on the filters may then be determined by conventional liquid scintillation counting. Specific binding is total binding minus non-specific binding.

In Vitro Inhibition of $^3$H-Epibatidin Binding.

Epibatidin is an alkaloid that was first isolated from the skin of the Ecuadoran frog *Epipedobates tricolor* and was found to have very high affinity for neuronal nicotinic receptors, where it acts as a potent agonist. It is believed that $^3$H-epibatidin binds to sites in rat brain, both of which have pharmacological profiles consistent with neuronal nicotinic receptors and a similar brain regional distribution (Hougling et al., Mol. Pharmacol. 48, 280-287 (1995)).

The high affinity binding sites in rat brain for $^3$H-epibatidin are mainly α4β2 nAChR subtype.

Tissue Preparation.

Preparations may be performed at 0-4° C. unless otherwise indicated. The forebrain (cerebellum) from a male Wistar rat (150-250 g) may be homogenized for 10-20 sec in 20 mL Tris, HCl (50 mM, pH 7.4) using an Ultra-Turrax homogenizer. The tissue suspension may then be centrifuged at 27,000×g for 10 min. The supernatant is then discarded and the pellet may then be washed three times by centrifugation at 27,000×g for 10 min in 20 mL fresh buffer, and the final pellet may be resuspended in fresh buffer (400 mL per g of original tissue) and used for binding assays.

Aliquots of 2.0 mL homogenate may be added to 0.100 mL of test solution and 0.100 mL of $^3$H-epibatidin (0.3 nM, final concentration), mixed and incubated for 2 h at room temperature. Non-specific binding may then be determined using (−)-nicotine (30 μM, final concentration). After incubation the samples may then be poured directly onto Whatman GF/C glass fiber filters (presoaked in 0.1% PET for at least 20 min) under suction and immediately washed with 2×5 mL ice-cold buffer. The amount of radioactivity on the filters may be determined by conventional liquid scintillation counting. Specific binding is total binding minus non-specific binding.

General Procedures for Animal Behavioral Studies.

Separate sets of young adult female Sprague-Dawley rats were used for the nicotine self-administration study (N=15) and for the locomotor activity study (N=12). The studies were conducted in accordance with the regulations outlined by the Duke University Animal Care and Use Committee. The rats housed in approved standard laboratory conditions in a Duke University vivarium facility near the testing room to minimize stress induced by transporting the rats. The rats were kept on a 12:12 reverse day/night cycle, so that they were in their active phase during behavioral testing. The rats in the drug iv self-administration studies were singly housed to prevent them from damaging each other's catheters. The rats in the locomotor activity studies were housed in groups of 2-3. All rats were allowed access to water at all times; the rats in the nicotine-self-administration study were fed daily approximately 30 minutes after completing the sessions while those in the locomotor activity study had continuous access to food.

VMY-2-95 Administration.

VMY-2-95 was injected s.c. 10 minutes before testing in a volume of 1 mL/kg of saline. The doses (0, 0.3, 1 and 3 mg/kg) were given in a counterbalanced order with at least two days between successive injections. For the nicotine self-administration study the VMY-2-95 the acute dose-effect study was tested twice while for the locomotor activity study the dose-effect function was tested once.

Nicotine Self-Administration.

Before beginning nicotine self-administration, the rats were trained for three sessions on lever pressing for food reinforcement. Then they were fitted with i.v. catheters and they received nicotine infusions (0.03 mg/kg/infusion) on an FR1 schedule for ten sessions. The rats were trained to self-administer nicotine (0.03 mg/kg/infusion, IV) via operant lever response (FR1) with a visual secondary reinforcer. Two levers were available to be pressed and only one caused the delivery of nicotine on an FR1 schedule. Pressing the lever on the active side resulted in the activation of the feedback tone for 0.5 second and the immediate delivery of one 50-μl infusion of nicotine in less than 1 second. Each infusion was immediately followed by a one-minute period in which the cue lights went out, the house light came on and responses were recorded but not reinforced.

Locomotor Activity.

Figure 10:
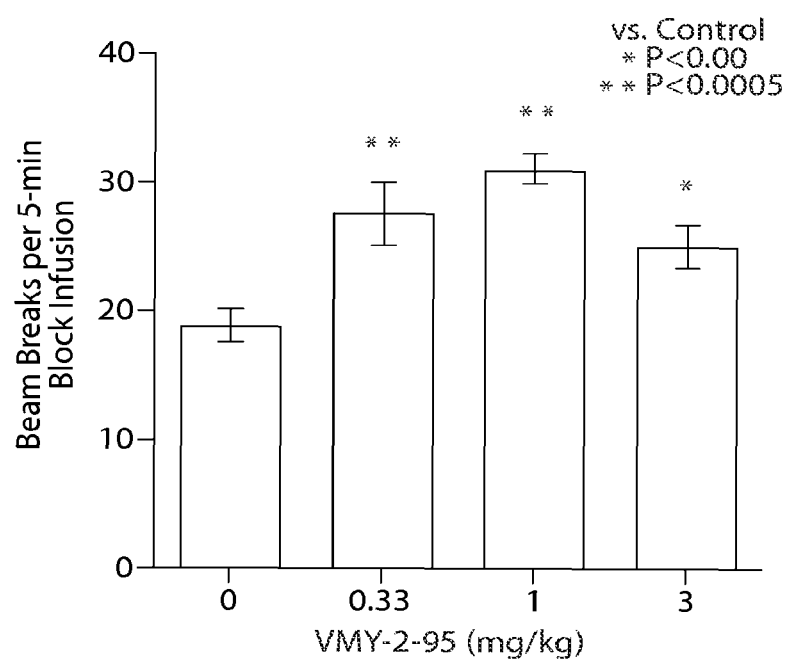
FIG. 10 shows acute VMY-2-95 effects on locomotor activity. The graph shows the effect of VMY-2-95 on locomotor activity in the 8-figure maze at 1 hour (Mean+S.E.M; n=12).
Figure 11:
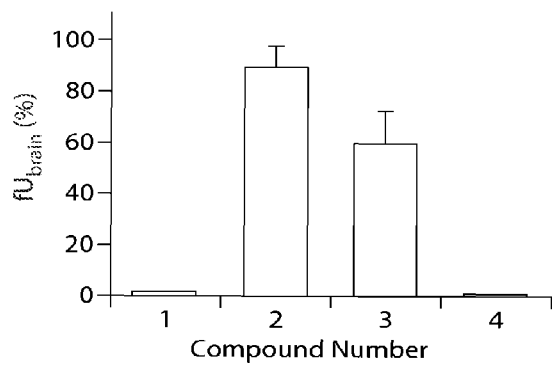
FIG. 11 shows in vitro rat brain tissue protein binding data for propranolol, varenicline, sazetidine A, and VMY-2-95.
Figure 12:
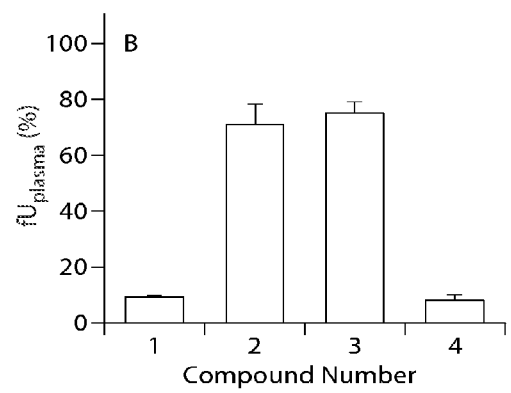
FIG. 12 shows in vitro rat plasma protein binding data for propranolol, varenicline, sazetidine A, and VMY-2-95.
Figure 13:
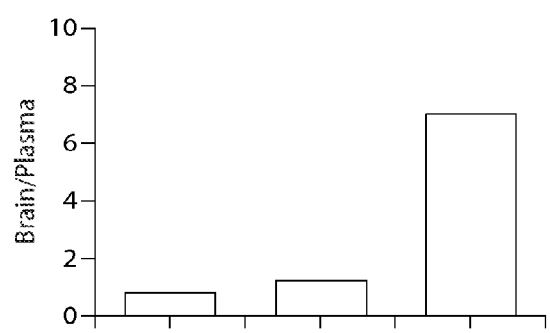
FIG. 13 shows in vitro rat protein binding data comparing brain and plasma.

Another set of rats (N=12) was tested for acute VMY-2-95 effects on locomotor activity in a figure-8 maze over the course of a 1-hour session (see FIG. 10). The mazes had continuous enclosed alleys 10×10 cm in the shape of a figure-8 (Crofton et al., 1991). The dimensions of the apparatus were 70 cm long and 42 cm wide, with a 21×16 cm central arena, a 20-cm high ceiling and two blind alleys extending 20 cm from either side. Eight infrared photobeams, which crossed the alleys, indexed locomotor activity.

One photobeam was located on each of the two blind alleys and three were located on each of two loops of the figure-8. Numbers of photobeam breaks were recorded for five minutes blocks over the one-hour session. The repeated measures were VMY-2-95 dose and the repeated administration of each dose. Significant interactions were followed up by tests of the simple main effects. Alpha of p<0.05 (two-tailed) was used as the threshold for significance.

Physicochemical Properties and Ligand Efficiency.

Molecular properties of compounds in series 1 were calculated according the available software tools. Ligand binding efficiency was calculated according to the Hopkins equation: LE=1.372*(–log Ki (Moles))/N. Molecular weight and c Log P were calculated from chembiodraw ultra 11.0. Polar Surface Area (PSA) was calculated from www.chemicalize.org. Log BB was calculated from the following equation: Log BB=–0.0148PSA+0.132c Log P+0.139.

Chemical Synthesis of Compounds.

All reagents and solvents were commercially available and used without further purification. Chromatography was performed for purification of final compounds using a Biotage SP-1 system with silica gel cartridges. NMR spectra were recorded on a Varian 400 MR spectrometer at 400 MHz for H-1 and 100 MHz for C-13. Chemical shifts (δ) are given in ppm downfield from tetramethylsilane, and coupling constants (J-values) are reported in hertz (Hz). Mass spectroscopy was performed using Waters Q-TOF premier mass spectrometer. The purity of final compounds was evaluated by CHN analysis.

Figure 22:
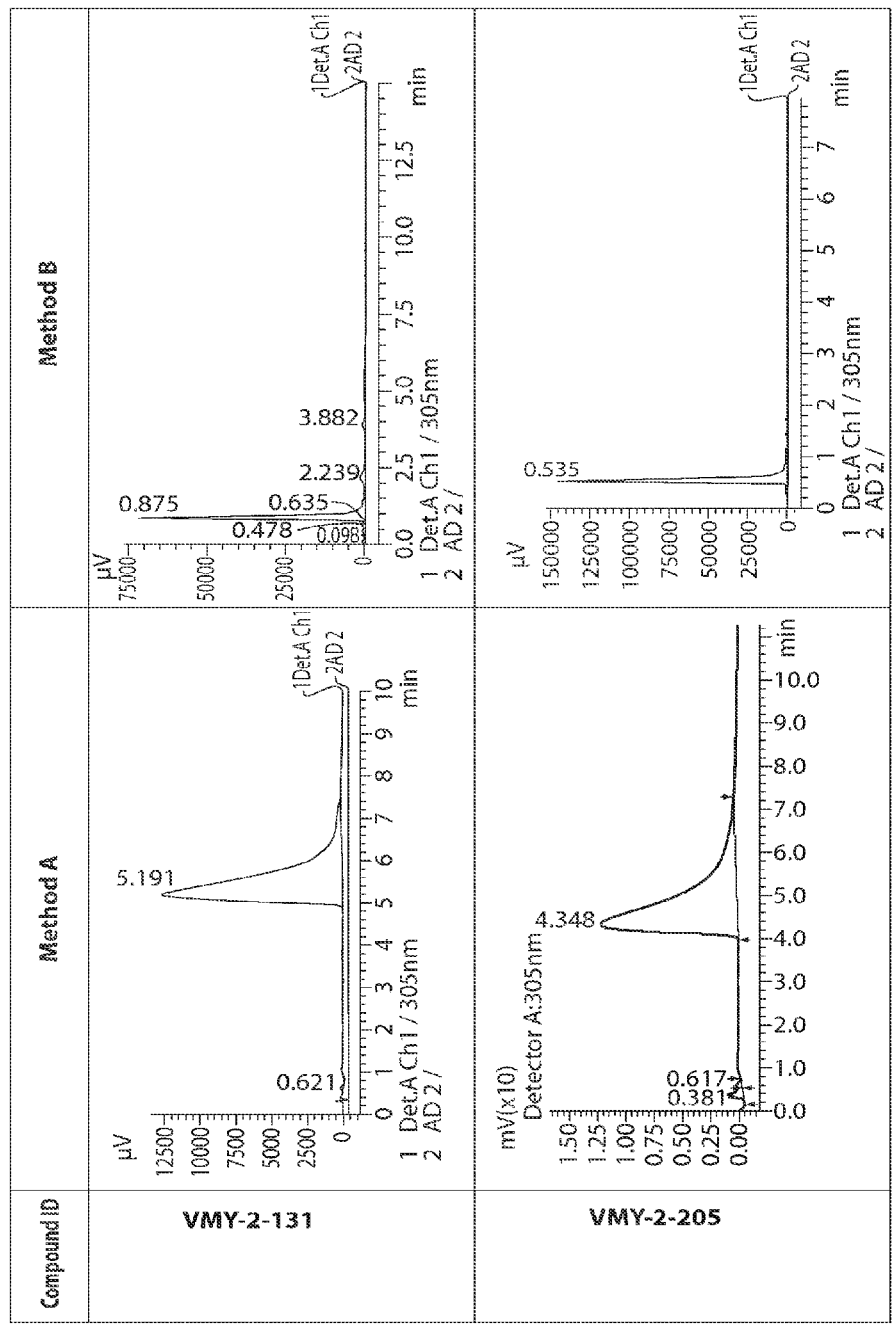
FIG. 22 shows HPLC purity data for compounds 131 and 205.

The purity of final compounds was evaluated by C, H, N analysis (Atlantic microlabs) (FIG. 21) and HPLC methods for compounds 131 and 205 FIG. 22). Detailed synthetic and characterization data (series 2 & 3) and experimental procedure for computational studies are presented below.

General Procedure for Mitsunobu Reaction (Method A).

To a mixture of 5-Bromo-3-pyridinol (1.2 equiv) and Ph$_3$P (1.6 equiv) in anhydrous THF taken in a flame-dried flask under N$_2$, N-Boc protected alcohol (1 equiv) was added and the mixture was cooled to –10° C. Diethyl azodicarboxylate (40% w/v) in toluene (1.6 equiv) was added dropwise to the mixture and was warmed gradually to the room temperature. After 48 h, the reaction mixture was quenched with 1 mL of water and the solvent was removed under reduced pressure. The resulting yellow oil was purified by column chromatography on silica gel to yield 55-60% as a white solid.

General Procedure for Sonogashira Coupling Reaction. One-Pot Synthesis (Method B):

The Mitsunobu adduct (1 equiv), Pd(PPh$_3$)$_2$Cl$_2$ (0.04 eq, 4 mol %), CuI (0.08 eq, 8 mol %), and PPh$_3$ (0.08 eq, 8 mol %) was placed in an oven-dried round bottom flask with nitrogen. After addition of i-Pr$_2$NH (1 mL) and toluene (3-5 mL), the mixture was stirred at room temperature for 5 min and (trimethylsilyl) acetylene (2.7 equiv) was added and stirred at r.t for 10 min. The whole reaction mixture was stirred at 80° C. for 18 h, a solution of KOH in methanol and water (4:1) was added in one portion and the mixture was stirred for additional 3 h at 25° C. Then the second substituted aryl iodide was added and stirred continued for 16 h at 25° C. or 80° C. in case of substituted aryl bromide. The reaction mixture was quenched with saturated NH$_4$Cl solution and extracted with CH$_2$Cl$_2$. The combined organic layers were washed with 2 N HCl, water and saturated NaCl solution. The organic phase was separated and dried over anhydrous sodium sulfate, filtered, and concentrated under reduced pressure to give crude product. The crude product was purified by column chromatography. See FIG. 1.

Sequential Desilylation and Sonogashira Coupling of TMS-Protected VMY-2-87. (Method C).

An oven-dried and nitrogen-filled round bottom flask was charged with (S)-tert-butyl-2-((5-((trimethylsilyl)ethynyl)pyridin-3-yloxy)methyl)azetidine-1-carboxylate (VMY-2-87, 1 equiv), KOH (2 equiv) methanol in water (20:1). The whole reaction mixture was stirred 25° C. for 3 h. It was then added to a second flask which contained a performed mixture of Pd(PPh$_3$)$_2$Cl$_2$ (0.02 eq, 2 mol %), CuI (0.02 eq, 2 mol %), PPh$_3$ (0.04 eq, 4 mol %) i-Pr$_2$NH (1 mL), toluene (3-5 mL) and substituted fluoro iodobenzene that had already stirred at 25° C. for 30 min. The complete mixture was then stirred at 25° C. for 16 h. The reaction mixture was quenched with saturated NH$_4$Cl solution and extracted with CH$_2$Cl$_2$. The combined organic layers were washed with 2 N HCl, water and saturated NaCl solution. The organic phase was separated and dried over anhydrous sodium sulfate, filtered, and concentrated under reduced pressure to give crude product. The crude product was purified by column chromatography. See FIG. 2.

General Procedure for Deprotection of the N-Boc Precursors (Method D).

To a stirred solution of N-Boc protected compound in dichloromethane was added trifluoroacetic acid (5-10 equiv) dropwise at 0° C. under a nitrogen atmosphere. The reaction mixture was stirred at room temperature for 4-6 h (TLC showed complete deprotection of Boc after 5 h). The solvent and excess of TFA were removed under reduced pressure. The resulting residue was flushed with nitrogen to remove the traces of TFA, and was taken up in 2-3 mL methanol followed by dropwise addition of 2 M NaOH solution in methanol and water (9:1) at 0° C. until the pH reached 9-10. After the reaction mixture stirred for 18 h, the reaction mixture was taken in dichloromethane and evaporated. The resulting residue was purified by column chromatography.

Example 1

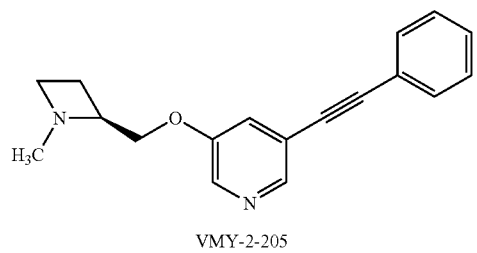

VMY-2-205

Synthesis of (S)-3-((1-methylazetidin-2-yl)methoxy)-5-(phenylethynyl)pyridine (VMY-2-205)

(S)-3-(azetidin-2-ylmethoxy)-5-(phenylethynyl)pyridine (VMY-2-95, 0.12 mmol) was taken up in 2 mL of ethanol. Formalin (37%, 0.3 mL) was added, and the acidity was adjusted to pH 5 with the addition of acetic acid and sodium acetate. The reaction mixture was stirred for 15 min. Sodium cyanoborohydride (0.38 mmol) was added. The whole reaction mixture was allowed to stir for 18 h at room temperature. The solvent was evaporated and the crude product was purified by column chromatography to yield pure VMY-2-205 as a liquid (20 mg, 48%). $^1$H NMR (399 MHz, CDCl3) δ 8.30 (d, J=1.4, 1H), 8.20 (d, J=2.8, 1H), 7.52-7.43 (m, 2H), 7.32-7.28 (m, 3H), 7.25 (dd, J=2.7, 1.7, 1H), 4.06-3.95 (m, 2H), 3.51-3.35 (m, 2H), 2.86 (dd, J=15.9, 8.6, 1H), 2.37 (s, 3H), 2.05 (td, J=8.7, 6.0, 2H). $^{13}$C NMR (100 MHz, CDCl3) δ 154.37, 144.69, 137.72, 131.68, 128.77, 128.41, 123.00, 122.48, 120.53, 92.36, 85.82, 71.57, 66.03, 53.39, 44.85, 20.33. HRMS (ESI): exact mass calcd for $C_{18}H_{18}N_2O$ [M+H]+, 279.149, found 279.1513. As shown in FIG. 22, reverse phase HPLC was performed on Restek's Ultra IBD C18 (5 μm, 4.6×50 mm) using two Shimadzu LC-20AD pumps and a SPD-20A-vis detector set at 330 nm: Method A, 10%-40% acetonitrile in H$_2$O (v/v), flow rate at 1 mL/min over 20 min; method B, 8%-40% methanol in H$_2$O (v/v), flow rate at 1 mL/min over 20 min.

Example 2

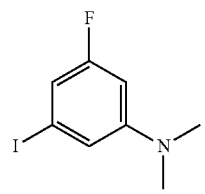

Synthesis of 3-fluoro-5-iodo-N,N-dimethylaniline (VMY-2-119)

The suspension of 1-fluoro-3-iodo-5-nitrobenzene (0.5 g, 1.87 mmol) and SnCl$_2$.2H$_2$O (1.5 g, 6.64 mmol) in EtOH (10 mL) was heated to reflux for 1.5 h. The solvent was removed and the crude mixture was diluted with ether, washed with 4 N NaOH and brine. The ether layer was separated and dried over Na$_2$SO$_4$, filtered, concentrated to yield amine compound as a solid (0.4 g, 91%). The crude product was used without purification.

A solution of above amine (0.4 g, 1.69 mmol) and iodomethane (0.719 g, 5 mmol) in dimethylformamide (DMF; 10 mL) containing potassium carbonate (0.46 g, 3.38 mmol) was stirred for 48 h at room temperature. Water (10 mL) was then added and the solution was extracted with ether three times. The organic extracts washed with water, brine, dried over Na$_2$SO$_4$, filtered and concentrated. The crude product was purified by column chromatography to yield VMY-2-119 as a liquid (0.23 g, 52%). $^1$H NMR (399 MHz) δ 6.69-6.63 (m, 2H), 6.22 (dt, J=12.5, 2.3, 1H), 2.83 (s, 6H). $^{13}$C NMR (100 MHz) δ 163.33 (d, JF-C=245 Hz), 152.49 (d, J=11 Hz) 116.91 (d, J=2.4), 112.12 (d, J=24 Hz), 98.73 (d, J=26 Hz), 94.24 (d, J=11 Hz), 40.21 (s, 3H).

Example 3

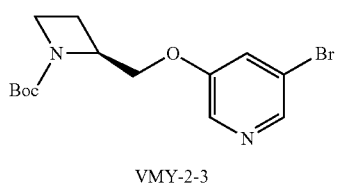 [SMILES: CC(C)(C)OC(=O)N1CC[C@H]1COc1cncc(Br)c1]

(S)-tert-butyl 2-((5-bromopyridin-3-yloxy)methyl)azetidine-1-carboxylate (VMY-2-3)

Method A was used. Yield 55% (white solid). $^1$H NMR (400 MHz, CDCl3) δ 8.25-8.19 (m, 2H), 7.36 (s, 1H), 4.44 (d, J=5.3, 1H), 4.32-4.20 (m, 1H), 4.06 (dd, J=2.8, 10.1, 1H), 3.81 (t, J=7.5, 2H), 2.36-2.14 (m, 2H), 1.36 (s, 9H). $^{13}$C NMR (100 MHz, CDCl3) δ 156.07, 155.41, 143.13, 136.65, 124.02, 120.28, 79.76, 69.00, 59.92, 47.14, 28.37, 18.95. HRMS (ESI): exact mass calcd for $C_{14}H_{19}BrN_2O_3$ [M+H]+, 343.0657, found 343.0670.

Example 4

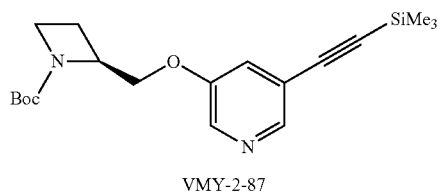 [SMILES: CC(C)(C)OC(=O)N1CC[C@H]1COc1cncc(C#C[Si](C)(C)C)c1]

VMY-2-87

(S)-tert-butyl-2-((5-((trimethylsilyl)ethynyl)pyridin-3-yloxy)methyl)azetidine-1-carboxylate (VMY-2-87)

Yield 62% (Liquid). $^1$H NMR (400 MHz, CDCl3) δ 8.04 (s, 2H), 7.08 (d, 1H), 4.26 (s, 1H), 4.09 (s, 1H), 3.89 (s, 1H), 3.63 (s, 2H), 2.07 (d, 2H), 1.18 (s, 9H), 0.16 (s, 9H). $^{13}$C NMR (100 MHz, CDCl3) δ 156.18, 154.54, 145.22, 138.43, 123.38, 120.54, 101.53, 98.11, 79.76, 68.91, 60.24, 47.27, 28.59, 19.21, 0.28.

Example 5

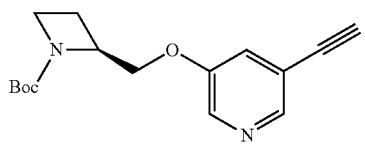 [SMILES: C#Cc1cncc(OC[C@@H]2CCN2C(=O)OC(C)(C)C)c1]

(S)-tert-butyl 2-((5-ethynylpyridin-3-yloxy)methyl)azetidine-1-carboxylate $^1$H NMR (400 MHz, CDCl3) δ 8.36 (s, 2H), 7.35 (s, 1H), 4.65-4.46 (m, 1H), 4.35 (s, 1H), 4.16 (dd, J=2.9, 10.1, 1H), 3.91 (t, J=7.6, 2H), 3.22 (s, 1H), 2.50-2.19 (m, 2H), 1.45 (s, 9H). $^{13}$C NMR (100 MHz, CDCl3) δ 156.12, 155.50, 145.25, 138.47, 123.68, 80.42, 80.15, 79.78, 68.81, 60.00, 47.13, 28.39, 19.03.

Example 6

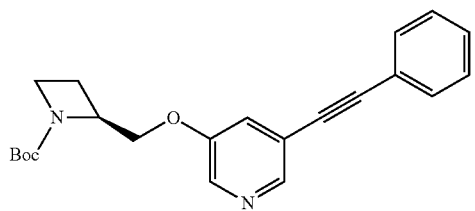

VMY-2-89

(S)-tert-butyl-2-((5-(phenylethynyl)pyridin-3-yloxy)methyl)azetidine-1-carboxylate (VMY-2-89)

Method B in scheme 1 was used. Yield 54% (liquid). ¹H NMR (400 MHz, CDCl3) δ 8.39 (s, 1H), 8.31 (s, 1H), 7.59-7.51 (m, 2H), 7.37 (ddd, J=1.5, 3.4, 5.9, 4H), 4.62-4.44 (m, 1H), 4.36 (s, 1H), 4.16 (dd, J=2.9, 10.1, 1H), 3.90 (t, J=7.6, 2H), 2.51-2.19 (m, 2H), 1.44 (s, 9H). ¹³C NMR (100 MHz, CDCl3) δ 156.12, 154.48, 144.78, 137.91, 131.66, 128.78, 128.41, 122.99, 122.46, 120.58, 92.44, 85.79, 79.75, 68.80, 60.04, 47.00, 28.41, 19.06. HRMS (ESI): exact mass calcd for $C_{22}H_{24}N_2O_3$ [M+H]¹, 365.1870, found 365.1870.

Example 7

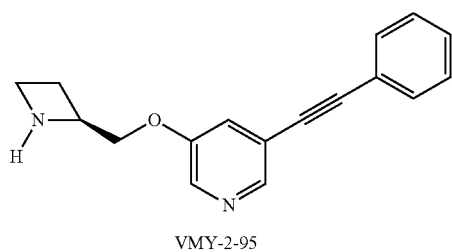 [SMILES: C(#Cc1cncc(OC[C@@H]2CCN2)c1)c1ccccc1]

VMY-2-95

(S)-3-(azetidin-2-ylmethoxy)-5-(phenylethynyl)pyridine (VMY-2-95

Method D was used. Yield 70% (liquid). ¹H NMR (400 MHz, CDCl3) δ 8.37 (s, 1H), 8.31-8.25 (m, 1H), 7.60-7.49 (m, 2H), 7.41-7.29 (m, 4H), 4.33-4.20 (m, 1H), 4.10-3.96 (m, 2H), 3.69 (q, J=7.9, 1H), 3.45 (td, J=4.8, 8.1, 1H), 2.45-2.19 (m, 3H). ¹³C NMR (100 MHz, CDCl3) δ 154.43, 144.56, 137.76, 131.63, 128.75, 128.38, 122.90, 122.43, 120.46, 92.33, 85.85, 72.77, 56.99, 44.20, 23.89. HRMS (ESI): exact mass calcd for $C_{17}H_{16}N_2O$ [M+H]', 265.1341, found 265.1339. Anal. Calcd for $C_{17}H_{16}N_2O$.

Example 8

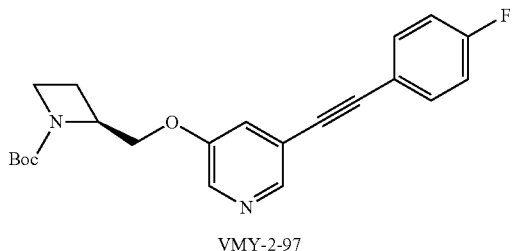 [SMILES: CC(C)(C)OC(=O)N1CC[C@H]1COc1cncc(C#Cc2ccc(F)cc2)c1]

VMY-2-97

(S)-tert-butyl-2-((5-((4-fluorophenyl)ethynyl)pyridin-3-yloxy)methyl)azetidine-1-carboxylate (VMY-2-97)

Method C in Scheme 1 was used. Yield 63% (Liquid). ¹H NMR (400 MHz, CDCl3) δ 8.37 (d, J=1.0, 1H), 8.31 (d, J=2.8, 1H), 7.57-7.50 (m, 2H), 7.40-7.35 (m, 1H), 7.12-7.03 (m, 2H), 4.58-4.50 (m, 1H), 4.36 (s, 1H), 4.16 (dd, J=2.9, 10.1, 1H), 3.90 (t, J=7.6, 2H), 2.53-2.18 (m, 2H), 1.44 (s, 9H). ¹³C NMR (100 MHz, CDCl3) δ 162.72 (d, $J_{F-C}$=250 Hz, C), 156.08, 154.47, 144.66, 137.94, 133.58 (d, $J_{F-C}$=8.4 Hz,), 122.93, 120.38, 118.56 (d, $J_{F-C}$=3.6), 115.72 (d, $J_{F-C}$=22), 91.32, 85.50 (d, $J_{F-C}$=1.3) 79.70, 68.76, 60.02, 47.13, 28.37, 19.0. HRMS (ESI): exact mass calcd for $C_{22}H_{23}FN_2O_3$ [M+H]+, 383.1771, found 383.1767.

Example 9

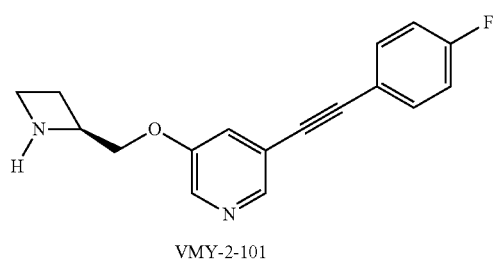 [SMILES: Fc1ccc(C#Cc2cncc(OC[C@@H]3CCN3)c2)cc1]

VMY-2-101

(S)-3-(azetidin-2-ylmethoxy)-5-((4-fluorophenyl)ethynyl)pyridine (VMY-2-101)

Method D was used. Yield 77% (Liquid). ¹H NMR (400 MHz, CDCl3) δ 8.27 (s, 1H), 8.19 (d, J=2.8, 1H), 7.47-7.39 (m, 2H), 7.23 (dd, J=1.5, 2.7, 1H), 7.00-6.93 (m, 2H), 4.20 (s, 1H), 4.04-3.90 (m, 2H), 3.62 (d, J=7.2, 1H), 3.37 (s, 1H), 2.37-2.14 (m, 3H). ¹³C NMR (100 MHz, CDCl3) δ 162.73 (d, $J_{F-C}$=249 Hz, C), 154.45, 144.54, 137.83 133.60 (d, $J_{F-C}$=8.5), 122.88, 120.30, 118.58 (d, $J_{F-C}$=3.5), 115.73 (d, $J_{F-C}$=23 Hz), 91.22, 85.58, 72.84, 57.01, 44.22, 23.92. HRMS (ESI): exact mass calcd for $C_{17}H_{15}FN_2O$ [M+H]+, 283.1247, found 283.1241. Anal. Calcd for $C_{17}H_{15}FN_2O\cdot0.1H_2O$.

Example 10

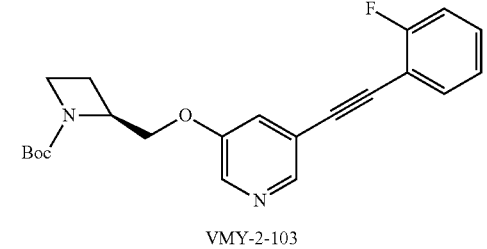 [SMILES: CC(C)(C)OC(=O)N1CC[C@H]1COc1cncc(C#Cc2ccccc2F)c1]

VMY-2-103

(S)-tert-butyl2-((5-((2-fluorophenyl)ethynyl)pyridin-3-yloxy)methyl)azetidine-1-carboxylate (VMY-2-103)

Method C in Scheme 1 was used. Yield 77% (Liquid). ¹H NMR (400 MHz, CDCl3) δ 8.32 (d, J=4.1, 1H), 8.24 (dd, J=2.8, 5.7, 1H), 7.45 (d, J=5.4, 1H), 7.29 (d, J=16.2, 2H), 7.06 (dd, J=9.0, 10.1, 2H), 4.45 (s, 1H), 4.28 (s, 1H), 4.08 (dd, J=3.4, 6.6, 1H), 3.88-3.72 (m, 2H), 2.25 (m, 2H), 1.35 (s, 9H). ¹³C NMR (100 MHz, CDCl3) δ 162.61 (d, $J_{F-C}$=251 Hz C), 156.07, 154.44, 144.74, 138.24, 133.42 (d, $J_{F-C}$=0.9), 130.56 (d, $J_{F-C}$=8.0), 124.03 (d, $J_{F-C}$=3.8), 122.97, 120.16, 115.56 (d, $J_{F-C}$=21 Hz), 111.11 (d, $J_{F-C}$=15 Hz), 90.71 (d, $J_{F-C}$=3.2 Hz), 85.73, 79.70, 68.78, 60.02, 28.37, 47.12, 19.02. HRMS (ESI): exact mass calcd for $C_{22}H_{23}FN_2O_3$ [M+H]$^+$, 383.1771, found 383.1784.

Example 11

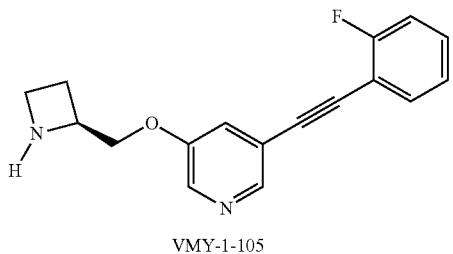 [SMILES: Fc1ccccc1C#Cc1cncc(OC[C@@H]2CCN2)c1]

VMY-1-105

(S)-3-(azetidin-2-ylmethoxy)-5-((2-fluorophenyl)ethynyl)pyridine (VMY-2-105)

Method D was used. Yield 81% (Liquid). $^1$H NMR (400 MHz, CDCl3) δ 8.31 (d, J=1.0, 1H), 8.21 (dd, J=2.7, 0.9, 1H), 7.49-7.41 (m, 1H), 7.31-7.23 (m, 2H), 7.11-7.00 (m, 2H), 4.29-4.14 (m, 1H), 4.05-3.91 (m, 2H), 3.63 (q, J=7.9, 1H), 3.39 (td, J=7.8, 5.0, 1H), 2.41-2.11 (m, 3H). $^{13}$C NMR (100 MHz, CDCl3) δ 162.55 (d, $J_{F-C}$=251 Hz, C), 154.39, 144.49, 138.10, 133.37 (d, $J_{F-C}$=1.0), 130.51 (d, $J_{F-C}$=8.0), 124.00 (d, $J_{F-C}$=3.7), 122.83, 120.03, 115.50 (d, $J_{F-C}$=21 Hz), 111.07 (d, $J_{F-C}$=16 Hz), 90.76 (d, $J_{F-C}$=3.3, 3H), 85.61, 72.76, 56.93, 44.15, 23.82. HRMS (ESI): exact mass calcd for $C_{17}H_{15}FN_2O$ [M+H]+, 283.1247, found 283.1243. Anal. Calcd for $C_{17}H_{15}FN_2O$.

Example 12

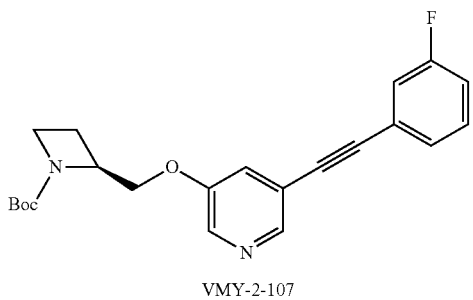 [SMILES: CC(C)(C)OC(=O)N1CC[C@H]1COc1cncc(C#Cc2cccc(F)c2)c1]

VMY-2-107

(S)-tert-butyl2-((5-((3-fluorophenyl)ethynyl)pyridin-3-yloxy)methyl)azetidine-1-carboxylate (VMY-2-107)

Method C in Scheme 1 was used. Yield 48% (Liquid). $^1$H NMR (400 MHz, CDCl3) δ 8.30 (s, 1H), 8.24 (d, J=2.6, 1H), 7.26 (ddd, J=12.6, 8.1, 1.1, 3H), 7.20-7.12 (m, 1H), 7.05-6.94 (m, 1H), 4.45 (s, 1H), 4.29 (s, 1H), 4.08 (dd, J=10.1, 2.8, 1H), 3.82 (t, J=7.5, 2H), 2.41-2.12 (m, 2H), 1.37 (s, 9H). $^{13}$C NMR (100 MHz, CDCl3) δ 162.34 (d, $J_{F-C}$, 246 Hz), 156.15, 154.51, 144.78, 138.25, 130.04 (d, $J_{F-C}$=8.6, 7H), 127.57 (d $J_{F-C}$=3.1), 124.30 (d, $J_{F-C}$=9 Hz) 123.05, 120.10, 118.42 (d, $J_{F-C}$=23 Hz), 116.14 (d, $J_{F-C}$=21 Hz), 91.05 (d, $J_{F-C}$=3.4), 86.65, 79.76, 68.82, 60.05, 47.11, 28.4, 19.05. HRMS (ESI): exact mass calcd for $C_{22}H_{23}FN_2O_3$ [M+H]$^+$, 383.1771, found 383.1778.

Example 13

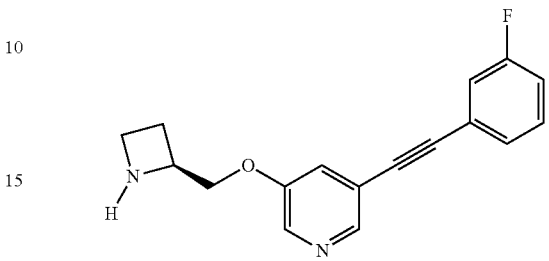

(S)-3-(azetidin-2-ylmethoxy)-5-((3-fluorophenyl)ethynyl)pyridine (VMY-2-109)

Method D was used. Yield 78% (Liquid). $^1$H NMR (399 MHz, CDCl3) δ 8.30 (d, J=1.6, 1H), 8.22 (d, J=2.8, 1H), 7.30-7.23 (m, 3H), 7.20-7.13 (m, 1H), 7.07-6.95 (m, 1H), 4.29-4.15 (m, 1H), 3.98 (qd, J=9.5, 5.5, 2H), 3.65 (q, J=7.9, 1H), 3.46-3.35 (m, 1H), 2.42-2.13 (m, 3H). $^{13}$C NMR (100 MHz, CDCl3) δ 162.33 (d, $J_{F-C}$=246 Hz) 154.46, 144.62, 138.09, 130.01 (d, $J_{F-C}$=9 Hz), 127.56 (d, $J_{F-C}$=3.1 Hz), 124.29 (d, $J_{F-C}$=9 Hz), 123.00, 120.02, 118.42 (d, $J_{F-C}$=23 Hz), 116.12 (d, $J_{F-C}$=21 Hz), 116.02, 90.96 (d, $J_{F-C}$=3.4), 72.84, 57.00, 44.22, 23.92. HRMS (ESI): exact mass calcd for $C_{17}H_{13}FN_2O$ [M+H]$^+$, 283.1247, found 283.1236. Anal. Calcd for $C_{17}H_{13}FN_2O$.

Example 14

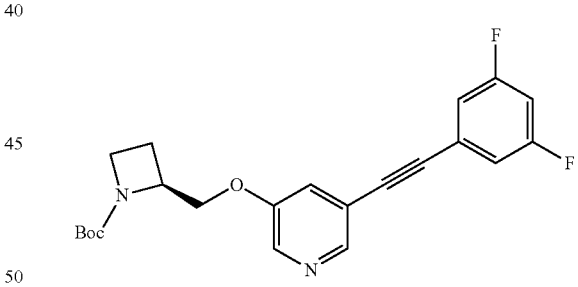

(S)-tert-butyl-2-((5-((3,5-difluorophenyl)ethynyl)pyridin-3-yloxy)methyl)azetidine-1-carboxylate (VMY-2-111)

Method B in Scheme 1 was used. Yield 60% (Liquid). $^1$H NMR (400 MHz, CDCl3) δ 8.30 (s, 1H), 8.26 (d, J=2.8, 1H), 7.30 (s, 1H), 7.02-6.93 (m, 2H), 6.76 (tt, J=8.9, 2.2, 1H), 4.54-4.40 (m, 1H), 4.29 (s, 1H), 4.15-4.03 (m, 1H), 3.82 (t, J=7.6, 2H), 2.40-2.12 (m, 2H), 1.36 (s, 9H). $^{13}$C NMR (100 MHz, CDCl3) δ 163.89 (d, $J_{F-C}$=13 Hz), 161.41 (d, $J_{F-C}$=13 Hz), 156.10, 154.48, 144.76, 138.57, 125.11 (t), 123.03, 119.57, 114.68 (d, $J_{F-C}$=7.7), 114.49 (d, $J_{F-C}$=7.6), 104.90 (t), 89.88, 87.65, 79.73, 68.80, 60.01, 47.11, 28.36, 18.99. HRMS (ESI): exact mass calcd for $C_{22}H_{22}F_2N_2O_3$ [M+H]+, 401.1677, found 401.1692.

Example 15

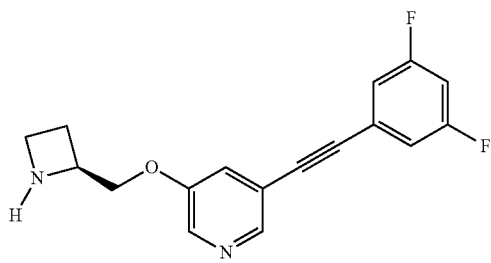 [SMILES: Fc1cc(F)cc(C#Cc2cncc(OC[C@@H]3CCN3)c2)c1]

(S)-3-(azetidin-2-ylmethoxy)-5-((3,5-difluorophenyl)ethynyl)pyridine (VMY-2-113)

Method B in Scheme 1 was used. Yield 79% (liquid). $^1$H NMR (400 MHz, CDCl3) δ 8.29 (d, J=1.6, 1H), 8.24 (d, J=2.8, 1H), 7.25 (dd, J=1.7, 2.8, 1H), 7.03-6.94 (m, 2H), 6.77 (tt, J=2.3, 8.9, 1H), 4.23 (s, 1H), 3.99 (qd, J=5.5, 9.5, 2H), 3.66 (d, J=7.6, 1H), 3.39 (s, 1H), 2.48-1.79 (m, 3H). $^{13}$C NMR (100 MHz) δ 163.91 (d, J$_{F-C}$=13 Hz), 161.43 (d, J$_{F-C}$=13 Hz), 154.47, 144.63, 138.43, 125.13 (t), 123.02, 119.51, 114.71 (d, =8 Hz), 114.51 (d, =7.7), 104.92 (t), 89.83 (t, =3.9), 87.70, 72.90, 56.99, 44.22, 23.9. HRMS (ESI): exact mass calcd for C$_{17}$H$_{15}$FN$_2$O [M+H]+, 301.1152, found 301.1155. Anal. Calcd for C$_{17}$H$_{14}$F$_2$N$_2$O.0.06H$_2$O.

Example 16

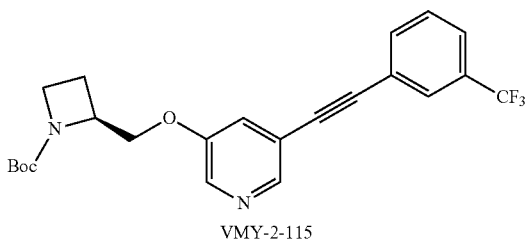 [SMILES: CC(C)(C)OC(=O)N1CC[C@H]1COc1cncc(C#Cc2cccc(C(F)(F)F)c2)c1]

(S)-tert-butyl-2-((5-((3-(trifluoromethyl)phenyl)ethynyl)pyridin-3yloxy)methyl) azetidine-1-carboxylate (VMY-2-115)

Method B in Scheme 1 was used. Yield 50% (Liquid). $^1$H NMR (400 MHz, CDCl3) δ 8.39 (d, J=1.4, 1H), 8.33 (d, J=2.8, 1H), 7.80 (s, 1H), 7.70 (d, J=7.8, 1H), 7.61 (d, J=7.9, 1H), 7.50 (t, J=7.8, 1H), 7.40 (d, J=1.8, 1H), 4.53 (dd, J=5.4, 8.1, 1H), 4.37 (s, 1H), 4.22-4.10 (m, 1H), 3.90 (t, J=7.6, 2H), 2.49-2.17 (m, 2H), 1.55-1.32 (m, 9H). $^{13}$C NMR (100 MHz, CDCl3) δ 156.03, 154.48, 144.66, 138.40, 134.63, 130.90, 128.93, 128.34, 125.17, 123.40, 122.92, 119.79, 90.59, 87.27, 79.59, 68.76, 60.01, 47.13, 28.28, 18.92. HRMS (ESI): exact mass calcd for C$_{23}$H$_{23}$F$_3$N$_2$O$_3$ [M+H]+, 433.1739, found 433.1749.

Example 17

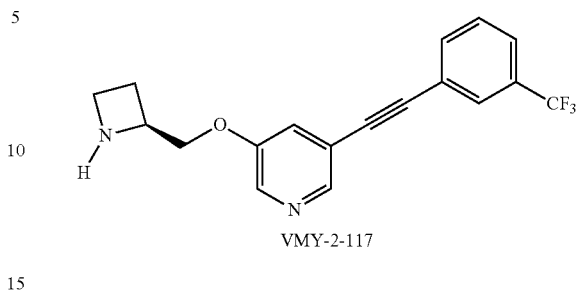

(S)-3-(azetidin-2-ylmethoxy)-5-((3-(trifluoromethyl)phenyl)ethynyl)pyridine (VMY-2-117)

Method D was used. Yield 78% (Liquid). $^1$H NMR (400 MHz, CDCl3) δ 8.31 (d, J=1.6, 1H), 8.24 (d, J=2.8, 1H), 7.74 (s, 1H), 7.64 (d, J=7.7, 1H), 7.55 (d, J=7.9, 1H), 7.43 (t, J=7.8, 1H), 7.27 (dd, J=1.7, 2.8, 1H), 4.23 (td, J=7.5, 12.3, 1H), 3.99 (qd, J=5.5, 9.5, 2H), 3.66 (dd, J=8.1, 15.9, 1H), 3.40 (dt, J=4.9, 7.6, 1H), 2.52-1.90 (m, 3H). $^{13}$C NMR (100 MHz, CDCl3) δ 154.48, 144.63, 138.27, 134.69 (d, J=1.1), 131.06 (q), 128.96, 128.45 (d, J=3 Hz), 125.27 (d, J=3.7), 123.45, 123.01, 119.82, 90.62, 87.32, 72.86, 57.01, 44.22, 23.90. HRMS (ESI): exact mass calcd for C$_{18}$H$_{15}$F$_3$N$_2$O [M+H]+, 333.1215, found 333.1216. Anal. Calcd for C$_{18}$H$_{15}$F$_3$N$_2$O.

Example 18

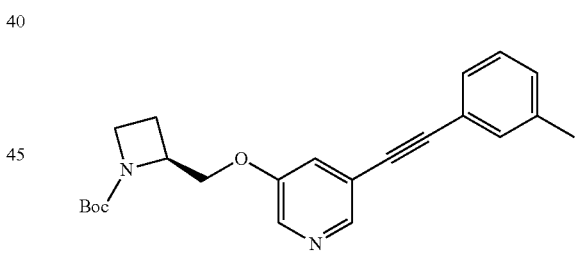

(S)-tert-butyl-2-((5-(m-tolylethynyl)pyridin-3-yloxy)methyl)azetidine-1-carboxylate (VMY-2-121)

Method B was used. Yield 56% (liquid). $^1$H NMR (400 MHz, CDCl3) δ 8.38 (d, J=1.6, 1H), 8.30 (d, J=2.8, 1H), 7.40-7.33 (m, 3H), 7.29-7.24 (m, 1H), 7.19 (d, J=7.6, 1H), 4.59-4.48 (m, 1H), 4.36 (s, 1H), 4.22-4.12 (m, 1H), 3.90 (t, J=7.6, 2H), 2.43-2.33 (s, 3H), 1.44 (s, 9H). $^{13}$C NMR (100 MHz, CDCl3) δ 156.09, 154.47, 144.75, 138.09, 137.81, 132.22, 129.69, 128.73, 128.30, 122.95, 122.25, 120.67, 92.67, 85.45, 79.71, 68.78, 60.05, 47.06, 28.40, 21.18, 19.05. HRMS (ESI): exact mass calcd for C$_{23}$H$_{26}$N$_2$O$_3$ [M+H]+, 379.2022, found 379.2031.

Example 19

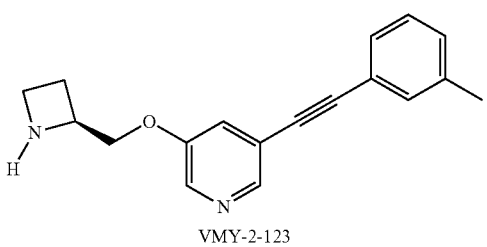 [SMILES: Cc1cccc(C#Cc2cncc(OC[C@@H]3CCN3)c2)c1]

VMY-2-123

(S)-3-(azetidin-2-ylmethoxy)-5-(m-tolylethynyl) pyridine (VMY-2-123)

Method D was used. Yield 68% (Liquid). $^1$H NMR (400 MHz) δ 8.26 (t, J=2.9, 1H), 8.17 (d, J=2.8, 1H), 7.30-7.21 (m, 3H), 7.15 (t, J=7.6, 1H), 7.10-7.05 (m, 1H), 4.24-4.12 (m, 1H), 3.94 (qd, J=9.5, 5.5, 2H), 3.60 (q, J=8.1, 1H), 3.36 (td, J=8.2, 4.4, 1H), 2.44 (s, 1H), 2.35-2.09 (m, 5H). $^{13}$C NMR (100 MHz,) δ 154.43, 144.57, 138.09, 137.67, 132.20, 129.68, 128.73, 128.29, 122.90, 122.23, 120.59, 92.59, 85.49, 72.72, 57.01, 44.19, 23.88, 21.17. HRMS (ESI): exact mass calcd for $C_{18}H_{18}N_2O$ [M+H]+, 279.1497, found 279.1512. Anal. Calcd for $C_{18}H_{18}N_2O \cdot 0.06\ CH_2Cl_2$.

Example 20

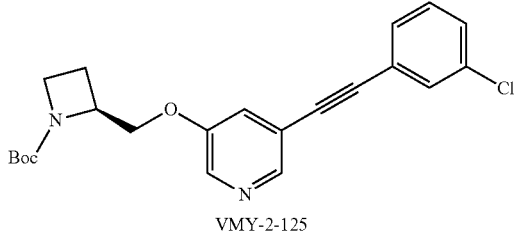 [SMILES: CC(C)(C)OC(=O)N1CC[C@H]1COc1cncc(C#Cc2cccc(Cl)c2)c1]

VMY-2-125

(S)-tert-butyl 2-((5-((3-chlorophenyl)ethynyl)pyridin-3-yloxy)methyl)azetidine-1-carboxylate (VMY-2-125)

Method B was used. Yield 65% (Liquid). $^1$H NMR (400 MHz, CDCl3) δ 8.29 (d, J=1.5, 1H), 8.24 (d, J=2.8, 1H), 7.44 (dd, J=2.5, 0.9, 1H), 7.33 (dt, J=7.4, 1.5, 1H), 7.28 (ddd, J=3.4, 2.4, 1.5, 1H), 7.25 (dd, J=2.0, 1.4, 1H), 7.24-7.18 (m, 1H), 4.56-4.38 (m, 1H), 4.28 (s, 1H), 4.08 (dd, J=10.1, 2.9, 1H), 3.81 (t, J=7.6, 2H), 2.37-2.12 (m, 2H), 1.35 (s, 9H). $^{13}$C NMR (100 MHz, CDCl3) δ 156.08, 154.46, 144.72, 138.24, 134.23, 131.44, 129.74, 129.63, 128.99, 124.16, 122.99, 120.02, 90.86, 86.93, 79.71, 68.78, 60.01, 47.01, 28.38, 19.02. HRMS (ESI): exact mass calcd for $C_{22}H_{23}ClN_2O_3$ [M+H]+, 399.1475, found 399.1456.

Example 21

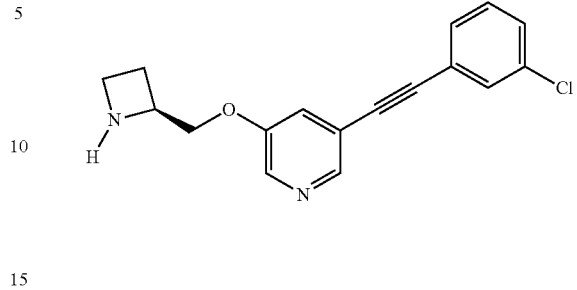

(S)-3-(azetidin-2-ylmethoxy)-5-((3-chlorophenyl) ethynyl)pyridine (VMY-2-127)

Method D was used. Yield 72% (Liquid). $^1$H NMR (400 MHz, CDCl3) δ 8.27 (d, J=1.6, 1H), 8.20 (d, J=2.8, 1H), 7.44 (t, J=1.7, 1H), 7.33 (dt, J=7.4, 1.4, 1H), 7.27-7.17 (m, 3H), 4.26-4.14 (m, 1H), 4.04-3.89 (m, 2H), 3.62 (q, J=8.1, 1H), 3.43-3.32 (m, 1H), 2.38-2.11 (m, 3H). $^{13}$C NMR (100 MHz, CDCl3) δ 154.44, 144.57, 138.09, 134.23, 131.46, 129.75, 129.62, 128.99, 124.16, 122.95, 119.96, 90.78, 86.96, 72.81, 56.98, 44.20, 23.89. HRMS (ESI): exact mass calcd for $C_{17}H_{15}ClN_2O$ [M+H]+, 299.0951, found 299.0965. Anal. Calcd for $C_{17}H_{15}ClN_2O \cdot 0.06H_2O$.

Example 22

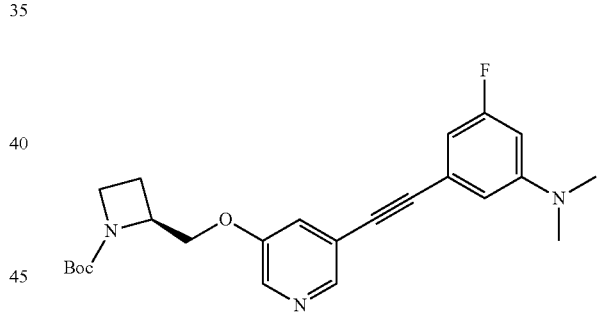

(S)-tert-butyl 2-((5-((3-(dimethylamino)-5-fluorophenyl)ethynyl)pyridin-3-yloxy) methyl)azetidine-1-carboxylate (VMY-2-129)

Method B in Scheme 1 was used. Yield 14% (Liquid). $^1$H NMR (400 MHz) δ 8.35 (s, 1H), 8.27 (s, 1H), 7.35 (s, 1H), 6.60 (s, 1H), 6.54 (d, J=8.7, 1H), 6.37 (dt, J=12.4, 2.2, 1H), 4.49 (s, 1H), 4.33 (s, 1H), 4.19-4.08 (m, 1H), 3.87 (t, J=7.6, 2H), 2.94 (d, J=9.7, 6H), 2.43-2.20 (m, 2H), 1.40 (s, 9H). $^{13}$C NMR (100 MHz) δ 163.55 (d, $J_{F-C}$=241 Hz), 156.14, 154.48, 151.68 (d, $J_{F-C}$=12 Hz), 144.80, 138.00, 123.86 (d, $J_{F-C}$=12 Hz), 123.06, 111.13 (d, $J_{F-C}$=2.0), 106.45 (d, $J_{F-C}$=76 Hz), 100.1 (d, $J_{F-C}$=26 Hz) 92.42 (d, =4.2), 85.17, 79.79, 68.81 (d, $J_{F-C}$=3 Hz), 60.03, 47.01, 40.29, 28.42, 19.07.

Example 23

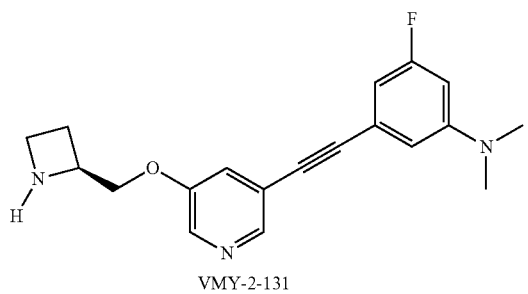 [SMILES: CN(C)c1cc(F)cc(C#Cc2cncc(OC[C@@H]3CCN3)c2)c1]

VMY-2-131

(S)-3-((5-(azetidin-2-ylmethoxy)pyridin-3-yl)ethynyl)-5-fluoro-N,N-dimethylaniline (VMY-2-131)

Method D was used. Yield 72% (Liquid). $^1$H NMR (400 MHz) δ 8.29 (d, J=1.6, 1H), 8.21 (t, J=4.5, 1H), 7.26 (dd, J=2.8, 1.7, 1H), 6.58-6.46 (m, 2H), 6.32 (dt, J=12.5, 2.3, 1H), 4.21 (d, J=15.8, 1H), 3.99 (qd, J=9.5, 5.5, 2H), 3.65 (q, J=7.9, 1H), 3.41 (dd, J=12.0, 8.3, 1H), 2.93-2.85 (s, 6H), 2.40-2.13 (m, 2H), 2.00 (d, J=19.3, 1H). $^{13}$C NMR (100 MHz) δ 206.86 (Acetone, C=O), 163.55 (d, $J_{F-C}$=241 Hz), 154.44, 151.68 (d, $J_{F-C}$=11 Hz), 144.69, 137.89, 123.87 (d, $J_{F-C}$=12 Hz), 123.02, 120.36, 111.12 (d, $J_{F-C}$=2.0, 1H), 105.97 (d, $J_{F-C}$=24 Hz), 100.10 (d, $J_{F-C}$=26 Hz), 92.33 (d, $J_{F-C}$=4 Hz), 85.22, 72.73, 57.06, 44.23, 40.29, 30.88 (Acetone), 23.90. HRMS (ESI): exact mass calcd for $C_{19}H_{20}FN_3O$ [M+H]+, 326.1669, found 326.1668.

As shown in FIG. 22, reverse phase HPLC was performed on Restek's Ultra IBD C18 (5 μm, 4.6×50 mm) using two Shimadzu LC-20AD pumps and a SPD-20A-vis detector set at 330 nm: Method A, 10%-40% acetonitrile in H$_2$O (v/v), flow rate at 1 mL/min over 20 min; method B, 8%-40% methanol in H$_2$O (v/v), flow rate at 1 mL/min over 20 min.

Example 24

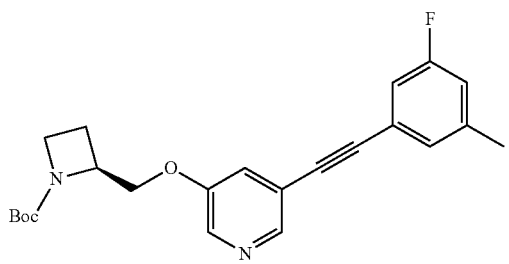 [SMILES: Cc1cc(F)cc(C#Cc2cncc(OC[C@@H]3CCN3C(=O)OC(C)(C)C)c2)c1]

(S)-tert-butyl-2-((5-((3-fluoro-5-methylphenyl)ethynyl)pyridin-3-yloxy)methyl) azetidine-1-carboxylate (VMY-2-133)

Method B in Scheme 1 was use. Yield 65% (liquid). $^1$H NMR (400 MHz, CDCl3) δ 8.28 (d, J=1.5, 1H), 8.22 (d, J=2.8, 1H), 7.28 (dd, J=2.6, 1.7, 1H), 7.06 (d, J=0.5, 1H), 6.94 (dd, J=9.1, 0.5, 1H), 6.80 (d, J=9.5, 1H), 4.51-4.39 (m, 1H), 4.27 (s, 1H), 4.12-4.00 (m, 1H), 3.81 (t, J=7.6, 2H), 2.35-2.09 (m, 5H), 1.35 (s, 9H). $^{13}$C NMR (100 MHz, CDCl3) δ 162.29 (d, $J_{F-C}$=245 Hz, C), 156.10, 151.47, 144.75, 140.56 (d, $J_{F-C}$=8 Hz), 138.13, 128.19 (d, $J_{F-C}$=2.8, 3H), 123.75 (d, $J_{F-C}$=11 Hz), 123.00, 120.19, 116.86 (d, $J_{F-C}$=21 Hz), 115.40 (d, $J_{F-C}$=23 Hz), 91.33 (d, $J_{F-C}$ 3.7), 86.18, 79.73, 68.81, 60.04, 47.20, 28.38, 21.13, 19.03. HRMS (ESI): exact mass calcd for $C_{23}H_{25}FN_2O_3$ [M+H]+, 397.1927, found 397.1929.

Example 25

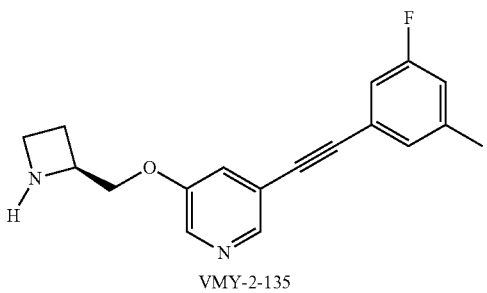 [SMILES: Cc1cc(F)cc(C#Cc2cncc(OC[C@@H]3CCN3)c2)c1]

VMY-2-135

(S)-3-(azetidin-2-ylmethoxy)-5-((3-fluoro-5-methylphenyl)ethynyl)pyridine (VMY-2-135)

Method D was used. Yield 73% (Liquid). $^1$H NMR (400 MHz, CDCl3) δ 8.33 (d, J=1.6, 1H), 8.29-8.24 (m, 1H), 7.29 (dd, J=2.8, 1.7, 1H), 7.12 (dt, J=2.1, 0.7, 1H), 7.05-6.98 (m, 1H), 6.87 (dddd, J=9.6, 2.3, 1.4, 0.7, 1H), 4.28 (tt, J=12.3, 6.2, 1H), 4.03 (qd, J=9.5, 5.5, 2H), 3.70 (dd, J=15.9, 8.2, 1H), 3.45 (ddd, J=7.6, 7.1, 4.4, 1H), 2.43-2.34 (m, 2H), 2.33 (t, J=1.5, 3H), 2.25 (ddd, J=16.4, 11.1, 8.2, 1H). $^{13}$C NMR (100 MHz, CDCl3) δ 162.31 (d, $J_{F-C}$=246.3), 154.44, 144.65, 140.57 (d, $J_{F-C}$=8.6), 138.01, 128.20 (d, $J_{F-C}$=2.7), 123.77 (d, $J_{F-C}$=10.3), 122.98, 120.13, 116.88 (d, $J_{F-C}$=21.1), 115.44 (d, $J_{F-C}$=23.1), 91.26 (d, $J_{F-C}$=3.7), 86.23, 72.78, 57.04, 44.22, 23.88, 21.12. HRMS (ESI): exact mass calcd for $C_{18}H_{17}FN_2O$ [M+H]+, 297.1403, found 297.1403. Anal. Calcd for $C_{18}H_{17}FN_2O \cdot 0.04H_2O$.

Example 26

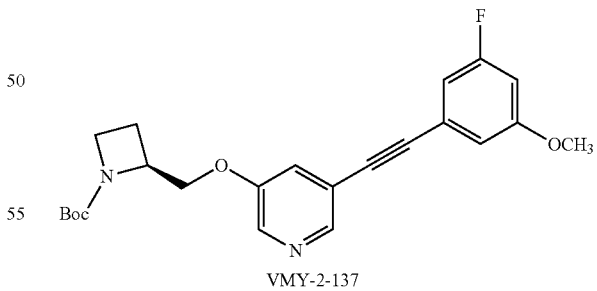

VMY-2-137

(S)-tert-butyl-2-((5-((3-fluoro-5-methoxyphenyl)ethynyl)pyridin-3-yloxy)methyl) azetidine-1-carboxylate (VMY-2-137)

Method B in Scheme 1 was used. Yield 37% (Liquid). $^1$H NMR (400 MHz, CDCl3) δ 8.27 (s, 1H), 8.21 (d, J=2.7, 1H), 7.31-7.24 (m, 1H), 6.74 (ddd, J=1.2, 2.1, 9.9, 2H), 6.54 (dt, J=2.3, 10.6, 1H), 4.47-4.38 (m, 1H), 4.25 (s, 1H), 4.09-4.02 (m, 1H), 3.79 (t, J=7.6, 2H), 3.72 (s, 3H), 2.32-2.13 (m, 2H), 1.32 (s, 9H). $^{13}$C NMR (100 MHz, CDCl3) δ 163.14 (d, $J_{F-C}$=245.8), 160.74 (d, $J_{F-C}$=12.1), 156.13, 154.49, 144.80, 138.27, 124.34 (d, $J_{F-C}$=12.1), 123.07, 120.06, 112.82 (d, $J_{F-C}$=2.9), 110.94 (d, $J_{F-C}$=23.5), 103.22 (d, $J_{F-C}$=25.0), 91.24, 86.33, 79.78, 68.82, 60.03, 55.66, 47.36, 28.40, 19.05. HRMS (ESI): exact mass calcd for $C_{23}H_{25}FN_2O_4$ [M+H]+, 413.1877, found 413.1887.

Example 27

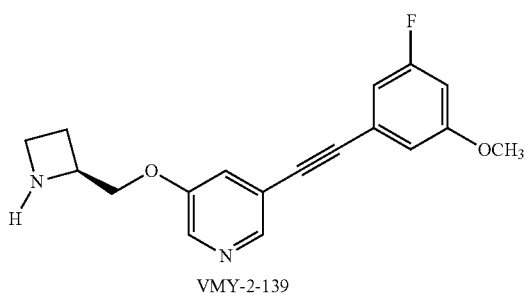 [SMILES: COc1cc(F)cc(C#Cc2cncc(OC[C@@H]3CCN3)c2)c1]

VMY-2-139

(S)-3-(azetidin-2-ylmethoxy)-5-((3-fluoro-5-methoxyphenyl)ethynyl)pyridine (VMY-2-139)

Method D was used. Yield 66% (Liquid). $^1$H NMR (400 MHz, CDCl3) δ 8.29 (d, J=1.6, 1H), 8.22 (d, J=2.8, 1H), 7.25 (dd, J=2.8, 1.7, 1H), 6.83-6.72 (m, 2H), 6.57 (dt, J=10.6, 2.3, 1H), 4.22 (s, 1H), 4.06-3.92 (m, 2H), 3.75 (s, 3H), 3.64 (s, 1H), 3.39 (s, 1H), 2.54-1.91 (m, 3H). $^{13}$C NMR (100 MHz, CDCl3) δ 163.16 (d, =245.6), 160.74 (d, $J_{F-C}$=12.1), 154.48, 144.68, 138.14, 124.37 (d, $J_{F-C}$=12.1), 123.03, 119.99, 112.84 (d, $J_{F-C}$=2.9), 110.97 (d, $J_{F-C}$=23.6), 103.21 (d, $J_{F-C}$=25.0), 91.14 (d, $J_{F-C}$=4.2), 86.40, 72.89, 57.03, 55.68, 44.24, 23.95. HRMS (ESI): exact mass calcd for $C_{18}H_{17}FN_2O_2$ [M+H]+, 313.1352, found 313.1358. Anal. Calcd for $C_{18}H_{17}FN_2O_2 \cdot 0.04H_2O$.

Example 28

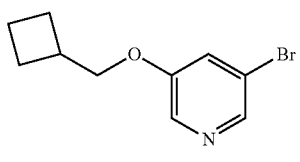

VMY-2-157

3-bromo-5-(cyclobutylmethoxy)pyridine (VMY-2-157)

Method A was used. Yield 69% (Liquid). $^1$H NMR (399 MHz, CDCl3) δ 8.18 (dd, J=11.0, 2.1, 2H), 7.28 (dd, J=2.5, 1.9, 1H), 3.88 (dd, J=6.4, 3.4, 2H), 2.78-2.64 (m, 1H), 2.14-2.02 (m, 2H), 1.99-1.74 (m, 4H). $^{13}$C NMR (100 MHz, CDCl3) δ 155.44, 142.34, 136.33, 123.39, 120.07, 72.30, 34.16, 24.53, 18.40. HRMS (ESI): exact mass calcd for $C_{10}H_{12}BrNO$ [M+H]+, 242.0181; found 242.0181.

Example 29

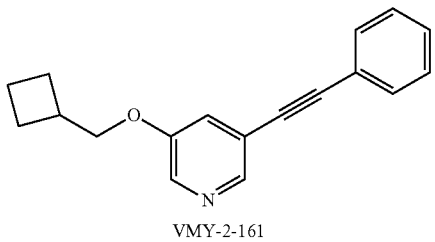 [SMILES: C(#Cc1cncc(OCC2CCC2)c1)c1ccccc1]

VMY-2-161

3-(cyclobutylmethoxy)-5-(phenylethynyl)pyridine (VMY-2-161)

Method B in Scheme 1 was used. Yield 65% (Liquid). $^1$H NMR (400 MHz, CDCl3) δ 8.36 (d, J=1.5, 1H), 8.26 (d, J=2.8, 1H), 7.60-7.50 (m, 2H), 7.40-7.33 (m, 3H), 7.34-7.28 (m, 1H), 3.98 (d, J=6.6, 2H), 2.88-2.73 (m, 1H), 2.23-2.10 (m, 2H), 2.07-1.82 (m, 4H). $^{13}$C NMR (100 MHz, CDCl3) δ 154.72, 144.33, 137.86, 131.67, 128.75, 128.41, 122.86, 122.54, 120.47, 92.24, 85.96, 72.42, 34.41, 24.76, 18.54. HRMS (ESI): exact mass calcd for $C_{18}H_{17}NO$ [M+H]+, 264.1388, found 264.1396. Anal. Calcd for $C_{18}H_{17}NO$.

Example 30

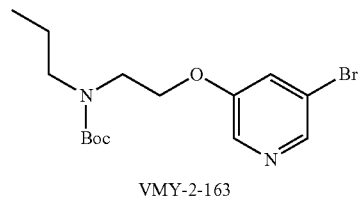 [SMILES: CCCN(CCOc1cncc(Br)c1)C(=O)OC(C)(C)C]

VMY-2-163 tert-butyl-2-(5-bromopyridin-3-yloxy)ethyl(propyl) carbamate (VMY-2-163)

Method A in FIG. 3 was used. Yield 62% (Liquid). $^1$H NMR (400 MHz, CDCl3) δ 8.21 (s, 1H), 8.15 (d, J=2.5, 1H), 7.29 (s, 1H), 4.06 (s, 2H), 3.51 (s, 2H), 3.16 (s, 2H), 1.56-1.43 (m, 2H), 1.39 (s, 9H), 0.82 (t, J=7.4, 3H). $^{13}$C NMR (100 MHz, CDCl3) δ 155.05, 142.72, 136.36, 123.45, 120.14, 79.37, 67.00, 50.40, 46.62, 28.22, 21.84, 11.04. HRMS (ESI): exact mass calcd for $C_{13}H_{23}BrN_2O_3$ [M+H]+, 359.0970; found 359.0978.

Example 31

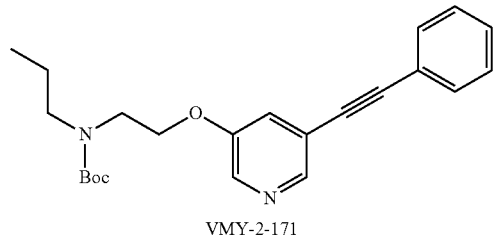 [SMILES: CCCN(CCOc1cncc(C#Cc2ccccc2)c1)C(=O)OC(C)(C)C]

VMY-2-171 tert-butyl-2-(5-(phenylethynyl)pyridin-3-yloxy)ethyl (propyl)carbamate (VMY-2-171)

Method B in Scheme 1 was used. Yield 53% (solid). $^1$H NMR (399 MHz, CDCl3) δ 8.37 (s, 1H), 8.25 (d, J=2.8, 1H), 7.59-7.49 (m, 2H), 7.37-7.28 (m, 4H), 4.14 (s, 2H), 3.59 (s, 2H), 3.25 (s, 2H), 1.64-1.51 (m, 2H), 1.47 (s, 9H), 0.89 (t, J=7.4, 3H). $^{13}$C NMR (100 MHz, CDCl3) δ 155.62, 154.21, 144.55, 137.67, 131.60, 128.73, 128.36, 122.59, 122.41, 120.54, 92.43, 85.79, 79.55, 66.95, 50.56, 46.85, 28.37, 21.95, 11.16. HRMS (ESI): exact mass calcd for $C_{23}H_{28}N_2O_3$ [M+H]+, 381.2187; found 381.2169.

Example 32

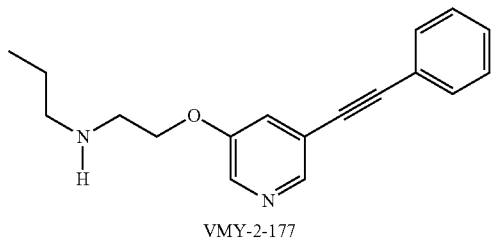 [SMILES: CCCNCCOc1cncc(C#Cc2ccccc2)c1]

VMY-2-177

N-(2-(5-(phenylethynyl)pyridin-3-yloxy)ethyl)propan-1-amine (VMY-2-177)

Method D was used. Yield 87% (solid). $^1$H NMR (400 MHz, CDCl3) δ 8.29 (d, J=1.5, 1H), 8.19 (d, J=2.8, 1H), 7.50-7.41 (m, 2H), 7.33-7.26 (m, 3H), 7.26-7.22 (m, 1H), 4.05 (t, J=5.2, 2H), 2.96 (t, J=5.2, 2H), 2.58 (t, J=7.2, 2H), 1.47 (td, J=14.6, 7.3, 3H), 0.87 (t, J=7.4, 3H). $^{13}$C NMR (100 MHz, CDCl3) δ 154.38, 144.64, 137.70, 131.65, 128.77, 128.39, 122.83, 122.45, 120.53, 92.37, 85.83, 68.05, 51.72, 48.51, 23.18, 11.70. HRMS (ESI): exact mass calcd for $C_{18}H_{20}N_2O$ [M+H]+, 281.1654, found 281.1645. Anal. Calcd for $C_{18}H_{20}N_2O$.

Example 33

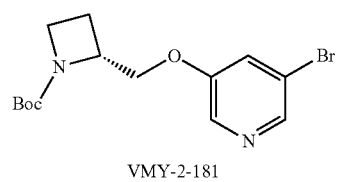 [SMILES: CC(C)(C)OC(=O)N1CC[C@@H]1COc1cncc(Br)c1]

VMY-2-181

(R)-tert-butyl 2-((5-bromopyridin-3-yloxy)methyl)azetidine-1-carboxylate (VMY-2-181)

Method A in FIG. 3 was used. Yield 30% (solid). $^1$H NMR (400 MHz, CDCl3) δ 8.20 (d, J=2.4, 2H), 7.35 (t, J=1.9, 1H), 4.48-4.40 (m, 1H), 4.26 (s, 1H), 4.05 (dd, J=10.1, 2.7, 1H), 3.86-3.76 (m, 2H), 2.70-2.01 (m, 2H), 1.35 (s, 9H). $^{13}$C NMR (100 MHz, CDCl3) δ 156.06, 155.41, 143.10, 136.62, 124.04, 120.28, 79.75, 69.00, 59.91, 47.08, 28.36, 18.94. HRMS (ESI): exact mass calcd for $C_{14}H_{19}BrN_2O_3$ [M+H]+, 343.0657, found 343.0680.

Example 34

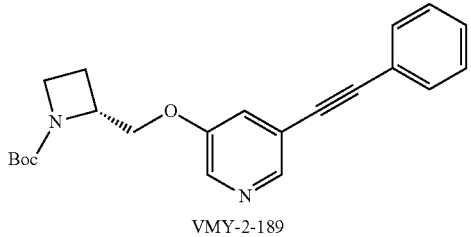 [SMILES: CC(C)(C)OC(=O)N1CC[C@@H]1COc1cncc(C#Cc2ccccc2)c1]

VMY-2-189

(R)-tert-butyl-2-((5-(phenylethynyl)pyridin-3-yloxy)methyl)azetidine-1-carboxylate (VMY-2-189)

Method B in Scheme 1 was used. Yield 74%. $^1$H NMR (400 MHz, CDCl3) δ 8.31 (s, 1H), 8.23 (s, 1H), 7.52-7.41 (m, 2H), 7.36-7.24 (m, 4H), 4.45 (d, J=5.4, 1H), 4.28 (s, 1H), 4.08 (dd, J=10.2, 2.6, 1H), 3.82 (t, J=7.6, 2H), 2.28 (ddd, J=25.0, 14.3, 7.1, 2H), 1.36 (d, J=0.5, 9H). $^{13}$C NMR (100 MHz, CDCl3) δ 156.12, 154.50, 144.75, 137.86, 131.66, 128.78, 128.40, 123.04, 122.46, 120.63, 92.46, 85.77, 79.76, 68.81, 47.01, 60.05, 28.41, 19.06. HRMS (ESI): exact mass calcd for $C_{22}H_{24}N_2O_3$ [M+H]+, 365.1865, found 343.1893.

Example 35

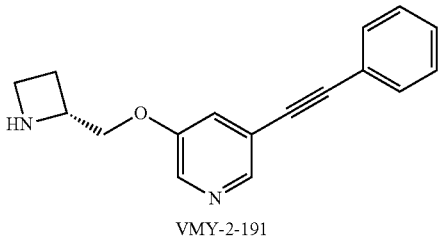 [SMILES: C(#Cc1cncc(OC[C@H]2CCN2)c1)c1ccccc1]

VMY-2-191

(R)-3-(azetidin-2-ylmethoxy)-5-(phenylethynyl)pyridine (VMY-2-191)

Method D was used. Yield 75% (Liquid). $^1$H NMR (399 MHz, CDCl3) δ 8.28 (s, 1H), 8.19 (d, J=2.8, 1H), 7.51-7.42 (m, 2H), 7.27 (ddd, J=10.0, 6.0, 0.8, 4H), 4.26-4.14 (m, 1H), 3.96 (qd, J=9.5, 5.7, 2H), 3.62 (q, J=8.0, 1H), 3.38 (td, J=8.1, 4.4, 1H), 2.38-2.12 (m, 3H). $^{13}$C NMR (100 MHz, CDCl3) δ 154.45, 144.61, 137.76, 131.66, 128.77, 128.40, 122.96, 122.46, 120.51, 92.35, 85.84, 72.78, 57.03, 44.22, 23.91. HRMS (ESI): exact mass calcd for $C_{17}H_{16}N_2O$ [M+H]+, 265.1341, found 265.1349. Anal. Calcd for $C_{17}H_{16}N_2O \cdot 0.6H_2O$.

Example 36

(S)-3-(azetidin-2-ylmethoxy)-5-phenylpyridine (VMY-2-203)

This compound was prepared according to the method shown in FIG. 3. To a solution of (S)-tert-butyl-2-((5-bromopyridin-3-yloxy)methyl)azetidine-1-carboxylate (1, 0.58 mmol) in 9 mL of toluene and 3 mL of ethanol was added phenyl boronic acid (0.69 mmol) followed by 2 mL of 2 M $Na_2CO_3$ and tetrakis(triphenylphosphine)palladium (0) (0.03 mmol). The reaction was stirred for 12 h at 90° C. under nitrogen. The reaction was cooled to room temperature, diluted with water and extracted three times with ethyl acetate. The combined organic layers dried over anhydrous sodium sulfate, filtered and concentrated in vacuo to afford a crude product, which was subsequently purified by column chromatography. The resulting pure compound was subjected to Boc deprotection followed by purification of column chromatography to yield a final pure compound VMY-2-203 as a liquid (70 mg, 71%). $^1$H NMR (400 MHz, $CDCl_3$): δ 8.37 (d, J=1.7, 1H), 8.22 (d, J=2.7, 1H), 7.49 (dd, J=5.1, 3.8, 2H), 7.38 (t, J=7.6, 2H), 7.31 (ddd, J=7.7, 4.1, 0.5, 2H), 4.31-4.14 (m, 1H), 4.02 (qd, J=9.5, 5.6, 2H), 3.63 (q, 0.1=8.0, 1H), 3.39 (td, 0.1=8.2, 4.4, 1H), 2.39-2.13 (m, 3H). $^{13}$C NMR (100 MHz, $CDCl_3$) δ 155.1, 140.7, 137.6, 137.2, 136.5, 128.9, 128.1, 127.1, 119.7, 72.8, 57.1, 44.2, 24.0. HRMS (ESI): exact mass calcd for $C_{15}H_{16}N_2O$ $[M+H]^+$, 241.1341, found. 241.1348 Anal. Calcd for $C_{15}H_{16}N_2O\cdot0.6H_2O$. $[\alpha]_D^{25.5}=-4.69$ (c=1.4, $CHCl_3$).

Example 37

The in vitro binding affinities of the new ligands were measured for defined receptor subtypes (α2β2, α2β4, α3β2, α3β4, α4β2, α4β4, α6β2, α6β4, and α7) expressed in stably transfected cell lines. [$^3$H]Epibatidine ([$^3$H]EB) binds to the agonist recognition site of all of the defined receptor subtypes with high affinities. Rat forebrain homogenates were included to allow comparison between the heterologous and native α4β2 and α7 nAChRs. See FIG. 18 for binding affinity values ($K_i$) of the ligands at the three major nAChR subtypes (α3β4, α 4β32, and α7).

TABLE 1

In Vitro Pharmacological Properties of Nicotinic Ligands

| Compound | $K_i$ (nM) | | | $IC_{50(10')}$ (nM) | |
|---|---|---|---|---|---|
| | α3β4 | α4β2 | α7 | α3β4 | α4β2 |
| Sazetidine-A | 1,900 | 0.062 | 1,600 | >10,000 | 7.5 |
| VMY-2-95 | 650 | 0.049 | 580 | | 16 |
| VMY-2-101 | 650 | 0.083 | 2,000 | | 8 |
| VMY-2-105 | 580 | 0.072 | 1,100 | | 20 |
| VMY-2-109 | 520 | 0.032 | 720 | | 13 |
| VMY-2-113 | 1,400 | 0.05 | 1,800 | | |
| VMY-2-117 | 1,400 | 0.26 | 1,300 | | |
| VMY-2-123 | 4,000 | 0.046 | 200 | | |
| VMY-2-127 | 3,400 | 0.093 | 480 | | |
| VMY-2-131 | 1,000 | 0.031 | 250 | | |
| VMY-2-135 | 1,100 | 0.043 | 590 | | |
| VMY-2-139 | 1,300 | 0.076 | 1,500 | | |
| VMY-2-161 | 1,300,000 | 160,000 | 410,000 | >100,000 | 35,000 |
| VMY-2-177 | 850,000 | 1,100 | 48,000 | 12,000 | 15,000 |
| VMY-2-191 | 1,700 | 0.11 | 1,600 | 21,000 | 16,000 |
| VMY-2-205 | 40,000 | 1.2 | 7,700 | 22,000 | 370 |

Example 38

Functional properties of the new ligands were determined by $^{86}Rb^1$ efflux assays in cells expressing α3β4 and α4β2 nAChR subtypes. Functional activity of each new ligand was measured in terms of its agonism, antagonism and desensitization ability.

Agonist activity of each of the ligands was tested at eight concentrations. The responses were compared to that stimulated by 100 μM (−)-nicotine, a near maximally effective concentration. The full concentration-effect curves generated potency ($EC_{50}$) and efficacy ($E_{max}$) of each ligand. The antagonist activity of each new compound was determined by applying the compound to cells simultaneously with 100 μM (−)-nicotine.

Each compound was tested for antagonist activity at eight concentrations. The potency ($IC_{50(0')}$) of each ligand as an antagonist was derived from the full concentration-effect curves.

The desensitization potency of each ligand was determined by pre-treating cells with the test compound for 10 minutes before 100 μM (−)-nicotine was applied. The potency of a compound to desensitize the receptor after a 10 minute exposure ($IC_{50(10')}$) was obtained with full concentration-effect curves using at least eight concentrations of the ligand. Though the $^{86}Rb^+$ efflux assays were the main methodology used to determine functional properties, whole-cell current measurements were also used to verify the key experiments. See Table 1 for potency of the compounds to desensitize the two major receptor ($IC_{50(10')}$) subtypes, α3β34 and α4β2.

Example 39

Figure 5:
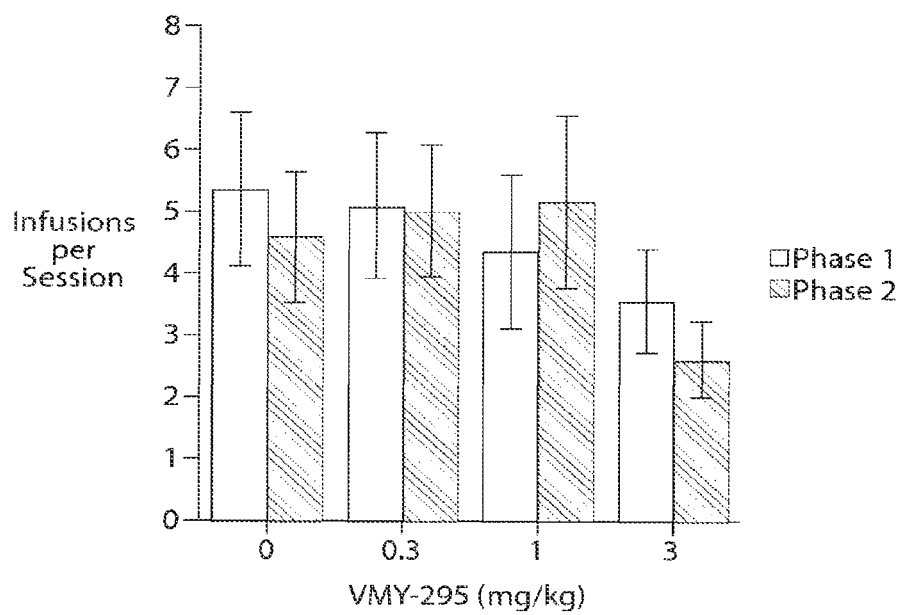
FIG. 5 is a graph depicting acute VMY-2-95 effects on nicotine self-administration in rats.
Figure 6:
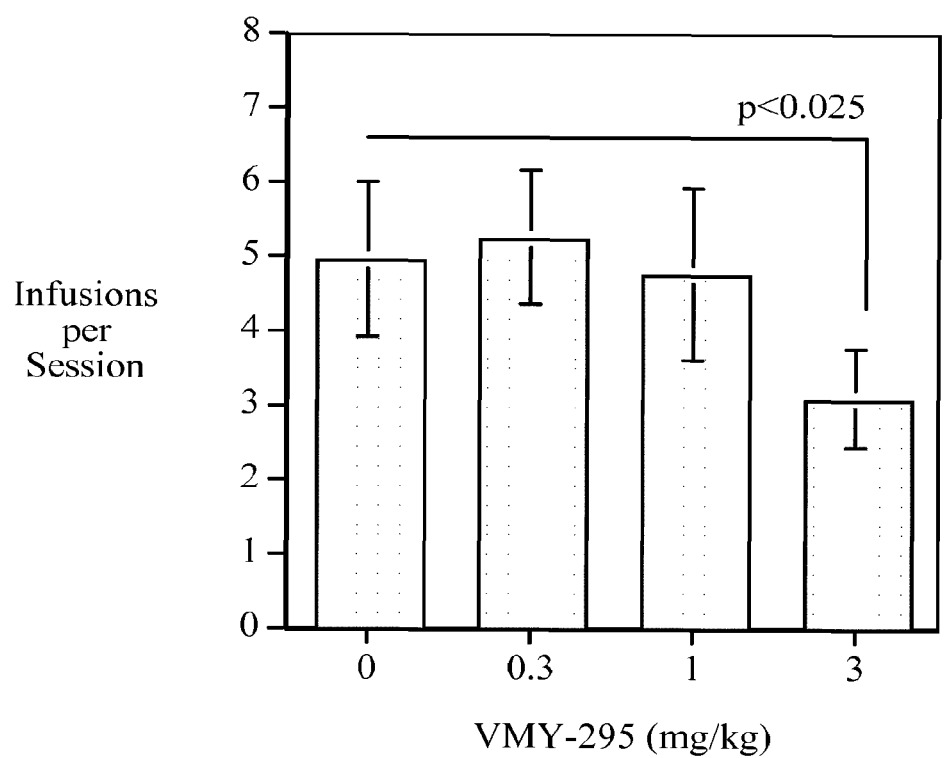
FIG. 6 is a graph depicting acute VMY-2-95 mean effects on nicotine self-administration in rats.

Preliminary studies of VMY-2-95 in animal models indicate that the compound may be effective in reducing nicotine and ethanol self-administration. Previous studies have shown that Sazetidine-A, a selective α4β2 nicotinic receptor-desensitizing agent, was effective at reducing nicotine self-administration in rats, with lowest effective dose of 3 mg/kg administered subcutaneously (sc). In this example, VMY-2-95 was assessed for efficacy in reducing nicotine self-administration in young adult female Sprague-Dawley rats (N=15). Before the start of nicotine self-administration sessions, all animals were trained to lever press in a standard dual-lever operant chamber for food reinforcement. After food training, the animals were surgically implanted with jugular catheters. Animals had an initial ten session of nicotine (0.03 mg/kg FRI) self-administration prior to VMY-2-95 delivery. VMY-2-95 was delivered with acute sc injections 10 minutes before the start of 45 minute nicotine sessions in a repeated measures counterbalanced design at one of three doses: 0.3, 1, and 3 mk/kg, or saline vehicle. Alpha of p<0.05 (two-tailed) was used as the threshold for significance. Results are shown in FIG. 5 and FIG. 6.

The 3 mg/kg dose significantly reduced nicotine self-administration in the rats relative to the saline vehicle (p<0.025); however, the lower doses studied did not produce significant decreases. VMY-2-95 showed similar potency as Sazetidine-A. The effect of VMY-2-95 appeared to become more pronounced during the second phase (see FIG. 5).

Example 40

Computational Studies.

To study (S)-(−)-nicotine and (R)-(−)-deschloroepibatidine binding with the α4β2 nAChR in atomic detail, a structural model of the LSD of human α4β2 nAChR was built by using the Homology Model software MODELLERX9.10. The reference template is the x-ray crystal structure of the AChBP (PDB entry of 1UW6) and the rat α4β2 x-ray structure (PDB: 1OLE). Multiple sequence alignment was generated by Psi-BLAST and ClusterW. Upon construction of the model, appropriate ionization states were maintained, the side chains were relaxed to remove possible side chain atom contacts with the neighboring residues, different rotamer states of the residue were assigned, and then local side chain atom dynamics followed by minimization were performed. Minimization and Molecular dynamics simulations were carried out using the SANDER module of AMBER 10.0 with default parameters. The homology modeled structure was validated with PROCHECK and WHATIF program.

Molecular docking was carried out using SurFlexDock Module of Sybyl-X (Tripos Inc. St. Louis, USA). However, to be consistent with the nicotine structural conformation (PDB: 1UW6), a manual intervention followed by constrained molecular dynamics simulations were carried out. This procedure was applied to VMY-2-95, Varinicline and Sazetidine A. The α4β2 nAChR compound complexes were refined by molecular dynamics simulation using the Amber 10.0 with the PARM98 force-field parameter. The charge and force field parameters of the compounds were obtained using the most recent Antechamber module in the Amber 10.0 (4), where compounds were minimized at the MP2/6-31G* level using Gaussian 09. The SHAKE algorithm was used to keep all bonds involving hydrogen atoms rigid. Weak coupling temperature and pressure coupling algorithms were used to maintain constant temperature and pressure, respectively. Electrostatic interactions were calculated with the Ewald particle mesh method with a dielectric constant at $1R_{ij}$ and a nonbonded cutoff of 12 Å for the real part of electrostatic interactions and for van der Waals interactions. The total charge of the system was neutralized by addition of a chloride ion. The system was solvated in a 12 Å cubic box of water where the TIP3P model was used. 5000 steps of minimization of the system were performed in which the α4β2 nAChR was constrained by a force constant of 75 kcal/mol/Å. After minimization, a 20 ps simulation was used to gradually raise the temperature of the system to 298 K while the complex was constrained by a force constant of 20 kcal/mol/Å. Another 20 ps equilibration run was used where only the backbone atoms of the complex were constrained by a force constant of 5 kcal/mol/Å. Final production run of 200 ps was performed with no constraints. When applying constraints, the initial complex structure was used as a reference structure. The PME method was used and the time step was 5 fs, and a neighboring pairs list was updated every 25 steps.

Binding Affinities for nAChR Subtypes.

The binding affinities of all compounds synthesized for the receptor subtypes were examined in binding competition studies against [$^3$H]-epibatidine. $K_i$ values of these compounds at seven defined subtypes of rat nAChRs and native nAChRs from rat forebrain are provided in FIGS. 14 and 15.

Figure 14:
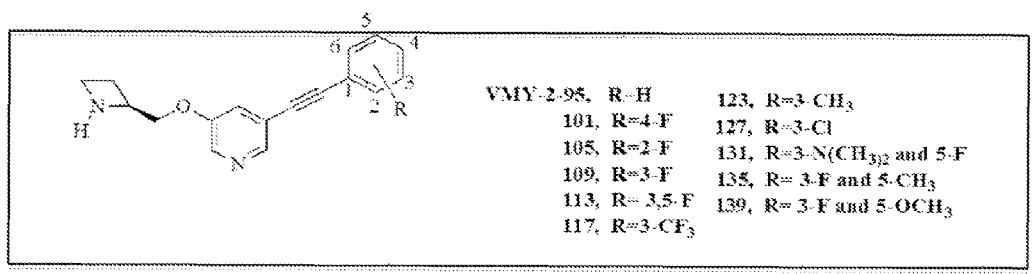
FIG. 14 shows a comparison of binding affinities of series 1 compounds for rat nAChR subtypes with those of Saz-A, varenicline and nicotine.

All compounds in series 1 exhibited high affinity for the rat α4β2 nAChR subtype with $K_i$ values ranging from 0.031 nM (VMY-2-131) to 0.26 nM (VMY-2-117). These compounds also showed high affinities for the two other subtypes containing β2 subunits, α2β2 and α3β2 nAChRs. In contrast, the binding affinities of these compounds for nAChR subtypes containing β4 subunits are much lower than those for their β2 containing counterparts. As shown in FIGS. 14 and 15, the selectivity of these compounds for α4β2 receptors over α3β4 receptors ($K_i$ ratio) were very high, ranging from 5,400 times (VMY-2-117) to 87,000 times (VMY-2-123), much greater than that of nicotine or varenicline. Similar to the low affinities for α3β4 receptors, these compounds showed very low affinities for α7 homomeric receptors.

After VMY-2-95 showed a promising binding profile, we synthesized a few of its analogs to understand consequences of substitutions on the benzene ring. We had substitutions at position 2, 3 or 4 to generate VMY-2-101, 105, 109, 123 and 127. These singly substituted analogs have binding profiles similar to that of VMY-2-95 (FIG. 14). The dual substituted analogs, VMY-2-113, 131, 135 and 139, also showed high affinities and selectivity for α4β2 receptors. However, the installation of $CF_3$ at position 3 decreased the binding affinity for the α4β2 receptor, as shown by the binding profile of VMY-2-117.

Interestingly, two compounds of series 2, VMY-2-161 (azetidine replace with cyclobutane) and VMY-2-177 (ring opened analogue of azetidine), showed very low binding affinities to nAChRs (FIG. 15), indicating that the azetidine ring is important for the high affinity and selectivity binding profile. In addition, the (S)—N-methyl compound VMY-2-205 binds nearly 25 times weaker than the corresponding (S)—N—H VMY-2-95, suggesting that N—H provides a potentially important H-bond interaction. For comparing the difference between stereotypes, VMY-2-191, which is the (R)-form of VMY-2-95, was synthesized. The binding profile of VMY-2-191 is similar to that of VMY-2-95, though VMY-2-191 has a slightly lower affinity for α4β2 receptors than VMY-2-95.

Binding Affinities for Targets Other than nAChRs.

To determine affinities of the lead compound, VMY-2-95, for targets other than neuronal nAChRs, we tested VMY-2-95 in binding assays using 41 other targets, including many CNS receptors and transporters. As shown in FIG. 18, the preliminary binding assays using a single concentration of VMY-2-95 at 10 μM generated 32 "miss" (less than 50% inhibition of bindings by specific labeled ligands) and 9 "hit" (more than 50% inhibition of bindings). The Ki values of VMY-2-95 at these 9 targets were determined by performing secondary binding assays using a series of concentrations of VMY-2-95. As shown in FIG. 19, the compound has low binding affinities for these targets. Furthermore, the binding affinity of VMY-2-95 for α4β2 nAChRs is at least 3,000 times higher than that for any of those 9 targets.

Effects of VMY-2-95 on Functions of nAChRs

The functional effect of the lead compound, VMY-2-95, was assessed by measuring agonist-stimulated $^{86}Rb^+$ efflux from stably transfected cells expressing nAChRs, either human α4β2 subtype or rat 03134 subtype. Its ability to desensitize nAChRs was determined by measuring nicotine-stimulated $^{86}Rb^+$ efflux after cells were preincubated with VMY-2-95 for 10 min. For comparison, we also examined three other nicotinic ligands in the same manner, Sazetidine-A, varenicline and (–)-nicotine.

As shown in FIG. 17, VMY-2-95 did not show any detectable agonist activity at rat α3β4 nAChRs. At human α4β2 receptors, the compound showed clear agonist activity with $EC_{50}$ value as 8.6 nM. However, its efficacy for activating the α4β2 receptors is very low, only 26% of the maximal stimulation by nicotine. In the parallel experiments, varenicline showed near-full agonist activity at α3β4 nAChRs but partial agonist activity at α4β2 receptors.

It is important to note that all four compounds studied, VMY-2-95, Sazetidine-A, varenicline and nicotine, inhibited nicotine activation of α4β2 receptors after preincubated with the cells for 10 min. As shown in FIG. 17, VMY-2-95 potently desensitized 414132 receptor function with an $IC_{50(10''')}$ value of 16 nM, which is similar to that of Sazetidine-A but significantly lower than those of varenicline and nicotine. In contrast, the $IC_{50(10''')}$ value of VMY-2-95 in desensitizing α3β4 nAChRs was higher than 10,000 nM, which is more than 600 times higher than its $IC_{50(10''')}$ value in desensitizing α4β2 nAChRs.

Effects of VMY-2-95 on Nicotine Self-Administration in Rats.

We studied acute effects of VMY-2-95 on nicotine self-administration in rats. As shown in FIG. 6, VMY-2-95 significantly (F(3,42)=3.36, p<0.05) decreased intravenous nicotine self-administration in a dose-dependent manner. The 3 mg/kg dose of VMY-2-95 caused a significant (p<0.025) decrease in the number of nicotine infusions compared with vehicle. However, at the two lower doses studied (0.3 and 1 mg/kg), VMY-2-95 did not produce significant effects. The effects of VMY-2-95 appeared to become more pronounced during the second phase of treatment (Data not shown). These data demonstrate that similar to Saz-A, VMY-2-95 at 3 mg/kg effectively reduces nicotine self-administration in rats (Levin et al., 2010).

It is interesting that the locomotor activity of rats was significantly increased at the three doses of VMY-2-95 tested (FIG. 10). Therefore, it is highly unlikely the effect of VMY-2-95 in decreasing nicotine self-administration is resulted from a sedative effect. Furthermore, the data indicate that the effect in locomotor activities does not correlate to the effect in nicotine self-administration, as the peak of increased locomotor activity was at 1 mg/kg, at which there was no significant reduction of nicotine self-administration.

Binding Affinities for Targets Other than nAChRs

To determine affinities of the lead compound, VMY-2-95, for targets other than neuronal nAChRs, we tested VMY-2-95 in binding assays using 41 other targets, including many CNS receptors and transporters. As shown in FIG. 18, the preliminary binding assays using a single concentration of VMY-2-95 at 10 μM generated 32 "miss" (less than 50% inhibition of bindings by specific labeled ligands) and 9 "hit" (more than 50% inhibition of bindings). The $K_i$ values of VMY-2-95 at these 9 targets were determined by performing secondary binding assays using a series of concentrations of VMY-2-95. As shown in FIG. 19, the compound has low binding affinities for these targets. Furthermore, the binding affinity of VMY-2-95 for (14132 nAChRs is at least 3,000 times higher than that for any of those 9 targets.

Comparison of Molecular Recognition of VMY-2-95 by Receptor in Structural Models with Those of Nicotine, Varenicline and Saz-A.

Figure 9:
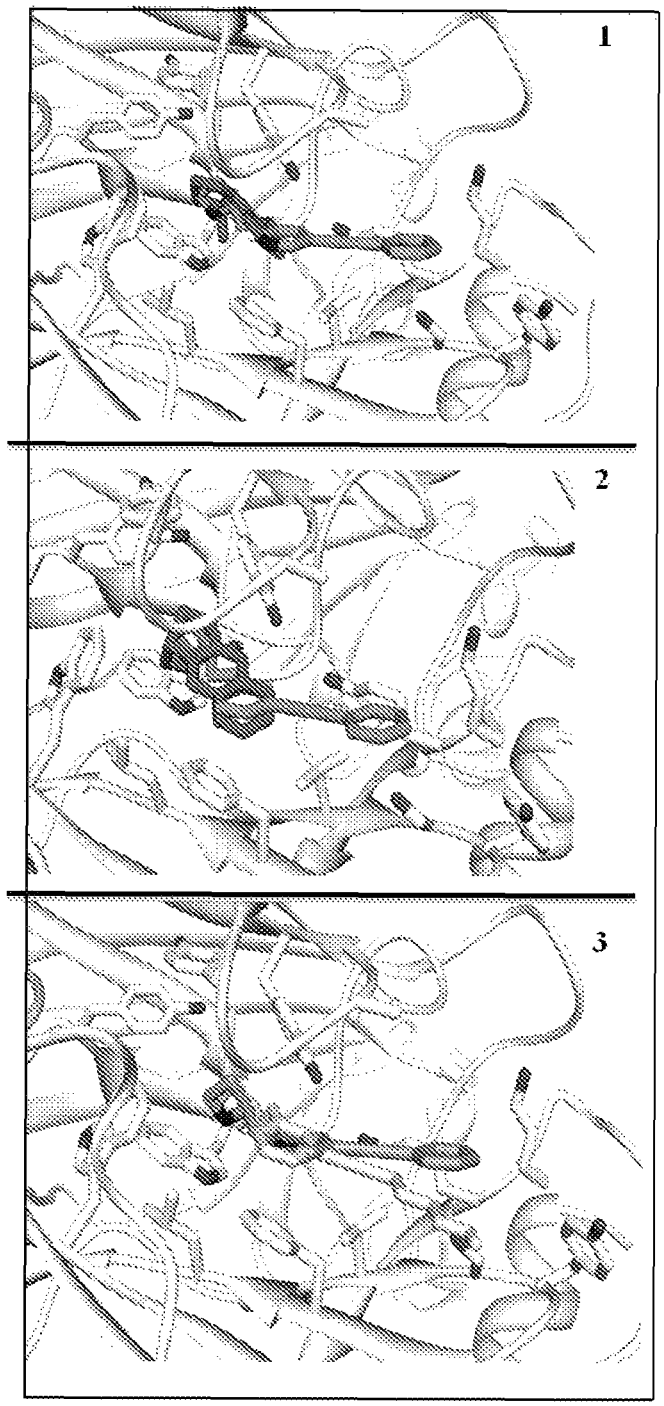
FIG. 9 Molecular modeling overlay of VMY-2-95 (colored green) with (−)-nicotine (1) varenecline (2) saz-A (3) in the α4β2 nAChR binding site. Residues are labeled and shown in a stick model rendering.

To better understand the binding interactions between α4β2 nAChR and VMY-2-95, molecular models of VMY-2-95 with the α4β2 nAChRs were constructed (FIG. 8), and overlaid with (−)-nicotine, varenicline, and saz-A (FIG. 9). The docked structural models of the α4β2 nAChR/ligand complex reveal that the binding mode interactions are slightly different from one another as reported. To provide a consistent model with the nicotine-AChBP (PDB: 1UW6), the docked positions of compounds were remodeled using a step-by-step manual docking methodology with restrained molecular dynamics (MD) simulations followed by energy minimization. In the restrained MD simulations, the optimum van der Waals and H-bond distance constraints was set between the ligand and the α4β2 nAChR ligand binding domain residues. The final binding complex is depicted in FIGS. 8 and 9.

VMY-2-95, (−)-nicotine, varenicline and Saz-A are buried at the aromatic rich residues such as W147α, W55β, Y91α, Y188α, Y195α, and F117β (FIGS. 8 and 9) and occupied a similar binding region. However, the relative orientations of the compounds in the α4β2 nAChR binding site were slightly different. This may be due to conformational adjustments inside the binding site. The azetidine group in saz-A and VMY-2-95 forms stacking interactions with the amino acid W147α (FIGS. 8 and 9). However, the pyridine ring occupies a slightly different position to compensate for the conformational entropy penalty due to isomeric constraints. The hydroxy group of saz-A forms a hydrogen bond with Y188α whereas this residue forms hydrogen bond with the pyrazine ring nitrogen of varenicline, and this hydrogen bond is absent in (−)-nicotine. VMY-2-95, and saz-A have hydrophobic groups extending from the pyridine ring, forming additional favorable hydrophobic interactions with K76β, K77β, Y112β, V109β, F117β, and L119β. These interactions can be compared with the interactions of varenicline involving V109β, F117β, and L119β (FIGS. 8 and 9). Although saz-A and VMY-2-95 have a similar pattern of interaction, the benzene ring of the ethynylbenzene of VMY-2-95 form a stronger stacking and lipophilic interaction with K76β, K77β, Y112β, and V109β than the corresponding hex-5-yn-1-ol group of saz-A. Moreover, the 3-(2-phenylethynyl) pyridine group of VMY-2-95 is more rigid and may require a smaller penalty in conformational entropy as compared to the flexible 6-(3-pyridyl) hex-5-yn-1-ol group of saz-A (FIGS. 8 and 9). These additional interactions and favorable entropy penalty may likely confer affinity to VMY-2-95. The overlay of VMY-2-95 with saz-A, varenicline, and (−)-nicotine (FIG. 9) reveals that VMY-2-95 forms more favorable hydrophobic interactions with the α4β2 nAChR and occupies different receptor space that may be critical for selectivity.

Physicochemistry Properties of the New Ligands

Several key physicochemical parameters of compounds may have important roles in influencing the blood-brain barrier (BBB) penetration of CNS drugs, including molecular weight (MW), polar surface area (PSA) and lipophilicity (c log P). These parameters of all series 1 compounds were calculated and presented in FIG. 20.

In general CNS drugs have a MW≤450-Da. All the compounds in this report will have molecular weights less than 450 Da. In addition, all these compounds have c log P values <5, suggesting a reasonable probability of good oral absorption and intestinal permeability.

In general, a Polar surface area (PSA) less than 60 $Å^2$ is predictive for a compound to penetrate BBB well. As shown in FIG. 20, all the compounds in series 1 have PSA values smaller than 60 $Å^2$.

We also calculated the log BB, which is a parameter commonly used to express the extent of a drug passing through the blood-brain barrier. Several QSAR model were developed to calculate the log BB. In this study, we predicted the log BB values for compounds in series 1. In general a log BB value greater than zero is a favorable factor for BBB penetration. The log BB values of all compounds in series 1 were in the positive range.

Ligand efficiency (LE) is an important metric in drug discovery and has been used to measure the relationship of biological activity (affinity) with molecular size. LE is the ratio of the free energy of binding over the number of heavy atoms in a molecule. LE is a useful optimization tool to evaluate a ligand's ability to effectively bind to the targeted protein. Considering the binding affinity (IQ of the compounds in series 1, we calculated the LE. All compounds in series 1 have a LE value in the range of 0.7 kcal/mole (a LE≥0.3 is favorable, FIG. 20) and suggest that these compounds are optimized for receptor occupancy.

Tobacco use and nicotine addiction impose a huge health and economic burden. To date, there are only three classes of medications that have been approved by the U.S. Food and Drug Administration for smoking cessation: nicotine replacement therapy, bupropion and varenicline. Among the three, varenicline (Chantix©) is considered superior in terms of relative efficacy. However, the percentage of subjects who remained smoke-free for 12 months following treatment with varenicline fell to ~22%. Moreover, although varenicline appears to be safe for most people, exacerbation of schizophrenia and manic episodes associated with treatment with varenicline have been reported. In addition, based on a recent report, the FDA issued a "notification", warning that varenicline may be associated with increased adverse cardiovascular events, including angina and heart attack. More commonly, nearly 30% of participants taking varenicline in clinical trials reported nausea and 18% reported vomiting.

Although varenicline was developed as a partial agonist at α4β2 nAChRs, it is also nearly a full agonist at α3β4 nAChRs, which predominate in autonomic ganglia and brainstem autonomic centers, as well as at α7 nAChRs, another important subtype in brain. More recently, varenicline was found to be a potent agonist of the human 5-hydroxytryptamine$_3$ receptors (5-HT$_3$). The side effects of varenicline are most likely to be mediated through its actions at receptors other than α4β2 nAChRs, including α3β4* nAChRs, α7 nAChRS and 5-HT$_3$ receptors.

Given the grave health and economic consequences of smoking there is an obvious great need for significant improvement in the existing smoking cessation therapies. In 2006, resulted from our study of Sazetidine-A (Saz-A), we proposed a new strategy to develop novel nicotinic therapeutics, including smoking cessation aids, based on their ability to selectively desensitize α4β2 nAChRs. Saz-A is a novel nAChR ligand that is highly selective for α4β2 receptors. In binding assays, Saz-A has a much higher binding affinity for α4β2 nAChRs than for α3β4 or α7 receptors. After cells are exposed to it for 10 min, Saz-A potently (IC$_{50(10')}$=12 nM) inhibits nicotine-stimulated function mediated by α4β2 nAChRs (FIG. 17). Consistent with its high selectivity for α4β2 receptor Saz-A at concentrations up to 10 μM had no effect on the function of rat α3β4 nAChRs (FIG. 17). This is consistent with the hypothesis that Saz-A selectively desensitizes α4β2 receptors.

The high potency of Saz-A to desensitize α4β2 nAChRs in cells in vitro suggested that it would produce important effects similar to some of those produced by nicotine, but with much more receptor selectivity. It would therefore potentially be a drug candidate to help people overcome addiction to nicotine and to treat other CNS disorders. Since 2007, Saz-A has been shown to have efficacy in quite a few animal behavioral models.

In this study, we have developed a new class of selective α4β2 nAChR ligands. These compounds maintain the excellent pharmacological property profile of Saz-A with improved physicochemistry properties.

As shown in FIG. 14, in binding studies, similar to Saz-A, VMY-2-95 and analogs are highly selective to α4β2 nAChRs over α3β4 and α7 subtypes. As assessed in $^{86}$Rb$^1$ efflux assays, compared to nicotine, VMY-2-95 has less than 30% of efficacy in activating human α4β2 nAChRs. As the same as Saz-A, the compound does not show agonist activity at rat α3β4 nAChRs. VMY-2-95 potently and selectively desensitizes α4β2 nAChRs. Its potency for desensitization is close to that of Saz-A but much stronger than those of varenicline and nicotine.

VMY-2-95 and other compounds in series 1 have more favorable values of physicochemistry parameters, such as lower PSA and higher c log P than those of Saz-A, indicating the possibility that they may have better BBB penetration and higher brain distribution.

Consistent with the excellent pharmacological property profile and improved physicochemistry properties, in the initial in vivo studies (FIGS. 5 and 6), VMY-2-95 significantly reduces nicotine self-administration at 3 mg/kg in the rat model, showing promise as a smoking cessation aid.

To elucidate SAR for VMY-2-95, in addition to compounds in series 1 (VMY-2-95 through VMY-2-139), we also synthesized four compounds in series 2, including VMY-2-161, VMY-2-177, VMY-2-191 and VMY-2-205. The very low binding affinities of VMY-2-161 and VMY-2-177 may be an indication that the azetidine ring is important for good binding property profiles. The binding affinity of (S)—N-methyl compound VMY-2-205 is 25 times lower than that of corresponding (S)—N-H VMY-2-95. It is conceivable that the N—H provides a potentially important H-bond interaction. It is interesting that the two enantiomers, VMY-2-191 and VMY-2-95, showing a similar binding profile though VMY-2-191 has a slightly lower affinity for α4β2 receptors than VMY-2-95.

The binding model of α4β2 nAChR with VMY-2-95 suggests similar occupancy of the binding pocket as that of nicotine and varenicline. Moreover, the phenylethynyl group at C-5 position of pyridine in VMY-2-95 occupies a potentially critical space in the pocket and forms favorable hydrophobic interactions with α4β2 nAChR (FIGS. 8 and 9).

In screening against 41 targets other than nAChRs (FIG. 18), VMY-2-95 does not have high binding affinity for any of these targets. The compound either is not a "hit" in primary binding assays, or showing at least 3,000-fold lower binding affinities than that for α4β2 nAChRs in secondary binding assays (FIG. 19,). It is important to note that VMY-2-95 is not a "hit" at 5-HT$_3$ receptors, which mediate some of varenicline's adverse side effects, including nausea.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of treating a disorder selected from the group consisting of addiction, chemical substance abuse, alcoholism, comprising administering to a subject in need thereof a therapeutically effective amount of a compound of formula (I) or a pharmaceutically acceptable salt thereof:

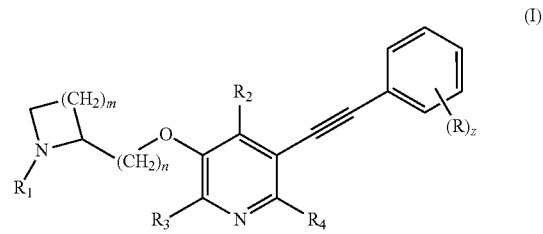

wherein:
R represents, independently for each occurrence, halogen, C1-C6 alkyl, allyl, C1-C6 alkyloxy, amino, hydroxyl, nitro, cyano, or trifluoro-C1-C4 alkyl;

$R_1$ represents hydrogen, C1-C6 alkyl, allyl, or C3-C6 cycloalkyl;

$R_2$, $R_3$, and $R_4$ independently represent hydrogen, C1-C6 alkyl, allyl, or C3-C6 cycloalkyl, or C1-C6 alkyl substituted with at least one fluorine;

m is 1;

n is an integer selected from 1 and 2; and z is an integer ranging from 0 to 5.

2. The method of claim 1, wherein $R_1$ represents hydrogen.

3. The method of claim 1, wherein $R_2$, $R_3$, and $R_4$ represent hydrogens.

4. The method of claim 1, wherein n is 1.

5. The method of claim 1, wherein z is 0.

6. The method of claim 1, wherein z is 1.

7. The method of claim 1, wherein z is 2.

8. The method of claim 1, wherein R represents halogen.

9. The method of claim 1, wherein R represents halogen, C1-C6 alkyl, C1-C6 alkoxy, amino, or trifluoro-C1-C4 alkyl.

10. The method of claim 1, wherein the compound of formula (I) is selected from the group consisting of:

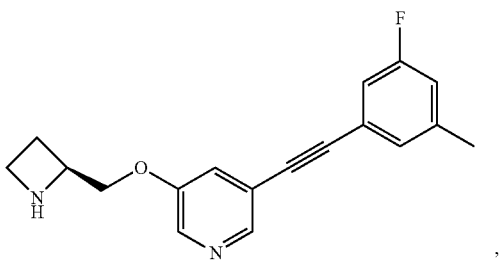

,

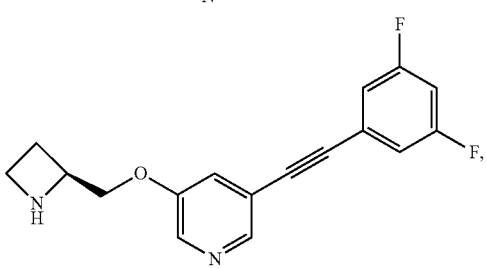

,

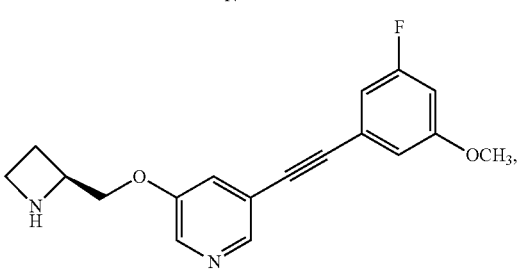

,

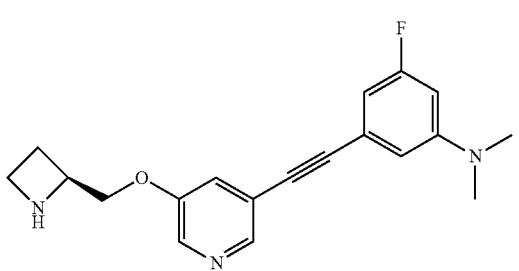

,

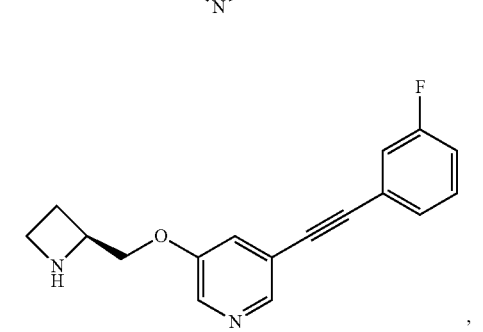

,

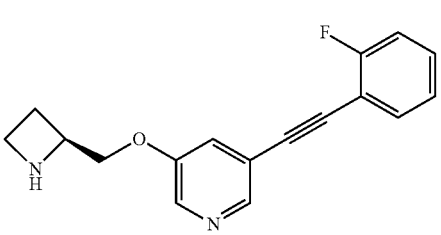

,

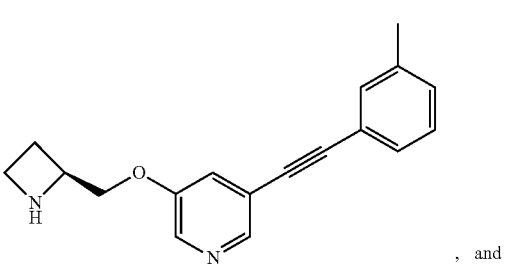

, and

-continued

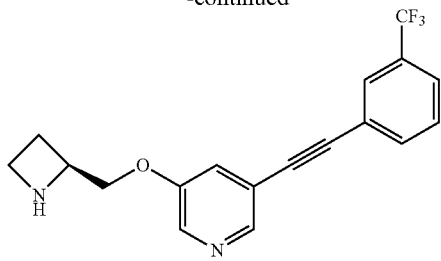

11. The method of claim 1, wherein the compound of formula (I) is

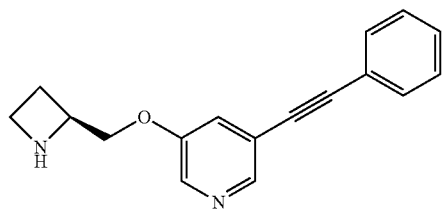

12. The method of claim 1, wherein the disorder is addiction.

13. The method of claim 12, wherein the compound of formula (I) is

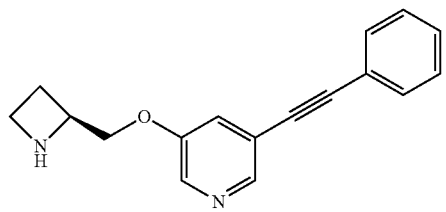

14. The method of claim 1, wherein the disorder is chemical substance abuse.

15. The method of claim 14, wherein the compound of formula (I) is

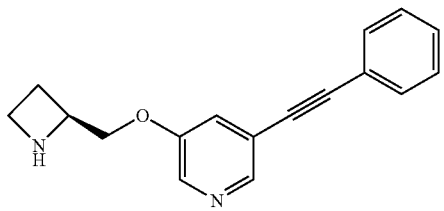

16. The method of claim 1, wherein the disorder is alcoholism.

17. The method of claim 16, wherein the compound of formula (I) is

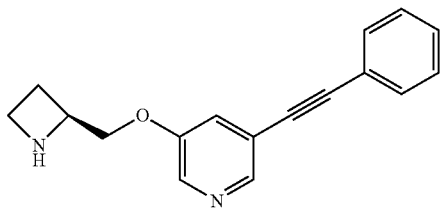

18. The method of claim 1, wherein the disorder is tobacco abuse.

19. The method of claim 18, wherein the compound of formula (I) is

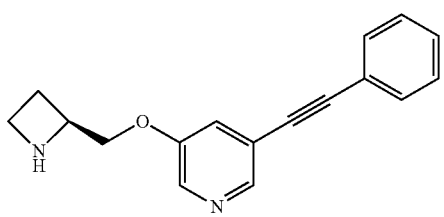

* * * * *